(12) United States Patent
Rosendahl et al.

(10) Patent No.: US 7,306,931 B2
(45) Date of Patent: Dec. 11, 2007

(54) METHOD FOR REFOLDING PROTEINS CONTAINING FREE CYSTEINE RESIDUES

(75) Inventors: Mary S. Rosendahl, Broomfield, CO (US); George N. Cox, Louisville, CO (US); Daniel H. Doherty, Boulder, CO (US)

(73) Assignee: Bolder Biotechnology, Inc., Boulder, CO (US)

(*) Notice: Subject to any disclaimer, the term of this patent is extended or adjusted under 35 U.S.C. 154(b) by 456 days.

(21) Appl. No.: 10/276,358

(22) PCT Filed: May 16, 2001

(86) PCT No.: PCT/US01/16088

§ 371 (c)(1),
(2), (4) Date: Apr. 10, 2003

(87) PCT Pub. No.: WO01/87925

PCT Pub. Date: Nov. 22, 2001

(65) Prior Publication Data

US 2004/0018586 A1    Jan. 29, 2004

Related U.S. Application Data

(66) Substitute for application No. 60/204,617, filed on May 16, 2000.

(51) Int. Cl.
*C12P 21/00* (2006.01)
*C07K 5/00* (2006.01)

(52) U.S. Cl. ............................ 435/69.1; 530/408

(58) Field of Classification Search ............... None
See application file for complete search history.

(56) References Cited

U.S. PATENT DOCUMENTS

| | | | |
|---|---|---|---|
| 5,206,344 A | 4/1993 | Katre et al. | |
| 5,223,407 A | 6/1993 | Wong et al. | |
| 5,766,897 A | 6/1998 | Braxton | |
| 5,849,535 A | 12/1998 | Cunningham et al. | |
| 6,780,613 B1 | 8/2004 | Wells et al. | |

FOREIGN PATENT DOCUMENTS

| | | |
|---|---|---|
| EP | 0 312 358 A2 | 4/1989 |
| EP | 0 355 460 A2 | 2/1990 |
| EP | 0 458 064 A2 | 11/1991 |
| WO | WO 93/00109 | 1/1993 |
| WO | WO 94/01453 | 1/1994 |
| WO | WO 94/12219 | 6/1994 |
| WO | WO 95/32003 | 11/1995 |
| WO | WO 99/03887 | 1/1999 |
| WO | WO 00/42175 | 7/2000 |

OTHER PUBLICATIONS

Wells, 1990, Biochemistry 29:8509-8517.*
Ngo et al., 1994, The Protein Folding Problem and Tertiary Structure Prediction, pp. 492-495.*
M. Watahiki, 1992, Mie Medical Journal, 42(1):89-106.*
Cardamone 1995, Biochemistry, 34, 5773-5794.*
Goodson et al., *Biotechnology*, (8), 1990, 343-346.
Campbell, et al., *J Peptide Res.*, (49), 1997, 527-537.

* cited by examiner

*Primary Examiner*—Elizabeth C. Kemmerer
*Assistant Examiner*—Christina Borgeest
(74) *Attorney, Agent, or Firm*—Sheridan Ross P.C.

(57) ABSTRACT

The present invention relates to novel methods for making and refolding insoluble or aggregated proteins having free cysteines in which a host cell expressing the protein is exposed to a cysteine blocking agent. The soluble, refolded proteins produced by the novel methods can then be modified to increase their effectiveness. Such modifications include attaching a PEG moiety to form PEGylated proteins.

49 Claims, No Drawings

SEQUENCE LISTING

```
<160> NUMBER OF SEQ ID NOS: 79

<210> SEQ ID NO 1
<211> LENGTH: 36
<212> TYPE: DNA
<213> ORGANISM: Artificial
<220> FEATURE:
<223> OTHER INFORMATION: primer

<400> SEQUENCE: 1
cgcaagcttg ccaccatggc tggacctgcc acccag                             36

<210> SEQ ID NO 2
<211> LENGTH: 36
<212> TYPE: DNA
<213> ORGANISM: Artificial
<220> FEATURE:
<223> OTHER INFORMATION: primer

<400> SEQUENCE: 2
cgcggatcct ccggagggct gggcaaggtg gcgtag                             36

<210> SEQ ID NO 3
```

```
<211> LENGTH: 66
<212> TYPE: DNA
<213> ORGANISM: Artificial
<220> FEATURE:
<223> OTHER INFORMATION: primer

<400> SEQUENCE: 3
ggcccggcca gctccctgcc gcagagcttc ctgctgaaga gcctcgagca agtgcgtaag      60
atccag                                                                66

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
cgcgaattct tagggctggg caaggtggcg                                       30

<210> SEQ ID NO 5
<211> LENGTH: 66
<212> TYPE: DNA
<213> ORGANISM: Artificial
<220> FEATURE:
<223> OTHER INFORMATION: primer

<400> SEQUENCE: 5
ggcccggcca gctccctgcc gcagagcttc ctgcttaagt gcctcgagca agtgcgtaag      60
atccag                                                                66

<210> SEQ ID NO 6
<211> LENGTH: 63
<212> TYPE: DNA
<213> ORGANISM: Artificial
<220> FEATURE:
<223> OTHER INFORMATION: primer

<400> SEQUENCE: 6
atgttcgttt tctctatcgc taccaacgcg tacgcaaccc cgctgggccc ggccagctcc      60
ctg                                                                   63

<210> SEQ ID NO 7
<211> LENGTH: 66
<212> TYPE: DNA
<213> ORGANISM: Artificial
<220> FEATURE:
<223> OTHER INFORMATION: primer

<400> SEQUENCE: 7 cccctctag acatatgaag aagaacatcg cattcctgct ggcatctatg ttcgttttct      60
ctatcg                                                                66

<210> SEQ ID NO 8
<211> LENGTH: 29
<212> TYPE: DNA
<213> ORGANISM: Artificial
<220> FEATURE:
<223> OTHER INFORMATION: primer

<400> SEQUENCE: 8
cgccatatga ccccgctggg cccggccag                                        29
```

```
<210> SEQ ID NO 9
<211> LENGTH: 36
<212> TYPE: DNA
<213> ORGANISM: Artificial
<220> FEATURE:
<223> OTHER INFORMATION: primer

<400> SEQUENCE: 9
accaacgcgt acgcaacccc gtgtggcccg gccagc                              36

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
gccatcgccc tggatcttac g                                              21

<210> SEQ ID NO 11
<211> LENGTH: 36
<212> TYPE: DNA
<213> ORGANISM: Artificial
<220> FEATURE:
<223> OTHER INFORMATION: primer

<400> SEQUENCE: 11
accaacgcgt acgcatgccc gctgggcccg gccagc                              36

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
cgcgaattct tagggacagg caaggtggcg                                     30

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
gccatcgccc tggatcttac g                                              21

<210> SEQ ID NO 14
<211> LENGTH: 36
<212> TYPE: DNA
<213> ORGANISM: Artificial
<220> FEATURE:
<223> OTHER INFORMATION: primer

<400> SEQUENCE: 14
cgcgaattct taacagggct gggcaaggtg gcgtag                              36

<210> SEQ ID NO 15
<211> LENGTH: 27
<212> TYPE: DNA
<213> ORGANISM: Artificial
<220> FEATURE:
<223> OTHER INFORMATION: primer
```

```
-continued

<400> SEQUENCE: 15
ccgctgggcc cgtgcagctc cctgccg                                          27

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
cggcagggag ctgcacgggc ccagcgg                                          27

<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
ctatgcggca tcagagcaga ta                                               22

<210> SEQ ID NO 18
<211> LENGTH: 27
<212> TYPE: DNA
<213> ORGANISM: Artificial
<220> FEATURE:
<223> OTHER INFORMATION: primer

<400> SEQUENCE: 18
ctgggcccgg cctgctccct gccgcag                                          27

<210> SEQ ID NO 19
<211> LENGTH: 27
<212> TYPE: DNA
<213> ORGANISM: Artificial
<220> FEATURE:
<223> OTHER INFORMATION: primer

<400> SEQUENCE: 19
ctgcggcagg gagcaggccg ggcccag                                          27

<210> SEQ ID NO 20
<211> LENGTH: 27
<212> TYPE: DNA
<213> ORGANISM: Artificial
<220> FEATURE:
<223> OTHER INFORMATION: primer

<400> SEQUENCE: 20
aacccgtacg catgtacccc gctgggc                                          27

<210> SEQ ID NO 21
<211> LENGTH: 27
<212> TYPE: DNA
<213> ORGANISM: Artificial
<220> FEATURE:
<223> OTHER INFORMATION: primer

<400> SEQUENCE: 21
gcccagcggg gtacatgcgt acgcgtt                                          27

<210> SEQ ID NO 22
<211> LENGTH: 22
```

<212> TYPE: DNA
<213> ORGANISM: Artificial
<220> FEATURE:
<223> OTHER INFORMATION: primer

<400> SEQUENCE: 22
tgtggaattg tgagcggata ac                                    22

<210> SEQ ID NO 23
<211> LENGTH: 27
<212> TYPE: DNA
<213> ORGANISM: Artificial
<220> FEATURE:
<223> OTHER INFORMATION: primer

<400> SEQUENCE: 23
ggaatggccc cttgcctgca gcccacc                               27

<210> SEQ ID NO 24
<211> LENGTH: 27
<212> TYPE: DNA
<213> ORGANISM: Artificial
<220> FEATURE:
<223> OTHER INFORMATION: primer

<400> SEQUENCE: 24
ggtgggctgc aggcaagggg ccattcc                               27

<210> SEQ ID NO 25
<211> LENGTH: 27
<212> TYPE: DNA
<213> ORGANISM: Artificial
<220> FEATURE:
<223> OTHER INFORMATION: primer

<400> SEQUENCE: 25
gccctgcagc cctgccaggg tgccatg                               27

<210> SEQ ID NO 26
<211> LENGTH: 27
<212> TYPE: DNA
<213> ORGANISM: Artificial
<220> FEATURE:
<223> OTHER INFORMATION: primer

<400> SEQUENCE: 26
catggcaccc tggcagggct gcagggc                               27

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
ggtgccatgc cgtgcttcgc ctctgct                               27

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
agcagaggcg aagcacggca tggcacc                                              27

<210> SEQ ID NO 29
<211> LENGTH: 27
<212> TYPE: DNA
<213> ORGANISM: Artificial
<220> FEATURE:
<223> OTHER INFORMATION: primer

<400> SEQUENCE: 29
ccggccttcg cctgtgcttt ccagcgc                                              27

<210> SEQ ID NO 30
<211> LENGTH: 27
<212> TYPE: DNA
<213> ORGANISM: Artificial
<220> FEATURE:
<223> OTHER INFORMATION: primer

<400> SEQUENCE: 30
gcgctggaaa gcacaggcga aggccgg                                              27

<210> SEQ ID NO 31
<211> LENGTH: 27
<212> TYPE: DNA
<213> ORGANISM: Artificial
<220> FEATURE:
<223> OTHER INFORMATION: primer

<400> SEQUENCE: 31
cccacccagg gttgcatgcc ggccttc                                              27

<210> SEQ ID NO 32
<211> LENGTH: 27
<212> TYPE: DNA
<213> ORGANISM: Artificial
<220> FEATURE:
<223> OTHER INFORMATION: primer

<400> SEQUENCE: 32
gaaggccggc atgcaaccct gggtggg                                              27

<210> SEQ ID NO 33
<211> LENGTH: 27
<212> TYPE: DNA
<213> ORGANISM: Artificial
<220> FEATURE:
<223> OTHER INFORMATION: primer

<400> SEQUENCE: 33
atgccggcct tctgctctgc tttccag                                              27

<210> SEQ ID NO 34
<211> LENGTH: 27
<212> TYPE: DNA
<213> ORGANISM: Artificial
<220> FEATURE:
<223> OTHER INFORMATION: primer

<400> SEQUENCE: 34
ctggaaagca gagcagaagg ccggcat                                              27

<210> SEQ ID NO 35
<211> LENGTH: 21
<212> TYPE: DNA
<213> ORGANISM: Artificial

```
<220> FEATURE:
<223> OTHER INFORMATION: primer

<400> SEQUENCE: 35
ggccattccc agttcttcca t                                              21

<210> SEQ ID NO 36
<211> LENGTH: 24
<212> TYPE: DNA
<213> ORGANISM: Artificial
<220> FEATURE:
<223> OTHER INFORMATION: primer

<400> SEQUENCE: 36
ttcgttttct ctatcgctac caac                                           24

<210> SEQ ID NO 37
<211> LENGTH: 27
<212> TYPE: DNA
<213> ORGANISM: Artificial
<220> FEATURE:
<223> OTHER INFORMATION: primer

<400> SEQUENCE: 37
ctgcaggccc tgtgtgggat ctccccc                                        27

<210> SEQ ID NO 38
<211> LENGTH: 27
<212> TYPE: DNA
<213> ORGANISM: Artificial
<220> FEATURE:
<223> OTHER INFORMATION: primer

<400> SEQUENCE: 38 ggggagatc ccacacaggg cctgcag                                         27

<210> SEQ ID NO 39
<211> LENGTH: 27
<212> TYPE: DNA
<213> ORGANISM: Artificial
<220> FEATURE:
<223> OTHER INFORMATION: primer

<400> SEQUENCE: 39
ctggaaggga tctgccccga gttgggt                                        27

<210> SEQ ID NO 40
<211> LENGTH: 27
<212> TYPE: DNA
<213> ORGANISM: Artificial
<220> FEATURE:
<223> OTHER INFORMATION: primer

<400> SEQUENCE: 40
acccaactcg gggcagatcc cttccag                                        27

<210> SEQ ID NO 41
<211> LENGTH: 35
<212> TYPE: DNA
<213> ORGANISM: Artificial
<220> FEATURE:
<223> OTHER INFORMATION: primer

<400> SEQUENCE: 41
cgcgctgcag ttctcatgtt tgacagctta tcatc                               35
```

<210> SEQ ID NO 42
<211> LENGTH: 42
<212> TYPE: DNA
<213> ORGANISM: Artificial
<220> FEATURE:
<223> OTHER INFORMATION: primer

<400> SEQUENCE: 42
cgcgctgcag atttaaatta gcgaggtgcc gccggcttcc at        42

<210> SEQ ID NO 43
<211> LENGTH: 38
<212> TYPE: DNA
<213> ORGANISM: Artificial
<220> FEATURE:
<223> OTHER INFORMATION: primer

<400> SEQUENCE: 43
gcgacgcgta cgcagcaccc acccgctcac ccatcact            38

<210> SEQ ID NO 44
<211> LENGTH: 42
<212> TYPE: DNA
<213> ORGANISM: Artificial
<220> FEATURE:
<223> OTHER INFORMATION: primer

<400> SEQUENCE: 44
gcggaattct tatttttgga ctggtttttt gcattcaaag gg        42

<210> SEQ ID NO 45
<211> LENGTH: 38
<212> TYPE: DNA
<213> ORGANISM: Artificial
<220> FEATURE:
<223> OTHER INFORMATION: primer

<400> SEQUENCE: 45
gcgacgcgta cgcagcaccc tgccgctcac ccatcact            38

<210> SEQ ID NO 46
<211> LENGTH: 32
<212> TYPE: DNA
<213> ORGANISM: Artificial
<220> FEATURE:
<223> OTHER INFORMATION: primer

<400> SEQUENCE: 46
ccaacgcgta cgcagcccca ccacgcctca tc                  32

<210> SEQ ID NO 47
<211> LENGTH: 33
<212> TYPE: DNA
<213> ORGANISM: Artificial
<220> FEATURE:
<223> OTHER INFORMATION: primer

<400> SEQUENCE: 47
ccggaattct taacggtcac ctgtgcggca ggc                 33

<210> SEQ ID NO 48
<211> LENGTH: 30
<212> TYPE: DNA
<213> ORGANISM: Artificial
<220> FEATURE:
<223> OTHER INFORMATION: primer

```
<400> SEQUENCE: 48
ccggaattct tagtcacctg tgcggcaggc                                30

<210> SEQ ID NO 49
<211> LENGTH: 57
<212> TYPE: DNA
<213> ORGANISM: Artificial
<220> FEATURE:
<223> OTHER INFORMATION: primer

<400> SEQUENCE: 49
ttcgctagca tgcatgacct gcaggaggaa atttaaatgg ccccaccacg cctcatc   57

<210> SEQ ID NO 50
<211> LENGTH: 39
<212> TYPE: DNA
<213> ORGANISM: Artificial
<220> FEATURE:
<223> OTHER INFORMATION: primer

<400> SEQUENCE: 50
gctaacgcgt acgcacacag ccaccgcgac ttccagccg                      39

<210> SEQ ID NO 51
<211> LENGTH: 38
<212> TYPE: DNA
<213> ORGANISM: Artificial
<220> FEATURE:
<223> OTHER INFORMATION: primer

<400> SEQUENCE: 51
cggaattcct cgagctactt ggaggcagtc atgaagct                       38

<210> SEQ ID NO 52
<211> LENGTH: 90
<212> TYPE: DNA
<213> ORGANISM: Artificial
<220> FEATURE:
<223> OTHER INFORMATION: primer

<400> SEQUENCE: 52
gtgcaccata tgaagaagaa catcgcattc ctgctggcta gcatgcatga cctgcaggag   60
gaaatttaaa tgcacagcca ccgcgacttc                                90

<210> SEQ ID NO 53
<211> LENGTH: 37
<212> TYPE: DNA
<213> ORGANISM: Artificial
<220> FEATURE:
<223> OTHER INFORMATION: primer

<400> SEQUENCE: 53
gaggaaattt aaatgtgcca cagccatcgc gacttcc                        37

<210> SEQ ID NO 54
<211> LENGTH: 22
<212> TYPE: DNA
<213> ORGANISM: Artificial
<220> FEATURE:
<223> OTHER INFORMATION: primer

<400> SEQUENCE: 54
tgtggaattg tgagcggata ac                                        22
```

<210> SEQ ID NO 55
<211> LENGTH: 37
<212> TYPE: DNA
<213> ORGANISM: Artificial
<220> FEATURE:
<223> OTHER INFORMATION: primer

<400> SEQUENCE: 55
ggaagtcgcg atggctgtgg cacatttaaa tttcctc                    37

<210> SEQ ID NO 56
<211> LENGTH: 35
<212> TYPE: DNA
<213> ORGANISM: Artificial
<220> FEATURE:
<223> OTHER INFORMATION: primer

<400> SEQUENCE: 56
gaggaaattt aaattgcagc catcgcgact tccag                      35

<210> SEQ ID NO 57
<211> LENGTH: 36
<212> TYPE: DNA
<213> ORGANISM: Artificial
<220> FEATURE:
<223> OTHER INFORMATION: primer

<400> SEQUENCE: 57
ctggaagtcg cgatggctgc acatttaaat ttcctc                     36

<210> SEQ ID NO 58
<211> LENGTH: 27
<212> TYPE: DNA
<213> ORGANISM: Artificial
<220> FEATURE:
<223> OTHER INFORMATION: primer

<400> SEQUENCE: 58
atgcacagcc actgcgactt ccagccg                               27

<210> SEQ ID NO 59
<211> LENGTH: 27
<212> TYPE: DNA
<213> ORGANISM: Artificial
<220> FEATURE:
<223> OTHER INFORMATION: primer

<400> SEQUENCE: 59
cggctggaag tcgcagtggc tgtgcat                               27

<210> SEQ ID NO 60
<211> LENGTH: 29
<212> TYPE: DNA
<213> ORGANISM: Artificial
<220> FEATURE:
<223> OTHER INFORMATION: primer

<400> SEQUENCE: 60
gccaccgcga ctgtcaaccg gtgctccac                             29

<210> SEQ ID NO 61
<211> LENGTH: 29
<212> TYPE: DNA
<213> ORGANISM: Artificial
<220> FEATURE:
<223> OTHER INFORMATION: primer

<400> SEQUENCE: 61
gtggagcacc ggttgacagt cgcggtggc                              29

<210> SEQ ID NO 62
<211> LENGTH: 31
<212> TYPE: DNA
<213> ORGANISM: Artificial
<220> FEATURE:
<223> OTHER INFORMATION: primer

<400> SEQUENCE: 62
catgcggggc atctgcggcg ccgacttcca g                           31

<210> SEQ ID NO 63
<211> LENGTH: 31
<212> TYPE: DNA
<213> ORGANISM: Artificial
<220> FEATURE:
<223> OTHER INFORMATION: primer

<400> SEQUENCE: 63
ctggaagtcg gcgccgcaga tgccccgcat g                           31

<210> SEQ ID NO 64
<211> LENGTH: 27
<212> TYPE: DNA
<213> ORGANISM: Artificial
<220> FEATURE:
<223> OTHER INFORMATION: primer

<400> SEQUENCE: 64
ggctctgttc tcgtgctctg agggtcc                                27

<210> SEQ ID NO 65
<211> LENGTH: 27
<212> TYPE: DNA
<213> ORGANISM: Artificial
<220> FEATURE:
<223> OTHER INFORMATION: primer

<400> SEQUENCE: 65
ggaccctcag agcacgagaa cagagcc                                27

<210> SEQ ID NO 66
<211> LENGTH: 27
<212> TYPE: DNA
<213> ORGANISM: Artificial
<220> FEATURE:
<223> OTHER INFORMATION: primer

<400> SEQUENCE: 66
ccgctgaagc cctgcgcacg catcttc                                27

<210> SEQ ID NO 67
<211> LENGTH: 27
<212> TYPE: DNA
<213> ORGANISM: Artificial
<220> FEATURE:
<223> OTHER INFORMATION: primer

<400> SEQUENCE: 67
gaagatgcgt gcgcagggct tcagcgg                                27

<210> SEQ ID NO 68

```
<211> LENGTH: 30
<212> TYPE: DNA
<213> ORGANISM: Artificial
<220> FEATURE:
<223> OTHER INFORMATION: primer

<400> SEQUENCE: 68
gacgtcctga ggtgcccgac ctggccccag                                      30

<210> SEQ ID NO 69
<211> LENGTH: 33
<212> TYPE: DNA
<213> ORGANISM: Artificial
<220> FEATURE:
<223> OTHER INFORMATION: primer

<400> SEQUENCE: 69
ggccaggcct ccagcctctg cgggggcagg ctc                                  33

<210> SEQ ID NO 70
<211> LENGTH: 33
<212> TYPE: DNA
<213> ORGANISM: Artificial
<220> FEATURE:
<223> OTHER INFORMATION: primer

<400> SEQUENCE: 70
gagcctgccc ccgcagaggc tggaggcctg gcc                                  33

<210> SEQ ID NO 71
<211> LENGTH: 36
<212> TYPE: DNA
<213> ORGANISM: Artificial
<220> FEATURE:
<223> OTHER INFORMATION: primer

<400> SEQUENCE: 71
ctgctggggg gctgcctcct gggccagagt gccgcg                               36

<210> SEQ ID NO 72
<211> LENGTH: 36
<212> TYPE: DNA
<213> ORGANISM: Artificial
<220> FEATURE:
<223> OTHER INFORMATION: primer

<400> SEQUENCE: 72
cgcggcactc tggcccagga ggcagccccc cagcag                               36

<210> SEQ ID NO 73
<211> LENGTH: 31
<212> TYPE: DNA
<213> ORGANISM: Artificial
<220> FEATURE:
<223> OTHER INFORMATION: primer

<400> SEQUENCE: 73
ctcctggggc agtgcgcagc gagctgccat c                                    31

<210> SEQ ID NO 74
<211> LENGTH: 31
<212> TYPE: DNA
<213> ORGANISM: Artificial
<220> FEATURE:
<223> OTHER INFORMATION: primer

<400> SEQUENCE: 74
```

```
gatggcagct cgctgcgcac tgccccagga g                                    31

<210> SEQ ID NO 75
<211> LENGTH: 21
<212> TYPE: DNA
<213> ORGANISM: Artificial
<220> FEATURE:
<223> OTHER INFORMATION: primer

<400> SEQUENCE: 75
gacactgctg ctgagatgaa t                                               21

<210> SEQ ID NO 76
<211> LENGTH: 22
<212> TYPE: DNA
<213> ORGANISM: Artificial
<220> FEATURE:
<223> OTHER INFORMATION: primer

<400> SEQUENCE: 76
cttgtagtgg ctggccatca tg                                              22

<210> SEQ ID NO 77
<211> LENGTH: 57
<212> TYPE: DNA
<213> ORGANISM: Artificial
<220> FEATURE:
<223> OTHER INFORMATION: primer

<400> SEQUENCE: 77
cgcaacgcgt acgcagcacc ggcccgctcg ccgagcccga gcacgcagcc gtgggag        57

<210> SEQ ID NO 78
<211> LENGTH: 57
<212> TYPE: DNA
<213> ORGANISM: Artificial
<220> FEATURE:
<223> OTHER INFORMATION: primer

<400> SEQUENCE: 78
cgcgaattct tactcctgga ccggctccca gcagtcaaac gggatgacca gcagaaa       57

<210> SEQ ID NO 79
<211> LENGTH: 28
<212> TYPE: DNA
<213> ORGANISM: Artificial
<220> FEATURE:
<223> OTHER INFORMATION: primer

<400> SEQUENCE: 79
gttggtcaac tcgagccagc cgtgggag                                        28
```

METHOD FOR REFOLDING PROTEINS CONTAINING FREE CYSTEINE RESIDUES

CROSS-REFERENCE TO RELATED APPLICATIONS

This application is a national stage application under 35 U.S.C. § 371 of PCT Application No. PCT/US01/16088, flied May 16, 2001, which claims the benefit of priority under 35 U.S.C. § 119(e) to U.S. Provisional Application Ser. No. 60/204,617, filed May 16, 2000. The entire disclosures of the above-identified applications are incorporated herein by reference.

FIELD OF THE INVENTION

The present invention relates generally to methods of making proteins and more specifically to recombinant proteins containing at least one "free" cysteine residue, i.e., a cysteine residue that does not participate in a disulfide bond.

BACKGROUND OF THE INVENTION

Protein therapeutics generally must be administered to patients by injection. Most protein therapeutics are cleared rapidly from the body, necessitating frequent, often daily, injections. There is considerable interest in the development of methods to prolong the circulating half-lives of protein therapeutics in the body so that the proteins do not have to be injected frequently. Covalent modification of proteins with polyethylene glycol (PEG) has proven to be a useful method to extend the circulating half-lives of proteins in the body (Abuchowski et al., 1984; Hershfield, 1987; Meyers et al., 1991). Covalent attachment of PEG to a protein increases the protein's effective size and reduces its rate of clearance from the body. PEGs are commercially available in several sizes, allowing the circulating half-lives of PEG-modified proteins to be tailored for individual indications through use of different size PEGs. Other documented in vivo benefits of PEG modification are an increase in protein solubility and stability, and a decrease in protein immunogenicity (Katre et al., 1987; Katre, 1990).

One known method for PEGylating proteins covalently attaches PEG to cysteine residues using cysteine-reactive PEGs. A number of highly specific, cysteine-reactive PEGs with different reactive groups (e.g., maleimide, vinylsulfone) and different size PEGs (2-40 kDa, single or branched chain) are commercially available. At neutral pH, these PEG reagents selectively attach to "free" cysteine residues, i.e., cysteine residues not involved in disulfide bonds. Cysteine residues in most proteins participate in disulfide bonds and are not available for PEGylation using cysteine-reactive PEGs. Through in vitro mutagenesis using recombinant DNA techniques, additional cysteine residues can be introduced anywhere into the protein. The newly added "free" or "non-natural" cysteines can serve as sites for the specific attachment of a PEG molecule using cysteine-reactive PEGs. The added "free" or "non-natural" cysteine residue can be a substitution for an existing amino acid in a protein, added preceding the amino-terminus of the mature protein or after the carboxy-terminus of the mature protein, or inserted between two normally adjacent amino acids in the protein. Alternatively, one of two cysteines involved in a native disulfide bond may be deleted or substituted with another amino acid, leaving a native cysteine (the cysteine residue in the protein that normally would form a disufide bond with the deleted or substituted cysteine residue) free and available for chemical modification. Preferably the amino acid substituted for the cysteine would be a neutral amino acid such as serine or alanine. For example, human growth hormone (hGH) has two disulfide bonds that can be reduced and alkylated with iodoacetamide without impairing biological activity (Bewley et al., (1969). Each of the four cysteines would be reasonable targets for deletion or substitution by another amino acid.

Several naturally occurring proteins are known to contain one or more "free" cysteine residues. Examples of such naturally occurring proteins include human Interleukin (IL)-2 (Wang et al., 1984), beta interferon (Mark et al., 1984; 1985), G-CSF (Lu et al., 1989) and basic fibroblast growth factor (bFGF, Thompson, 1992). IL,2, Granulocyte Colony-Stimulating Factor (G-CSF) and beta interferon (IFN-β) contain an odd number of cysteine residues, whereas basic fibroblast growth factor contains an even number of cysteine residues.

Expression of recombinant proteins containing free cysteine residues has been problematic due to reactivity of the free sulfhydryl at physiological conditions. Several recombinant proteins containing free cysteines have been expressed cytoplasmically, i.e., as intracellular proteins, in bacteria such as *E. coli*. Examples include natural proteins such as IL-2, beta interferon, G-CSF, and engineered cysteine muteins of IL-2 (Goodson and Katre, 1990), IL-3 (Shaw et al., 1992), Tumor Necrosis Factor Binding Protein (Tuma et al., 1995), Insulin-like Growth Factor-I (IGF-I, Cox and McDermott, 1994), Insulin-like Growth Factor binding protein-1 (IGFBP-1, Van Den Berg et al., 1997) and protease nexin and related proteins (Braxton, 1998). All of these proteins were predominantly insoluble when expressed intracellularly in *E. coli*. The insoluble proteins were largely inactive and needed to be refolded in order to regain significant biological activity. In some cases the reducing agent dithiothreitol (DTT) was used to aid solubilzation and/or refolding of the insoluble proteins. Purified, refolded IL-2, G-CSF and beta interferon proteins are unstable and lose activity at physiological pH, apparently due to disulfide rearrangements involving the free cysteine residue (Wang et al., 1984; Mark et al., 1984; 1985; Oh-eda et al., 1990; Arakawa et al., 1992). Replacement of the free cysteine residue in these proteins with serine, resulted in a protein that was more stable at physiological pH (Wang et al., 1984; Mark et al., 1984; 1985; Arakawa et al., 1993).

A second known method for expressing recombinant proteins in bacteria is to secrete them into the periplasmic space or into the media. It is known that certain recombinant proteins such as GH are expressed in a soluble active form when they are secreted into the *E. coli* periplasmic, whereas they are insoluble when expressed intracellularly in *E. coli*. Secretion is achieved by fusing DNA sequences encoding GH or other proteins of interest to DNA sequences encoding bacterial signal sequences such as those derived from the stII (Fujimoto et al., 1988) and ompA proteins (Ghrayeb et al., 1984). Secretion of recombinant proteins in bacteria is desirable because the natural N-terminus of the recombinant protein can be maintained. Intracellular expression of recombinant proteins requires that an N-terminal methionine be present at the amino-terminus of the recombinant protein. Methionine is not normally present at the amino-terminus of the mature forms of many human proteins. For example, the amino-terminal amino acid of the mature form of human GH is phenylalanine. An amino-terminal methionine must be added to the amino-terminus of a recombinant protein, if a methionine is not present at this position, in order for the protein to be expressed efficiently in bacteria. Typically addition of the amino-terminal methionine is accomplished by adding an ATG methionine codon preceding the DNA sequence encoding the recombinant protein. The added N-terminal methionine often is not removed from the recombinant protein, particularly if the recombinant protein is insoluble. Such is the case with hGH, where the N-terminal methionine is not removed when the protein is expressed intracellularly in E. coli. The added N-terminal methionine creates a "non-natural" protein that potentially can stimulate an immune response in a human. In contract, there is no added methionine on hGH that is secreted into the periplasmic space using stII (Chang et al., 1987) or ompA (Cheah et al., 1994) signal sequences; the recombinant protein begins with the native amino-terminal amino acid phenylalanine. The native hGH protein sequence is maintained because bacterial enzymes cleave the stII-hGH protein (or ompA-hGH protein) between the stII (or ompA) signal sequence and the start of the mature hGH protein.

hGH has four cysteines that form two disulfides. hGH can be secreted into the E. coli periplasmic using stII or ompA signal sequences. The secreted protein is soluble and biologically active (Hsiung et al., 1986). The predominant secreted form of hGH is a monomer with an apparent molecular weight by sodium dodecyl sulfate polyacrylamide gel electrophoresis (SDS-PAGE) of 22 kDa. Recombinant hGH can be isolated from the periplasmic space by using an osmotic shock procedure (Koshland and Botstein, 1980), which preferentially releases periplasmic, but not intracellular, proteins into the osmotic shock buffer. The released hGH protein is then purified by column chromatography (Hsiung et al., 1986). A large number of GH mutants have been secreted into the E. coli periplasmic. The secreted mutant proteins were soluble and could be purified using procedures similar to those used to purify wild type GH (Cunningham and Wells, 1989; Fuh et al., 1992). Unexpectedly, when similar procedures were used to secrete GH variants containing a free cysteine residue (five cysteines; 2N+1), it was discovered that certain recombinant GH variants were insoluble or formed multimers or aggregates when isolated using standard osmotic shock and purification procedures developed for GH. Very little of the monomeric GH variant proteins could be detected by non-reduced SDS-PAGE in the osmotic shock lysates. Insoluble or aggregated GH variants have reduced biological activities compared to soluble, properly folded hGH. Methods for refolding insoluble, secreted Growth Hormone variants containing a free cysteine residue into a biologically active form have not been described.

Alpha interferon (IFN-α2) also contains four cysteine residues that form two disulfide bonds. IFN-α2 can be secreted into the E. coli periplasmic using the stII signal sequence (Voss et al., 1994). A portion of the secreted protein is soluble and biologically active (Voss et al., 1994). Secreted, soluble recombinant IFN-α2 can be purified by column chromatography (Voss et al., 1994). When similar procedures were attempted to secrete IFN-α2 variants containing a free cysteine residue (five cysteines; 2N+1), it was discovered that certain of the recombinant IFN-α2 variants were predominantly insoluble or formed multimers or aggregates when isolated using standard purification procedures developed for IFN-α2. Insoluble or aggregated IFN-α2 variants have reduced biological activities compared to soluble, properly folded IFN-α2. Methods for refolding insoluble, secreted IFN-α2 variants containing a free cysteine residue into a biologically active form have not been described.

Human Granulocyte Colony-Stimulating Factor (G-CSF) contains five cysteine residues that form two disulfide bonds. The cysteine residue at position 17 in the mature protein sequence is free. Perez-Perez et al. (1995) reported that G-CSF could be secreted into the E. coli periplasmic using a variant form of the ompA signal sequence. However, very little of the ompA-CSF fusion protein was correctly processed to yield mature G-CSF. The percentage of correctly processed G-CSF could be improved by co-expressing the E. coli dnaK and dnaJ proteins in the host cells expressing the ompA-G-CSF fusion protein (Perez-Perez et al., 1995). Correctly processed, secreted G-CSF was largely insoluble in all E. coli strains examined (Perez-Perez et al., 1995). Insoluble G-CSF possesses reduced biological activity compared to soluble, properly folded G-CSF. When similar procedures were attempted to secrete wild type G-CSF, G-CSF variants in which the free cysteine residue was replaced with serine [G-CSF (C17S)], and G-CSF (C17S) variants containing a free cysteine residue (five cysteines; 2N+1) using the stII signal sequence, it was discovered that the recombinant G-CSF proteins also were predominantly insoluble. Methods for refolding insoluble, secreted G-CSF proteins into a biologically active form have not been described.

Human Granulocyte Macrophage Colony-Stimulating Factor (GM-CSF) contains four cysteine residues that form two disulfide bonds. Libbey et al. (1987) and Greenberg et al. (1988) reported that GM-CSF could be secreted into the E. coli periplasmic using the ompA signal sequence. Correctly processed, secreted GM-CSF was insoluble (Libbey et al., 1987; Greenberg et al., 1988). Insoluble GM-CSF possesses reduced biological activity compared to soluble, properly folded GM-CSF. When similar procedures were attempted to secrete GM-CSF variants containing a free cysteine residue (five cysteines; 2N+I) using the stII signal sequence, it was discovered that the recombinant GM-CSF proteins also were predominantly insoluble. Methods for refolding insoluble, secreted GM-CSF proteins into a biologically active form have not been described.

U.S. Pat. No. 5,206,344 and Goodson and Katre (1990) describe expression and purification of a cysteine substitution mutein of IL-2. The IL-2 cysteine mutein was insoluble when expressed intracellularly in E. coli. The protein was solubilized by treatment with a denaturing agent [either 10% sodium dodecyl sulfate (SDS) or 8M urea] and a reducing agent [100 mM dithiothreitol (DTT)], refolded and purified by size-exclusion chromatography and reversed phase HPLC. Expression and purification of cysteine muteins of IL-3 are described in U.S. Pat. No. 5,166,322. The IL-3 cysteine muteins also were insoluble when expressed intracellularly in E. coli. The proteins were solubilized with a denaturing agent (guanidine) and a reducing agent (DTT), refolded and purified by reversed phase HPLC. The purified IL3 cysteine muteins were kept in a partially reduced state by inclusion of DTT in the storage buffers. When the inventors used only a denaturing agent agent and a reducing agent (DTT) to denature and refold insoluble cysteine muteins of GH and G-CSF, it was discovered that the refolded proteins were heterogeneous, comprising multiple molecular weight species. Similarly, when the inventors denatured and refolded insoluble, secreted IFN-α2 cysteine muteins with only a denaturing agent and a reducing agent (DTT), undetectable levels of properly folded IFN-α2 cysteine muteins were obtained.

Malik et al. (1992) and Knusli et al. (1992) described conjugation of wild tpe GM-CSF with amine-reactive PEG reagents. The amine-PEGylated GM-CSF comprised a heterogeneous mixture of different molecular weight PEG-GM-CSF species modified at multiple amino acid residues (Malik et al. 1992; Knusli et al., 1992). The various amine-PEGylated GM-CSF species could not be purified from each other or from non-PEGylated GM-CSF by conventional chromatography methods, which prevented specific activity measurements of the various isoforms from being determined. Clark et al. (1996) described conjugation of GH with amine-reactive PEGs. Amine-PEGylated GH also was heterogeneous, comprising a mixture of multiple molecular weight species modified at multiple amino acid residues. The amine-PEGylated GH proteins displayed significantly reduced biological activity (Clark et al., 1996). Monkarsh et al. (1997) described amine-PEGylated alpha interferon, which also comprised multiple molecular weight species modified at different amino acid residues. Amine-PEGylated alpha interferon also displayed reduced biological activity. Tanaka et al. (1991) described amine-PEGylated G-CSF, which also comprised a heterogeneous mixture of different molecular weight species modified at different amino acid residues. Amine-PEGylated G-CSF displayed reduced biological activity (Tanaka et al., 1991). Kinstler et al. (1996) described a PEGylated G-CSF protein that is preferentially modified at the non-natural N-terminal methionine residue. This protein also displayed reduced biological activity (Kinstler et al. 1996).

Therefore, despite considerable effort, a need still exists for methods that allow an insoluble or aggregated protein containing one or more free cysteine residues to be refolded into a soluble, biologically active form in high yield. The present invention satisfies this need and provides related advantages as well. Similarly, a need also exists for methods of generating homogeneous preparations of long acting recombinant proteins by enhancement of protein molecular weight, such as by PEGylation.

SUMMARY OF THE INVENTION

The present invention generally relates to methods for obtaining refolded, soluble forms of proteins having one or more free cysteine residues and which are expressed by a host cell in an insoluble or aggregated form. Such proteins include, but are not limited to, members of the Growth Hormone supergene family, such as GH, IFN-α2, G-CSF and GM-CSF proteins, and anti-angiogenesis factors, such as endostatin and angiostatin. The methods are generally accomplished by (a) causing a host cell to express a protein containing a free cysteine residue in an insoluble or aggregated form; (b) lysing the cell; (c) solubilizing the insoluble or aggregated protein in the presence of a denaturing agent, a reducing agent and a cysteine blocking agent; and (d) refolding the protein by lowering the concentrations of the denaturing agent and reducing agents to levels sufficient to allow the protein to renature to a biologically active form Optionally, the soluble, refolded protein is isolated from other proteins in the refold mixture.

Suitable host cells include bacteria, yeast, insect or mammalian cells. Preferably, the host cell is a bacterial cell, particularly E. coli.

Preferably, the soluble, refolded proteins produced by the methods of the present invention are recombinant proteins, especially cysteine variants or cysteine muteins of a protein. As used herein, the terms "cysteine variant" and "cysteine mutein" are meant to encompass any of the following changes in a protein's amino acid sequence: addition of a non-natural cysteine residue preceding the amino terminus of the mature protein or following the carboxy-terminus of the mature protein; substitution of a non-natural cysteine residue for an existing amino acid in the protein; introduction of a non-natural cysteine residue between two normally adjacent amino acids in the protein; or substitution of another amino acid for a naturally occurring cysteine residue that normally form a disulfide bond in the protein. The methods are useful for producing proteins including, without limitation, GH, G-CSF, GM-CSF and interferon, especially alpha interferon, cysteine variants of these proteins, their derivatives or antagonists. Other proteins for which the methods are useful include other members of the GH supergene family, the Transforming Growth Factor (TGF)-beta superfamily, platelet derived growth factor-A, platelet derived growth factor-B, nerve growth factor, brain derived neurotophic factor, neurotrophin-3, neurotrophin4, vascular endothelial growth factor, chemokines, hormones, endostatin, angiostatin, cysteine muteins of these proteins, or a derivative or an antagonist thereof. Cysteine muteins of heavy or light chains of an immunoglobulin or a derivative thereof are also contemplated.

As used herein, the term "cysteine blocking agent" means any reagent or combination of reagents that result in the formation of a reversibly blocked free cysteine residue in a protein. Examples of useful cysteine blocking agents include, but are not limited to, dithiols such as cystine, cystamine, oxidized glutathione, dithioglycolic acid and the like, or thiols such as cysteine, cysteamine, thioglycolic acid, and reduced glutathione. Preferably, thiols should be used in the presence of an oxidizing agent. Useful oxidizing agents include oxygen, iodine, ferricyanide, hydrogen peroxide, dihydroascorbic acid, tetrathionate, and O-iodosobenzoate. Optionally, a metal ion such as copper ($Cu^{++}$) or cobalt ($Co^{++}$) can be added to catalyze the oxidation reaction. Although not wishing to be bound by any particular theory, the inventors postulate that the cysteine blocking agent forms a mixed disulfide with the free cysteine residue in the protein, thus limiting possible disulfide rearrangements that could occur involving the free cysteine residue. The mixed disulfide stabilizes the free cysteine residue, significantly enhancing the yield of properly folded, biologically active, soluble protein. As used herein, reducing agents such as DTT and 2-mercaptoethanol are not considered cysteine blocking agents because they do not result in the formation of a reversibly blocked mixed disulfide with the free cysteine residue in the protein. DTT typically does not form mixed disulfides with cysteine residues in proteins due to a thermodynamically preferred intramolecular bond that forms upon oxidation.

Higher order dimeric and multimeric proteins formed by the covalent association of two or more of the refolded proteins via their free cysteine residues also within the present invention.

The present methods further include various methods of attaching a cysteine-reactive moiety to the refolded protein to form modified protein in which the cysteine-reactive moiety is attached to the refolded protein through the free cysteine residue(s). An example of a useful cysteine-reactive moiety that can be attached to the refolded protein is a cysteine-reactive PEG, which can be used to form a PEGylated protein Such methods include (a) isolating the refolded protein having a free cysteine residue from other proteins in the refold mixture; (b) reducing, at least partially, the isolated, refolded protein with a disulfide-reducing agent and (c) exposing the protein to a cysteine-reactive moiety such as a cysteine-reactive PEG. Optionally, the modified protein can be isolated from unmodified protein. Examples of other useful cysteine-reactive moieties are cysteine-reactive dextrans, cysteine-reactive carbohydrates, cysteine-reactive poly (N-vinylpyrrolidone)s, cysteine-reactive peptides, cysteine-reactive lipids, and cysteine-reactive polysaccharides.

The present invention further includes the soluble, refolded proteins and their derivatives, including PEGylated proteins, made by the methods disclosed herein. Such PEGylated proteins include monopegylated, cysteine variants of GH, G-CSF, GM-CSF and alpha interferon proteins. Such PEGylated proteins also include cysteine variants of GH, G-CSF, GM-CSF and alpha interferon proteins modified with two or more PEG molecules, where at least one of the PEG molecules is attached to the protein through a free cysteine residue.

DETAILED DESCRIPTION OF THE INVENTION

The present invention provides novel methods of preparing refolded, soluble forms of GH, IFN-α2, G-CSF and GM-CSF proteins that have at least one free cysteine residue and which are expressed by a host cell in an insoluble or aggregated form. The present invention can be used to prepare refolded, soluble forms of other members of the GH supergene family that have at least one free cysteine residue and which are expressed by a host cell in an insoluble or aggregated form The present invention also can be used to prepare refolded, soluble forms of other types of proteins having at least one free cysteine residue and which are expressed by a host cell in an insoluble or aggregated form, including, but not limited to, anti-angiogenesis proteins such as endostatin and angiostatin. The invention further provides novel proteins, particularly recombinant proteins produced by these novel methods as well as derivatives of such recombinant proteins. The novel methods for preparing such proteins are generally accomplished by:
 (a) causing a host cell to express a protein having a free cysteine in an insoluble or aggregated form;
 (b) lysing the host cell by chemical, enzymatic or physical means;
 (c) solubilizing the insoluble or aggregated protein by exposing the protein to a denaturing agent, a reducing agent and a cysteine blocking agent; and
 (d) refolding the protein by reducing the concentrations of the denaturing agent and reducing agent in the solubilization mixture to levels sufficient to allow the protein to renature into a soluble, biologically active form.

Optionally, the refolded, soluble protein can be isolated from other proteins in the refold mixture. The methods and other embodiments of the present invention were described in detail in U.S. Provisional Application Ser. No. 60/204,617, filed May 16, 2000. U.S. Provisional Application Ser. No. 60/204,617 is incorporated herein by reference in its entirety.

As identified above, the first step in these methods is to cause a host cell to express a protein having a free cysteine residue in an insoluble or aggregated form Suitable host cells can be prokaryotic or eukaryotic. Examples of appropriate host cells that can be used to express recombinant proteins include bacteria, yeast, insect and mammalian cells. Bacteria cells are particularly useful, especially *E. coli*. Methods of causing a host cell to express a protein are well known in the art and examples are provided herein.

As used herein, the term "protein having a free cysteine residue" means any natural or recombinant protein or peptide that contains 2N+1 cysteine residues, where N can be 0 or any integer, and any natural or recombinant protein or peptide that contain 2N cysteines, where two or more of the cysteines do not normally participate in a disulfide bond. Thus, the methods of the present invention are useful in enhancing the expression, recovery and purification of any protein or peptide having a free cysteine, particularly cysteine added variant recombinant proteins (referred to herein as "cysteine muteins" or "cysteine variants") having one or more free cysteines. Although the expression, recovery and purification of a natural protein having a free cysteine expressed by its natural host cell can be enhanced by the methods of the present invention, the description herein predominantly refers to recombinant proteins for illustrative purposes only. In addition, the proteins can be derived from any animal species including human, companion animals and farm animals. The proteins also can be derived from plant species or microbes.

Accordingly, the present invention encompasses a wide variety of recombinant proteins, and cysteine variants of these proteins. These proteins include members of the GH supergene family, and cysteine variants of these proteins. The following proteins ("collectively referred to as the GH supergene family") are encoded by genes of the GH supergene family (Bazan (1990; 1991; 1992); Mott and Campbell (1995); Silvennoinen and Ihle (1996); Martin et al. (1990); Hannum et al. (1994); Blumberg et al., 2001): GH, prolactin, placental lactogen, erythropoietin (EPO), thrombopoietin (TPO), interleukin-2 (IL-2), IL-3, IL-4, IL-5, IL-6, IL7, IL-9, IL-10, IL-11, IL-12 (p35 subunit), IL13, IL-15, IL-19, IL-20, IL-TIF, MDA-7 AK-155, oncostatin M, ciliary neurotrophic factor, leukemia inhibitory factor, alpha interferon, beta interferon, gamma interferon, omega interferon, tau interferon, granulocyte-colony stimulating factor (GM-CSF), granulocyte-macrophage colony stimulating factor (GM-CSF), macrophage colony stimulating factor (M-CSF), cardiotrophin-1 (CT-1), Stem Cell Factor and the flt3/flt2 ligand. It is anticipated that additional members of the GH supergene family will be identified in the future through gene cloning and sequencing. Members of the GH supergene family have similar secondary and tertiary structures, despite the fact that they generally have limited amino acid or DNA sequence identity. The shared structural features of members of the GH supergene family, which are described in Bazan (1990; 1991; 1992), Mott and Campbell (1995) and Silvennoinen and Ihle (1996), allow new members of the gene family to be readily identified. Variants of these proteins such as the selective IL-2 antagonist described by Shanafelt et al. (2000) also are encompassed by this invention.

The present methods also can enhance the expression, recovery and purification of additional recombinant proteins, including members of the TGF-beta superfamily. Members of the TGF-beta superfamily include, but are not limited to, glial-derived neurotrophic factor (GDNF), transforming growth factor-beta1 (TGF-beta1), TGF-beta2, TGF-beta3, inhibin A, inhibin B, bone morphogenetic protein-2 (BMP-2), BMP-4, inhibin alpha, Mullerian inhibiting substance (MIS), and OP-1 (osteogenic protein 1). The monomer subunits of the TGF-beta superfamily share certain structural features that allow other members of this family to be readily identified: they generally contain 8 highly conserved cysteine residues that form 4 intramolecular disulfides. Typically a ninth conserved cysteine is free in the monomeric form of the protein but participates in an intermolecular disulfide bond formed during the homodimerization or heterodimerization of the monomer subunits. Other members of the TGF-beta superfamily are described by Massague (1990), Daopin et al. (1992), Kingsley (1994), Kutty et al. (1998), and Lawton et al. (1997), incorporated herein by reference.

Immunoglobulin (Ig) heavy and light chain monomers also contain cysteine residues that participate in intramolecular disulfides as well as free cysteines (Roitt et al., 1989 and Paul, 1989). These free cysteines normally only participate in disulfide bonds as a consequence of multimerization events such as heavy chain homodimerzation, heavy chain-light chain heterodimerization, homodimerization of the (heavy chain-light chain) heterodimers, and other higher order assemblies such as pentamerization of the (heavy chain-light chain) heterodimers in the case of IgM. Thus, the methods of the present invention can be employed to enhance the expression, recovery and purification of heavy and/or light chains (or various domains thereof) of human immunoglobulins such as for example IgG1, IgG2, IgG3, IgG4, IgM IgA1, IgA2, secretory IgA, IgD and IgE, and cysteine variants of these proteins or fragments thereof. Immunoglobulins from other species could also be similarly expressed, recovered and purified. Proteins genetically fused to immunoglobulins or immunoglobulin domains, as described in Chamow & Ashkenazi (1996), could also be similarly expressed, recovered and purified.

A group of proteins has been classed as a structural superfamily based on the shared structural motif termed the "cystine knot". The cystine knot is defined by six conserved cysteine residues that form three intramolecular disulfide bonds that are topologically "knotted" (McDonald and Hendrickson, 1993). These proteins also form homo- or heterodimers and in some but not all instances dimerization involves intermolecular disulfide formation. Members of this family include the members of the TGF-beta superfamily and other proteins such as platelet derived growth factor-A (PDGF-A), PDGF-B, nerve growth factor (NGF), brain derived neurotrophic factor (BDNF), neurotrophin-3 (NT-3), NT-4, and vascular endothelial growth factor (VEGF). Cysteine blocking reagents also could enhance expression, recovery and purification of proteins with this structural motif, and cysteine-added variants of these proteins.

The present methods also can enhance the expression, recovery and purification of other recombinant proteins and/or cysteine added variants of those proteins. Classes of proteins for which the present methods would be useful include proteases and other enzymes, protease inhibitors, cytolines, cytokine antagonists, cytokine "selective agonists", allergens, chemokines, gonadotrophins, chemotactins, lipid-binding proteins, pituitary hormones, growth factors, somatomedins, immunoglobulins, interleukins, interferons, soluble receptors, extracellular domains of cell-surface receptors, vaccines, single chain antibodies and hemoglobins. Specific examples of proteins include, for example, leptin, insulin, insulin-like growth factor I and II (IGF-I and IGF-II), superoxide dismutase, catalase, asparaginase, uricase, fibroblast growth factors, arginase, angiostatin, endostatin, Factor VIII, Factor, interleukin 1 receptor antagonist, parathyroid hormone, growth hormone releasing factor, calcitonin, extracellular domain of the VEGF receptor, protease nexin and anti-thrombin III.

Other protein variants that would benefit from PEGylation and would therefore be reasonable candidates for cysteine added modifications include proteins or peptides with poor solubility or a tendency to aggregate, proteins or peptides that are susceptable to proteolysis, proteins or peptides needing improved mechanical stability, proteins or peptides that are cleared rapidly from the body, or proteins or peptides with undesirable immunogenic or antigentic properties.

If desired, cysteine and other amino acid muteins of these proteins can be generally constructed using site-directed PCR-based mutagenesis as described in the Examples below and in PCT/US98/14497 and PCT/US00/0093, each of which is incorporated by reference in its entirety. Methods for constructing muteins using PCR based PCR procedures also are described in general in Methods in Molecular Biology, Vol. 15: PCR Protocols: Current Methods and Applications edited by White, B. A (1993) Humana Press, Inc., Totowa, N.J. and PCR Protocols: A Guide to Methods and Applications edited by Innis, M. A. et al. (1990) Academic Press, Inc. San Diego, Calif.

Methods known in the art can be used to induce expression of a protein in the cytoplasm or to direct secretion of the protein, depending on cell origin, including, for example, the methods described in the Examples below. A wide variety of signal peptides have been used successfully to transport proteins to the periplasmic space of E. coli. Examples of these include prokaryotic signal sequences such as ompA, stII, PhoA signal (Denefle et al., 1989), OmpT (Johnson et al., 1996), LamB and OmpF (Hoffman and Wright, 1985), beta-lactamase (Kadonaga et al., 1984), enterotoxins LT-A, LT-B (Morioka-Fujimoto et al., 1991), and protein A from S. aureus (Abrahmsen et al., 1986). A number of non-natural, synthetic, signal sequences that facilitate secretion of certain proteins are also known to those skilled in the art.

Next, the host cell is lysed. Cell lysis can occur prior to, or coincident with, the solubilization procedures described below. Cell lysis can be accomplished by, for example, mechanical sheer such as a French pressure cell, enzymatic digestion, sonication, homogenization, glass bead vortexing, detergent treatment, organic solvents, freeze thaw, grinding with alumina or sand, treatment with a denaturing agent as defined below, and the like (Bollag et al., 1996). Optionally, the cells can be lysed in the presence of a denaturing agent, a disulfide reducing agent, or a cysteine-blocking agent. Optionally, insoluble or aggregated material can be separated from soluble proteins by various methods such as centrifugation, filtration (including ultrafiltration), precipitation, floculation, or settling.

Next the insoluble or aggregated material (or whole cells without prior lysis) is rendered soluble or monomeric by exposing the insoluble or aggregated material (or whole cells without prior lysis) to a denaturing agent, and a disulfide reducing agent that also is a cysteine-blocking agent. Useful denaturing agents include urea, guandine, arginine, sodium thiocyanate, extremes in pH (dilute acids or bases), detergents (SDS, N-lauroyl sarcosine, sold under the trademark, SARKOSYL®), salts (chlorides, nitrates, thiocyanates, cetylmethylammonium salts, trichloroacetates), chemical derivatization (sulfitolysis, reaction with citraconic anhydride), solvents (2-amino-2-methyl-1-propanol or other alcohols, DMSO, DMF) or strong anion exchange resins such as Q-SEPHAROSE™. Useful concentrations of urea are 1-8 M, with 5-8 M being preferred concentrations. Useful concentrations of guanidine are 1-8 M, with 4-8 M being preferred concentrations. Useful disulfide reducing agents that also are cysteine blocking agents include, but are not limited to, thiols such as cysteine, thioglycolic acid, reduced glutathione and cysteamine. These compounds can be used in the range of 0.5 to 200 mM, with 1-50 mM being preferred concentrations. Cysteine, reduced glutathione, thioglycolic acid and cysteamine are preferred reducing agents because they also are cysteine blocking agents, i.e., they interact with the free cysteine residue in the protein to form a reversibly blocked free cysteine residue. Use of a disulfide-reducing agent that also is a cysteine blocking agent during the solubilization step reduces the number of compounds and steps required in the overall process for refolding the insoluble or aggregated protein to a soluble, active form. Furthermore, use of a cysteine blocking agent results in a form of the refolded protein that is suitable for derivatization at the free cysteine residue using various cysteine-reactive moieties and procedures described below. Preferably, the pH of the denaturation/reduction mixture is between pH 6 and pH 10.

The next step in the procedure is to refold the protein to obtain the protein's native conformation and native disulfide bonds. Refolding is achieved by reducing the concentrations of the denaturing agent and reducing agent to levels sufficient to allow the protein to renature into a soluble, biologically active form This can be achieved through dialysis, dilution, gel filtration, precipitation of the protein, or by immobilization on a resin followed by buffer washes. Conditions for this step are chosen to allow for regeneration of the protein's native disulfide bond(s). This can be accomplished through addition of an oxidizing agent, or a redox mixture of an oxidizing agent and a reducing agent, to catalyze a disulfide exchange reaction. Preferably, a reagent or combination of reagents are chosen that result in native disulfide bond formation and a reversibly blocked free cysteine residue, i.e., the reagent or combination of reagents acts as cysteine blocking agents. Examples of useful oxidizing reagents include oxygen, cystine, oxidized glutathione, cystamine, and dithioglycolic acid. Examples of useful redox mixtures include cysteine/oxygen, cysteine/cystine, cysteine/cystamine, cysteamine/cystamine, reduced glutathione/oxidized glutathione, and the like. Optionally, a reducing agent such as DTT or 2-mercaptoethanol can be added to the refold mixture to promote disulfide exchange. Optionally, a metal ion such as copper ($Cu^{++}$) or cobalt ($Co^{++}$) can be added to the refold mixture to promote protein oxidation. Useful concentrations of metal ions in the refold mixture are 1 µM to 1 mM, with 40 µM being a preferred concentration. Preferably, the pH of the refold mixture is between pH 6 and pH 10.

Alternatively, the insoluble or aggregated material (or whole cells without prior cell lysis) is rendered soluble or monomeric through the use of a denaturing agent and a disulfide reducing agent that may or may not be a cysteine blocking agent. Useful denaturing agents include, but are not limited to, those described above. Examples of useful disulfide reducing agents include, but are not limited to, DTT, 2-mercaptoethanol, sodium borohydride, tertiary phosphines and thiols such as cysteine, reduced glutathione, thioglycolic acid and cysteamine. DTT and 2-mercaptoethanol can be used in the range of 0.5-200 mM, with 1-50 mM being preferred concentrations. The denatured and reduced protein is then mixed with a molar excess (relative to the concentration of the reducing agent) of a dithiol reagent that, when reduced, can act as a cysteine blocking agent. Examples of useful dithiol reagents that can act as cysteine blocking agents when reduced include compounds containing disulfide linkages such as cystine, cystamine, oxidized glutathione, dithioglycolic acid, 5,5'-dithiobis(2-nitrobenzoic acid (Ellman's reagent), pyridine disulfides, compounds of the type R—S—S—CO—OCH$_3$, where R is an organic compound, other derivatives of cystine such as diformylcystine, diacetylcystine, diglycylcystine, dialanylcystine diglutaninylcystine, cystinyldiglycine, cystinyldiglutamine, dialanylcystine dianhydride, cystine phenylhydantoin, homocystine, dithiodipropionic acid, dimethylcystine, or any dithiol or chemical capable of undergoing a disulfide exchange reaction. Refolding of the protein is initiated by lowering the concentration of the denaturing agent (using the methods described above) and promoting disulfide exchange by addition of a reducing agent such as cysteine, dithiothreitol, 2-mercaptoethanol, reduced glutathione, thioglycolic acid or other thiol. Preferably, a reagent or combination of reagents are chosen that result in native disulfide bond formation and a reversibly blocked free cysteine residue. Optionally, a metal ion such as copper ($Cu^{++}$) or cobalt ($Co^{++}$), can be added to the refold mixture to promote protein oxidation. Optionally, glycerol can be added to the refold mixture to increase the yield of refolded protein. Useful concentrations of glycerol in the refold mixture are 1-50% (volume/volume), with 10-20% being a preferred range. Preferably, the pH of the refold mixture is 6-10.

Although not wishing to be bound by any particular theory, it is believed that the cysteine blocking agents used in the present methods covalently attach to the "free" cysteine residue, forming a mixed disulfide, thus stabilizing the free cysteine residue and preventing multimerization and aggregation of the protein. A number of thiol-reactive compounds can be used as cysteine blocking agents to stabilize proteins containing free cysteines. In addition to cysteine, cysteamine, thioglycolic acid and reduced glutathione, cysteine blocking agents can also include reagents containing disulfide linkages such as cystine, cystamine, dithioglycolic acid, oxidized glutathione, 5,5'-dithiobis(2-nitrobenzoic acid (Ellman's reagent), pyridine disulfides, compounds of the type R—S—S—CO—OCH$_3$, other derivatives of cystine such as diformylcystine, diacetylcystine, diglycylcystine, dialanylcystine diglutaminylcystine, cystinyldiglycine, cystinyldiglutamine, dialanylcystine dianhydride, cystine phenylhydantoin, homocystine, dithiodipropionic acid, dimethylcystine, or any dithiol or chemical capable of undergoing a disulfide exchange reaction. Sulfenyl halides can also be used to prepare mixed disulfides. Other thiol blocking agents that may find use in stabilizing proteins containing free cysteine residues include compounds that are able to reversibly react with free thiols. These agents include certain heavy metals salts or organic derivatives of zinc, mercury, and silver. Other mercaptide forming agents or reversible thiol reactive compounds are described by Cecil and McPhee (1959) and Torchinskii (1971).

Optionally, the refolded, soluble protein containing a free cysteine residue is recovered and isolated from other proteins in the soluble fraction of the refold mixture. Such recovery and purification methods are known or readily determined by those skilled in the art, including, for example, centrifugation, filtration, dialysis, chromatography, including size exclusion, ion-exchange, hydrophobic interaction and affinity chromatography procedures and the like. A suitable method for the recovery and purification of a desired protein will depend, in part, on the properties of the protein and the intended use.

The present invention also provides novel methods for producing biologically active G-CSF proteins, particularly wild type G-CSF, G-CSF (C17S), and G-CSF and G-CSF (C17S) variants, including cysteine variants, (collectively referred to as "G-CSF proteins"), that result in a significant increase in the percentage of the recovered G-CSF proteins that has been properly processed and is biologically active. These novel methods include secreting the G-CSF proteins into the E. coli periplasmic using the stII signal sequence, denaturing and refolding the insoluble or aggregated G-CSF proteins, and purifying the soluble, refolded G-CSF proteins from other proteins in the soluble fraction of the renaturation/refold mixture. The recovered G-CSF proteins lack the non-natural N-terminal methionine residue present when G-CSF proteins are expressed intracellularly in E. coli. Published reports (Perez-Perez et al., 1995) describe secretion of G-CSF into the E. coli periplasmic using a modified ompA leader sequence. However, very little of the expressed ompA-G-CSF fusion protein was properly processed to yield mature G-CSF. The percentage of properly processed G-CSF proteins could be increased to 10-30% of total expressed G-CSF proteins by co-expression of the E. coli dnaJ and dnaK proteins. In all cases, the secreted G-CSF proteins were largely insoluble and biologically inactive. The methods of the present invention yield at least 80-100% properly processed G-CSF proteins and do not require co-expression of the dnaK and dnaJ proteins. The present invention also provides, for the first time, methods for denaturing and refolding the insoluble, secreted G-CSF proteins into a biologically active form.

The purified proteins obtained according to these methods can be further processed if desired. For example, the isolated proteins can be modified at the free cysteine residue with various cysteine-reactive moieties. For example, the proteins can be PEGylated at the free cysteine residue with various cysteine-reactive PEG reagents, and subsequently purified as monoPEGylated proteins. The term "monoPEGylated" is defined to mean a protein modified by covalent attachment of a single PEG molecule to the protein. Any method known to those skilled in the art can be used to purify the PEGylated protein from unmodified protein and unreacted PEG reagents, including, for example, the methods described in the Examples below, and in PCT/US98/14497 and PCT/US00/00931. Examples of other useful cysteine-reactive moieties are cysteine-reactive dextrans, cysteine-reactive carbohydrates and cysteine-reactive poly(N-vinylpyrrolidone)s.

The present invention also provides methods for PEGylating cysteine muteins of GH, G-CSF, GM-CSF, alpha interferon and other proteins containing 2N+1 cysteine residues, and other proteins containing 2N cysteine residues where two or more of the cysteine residues are free, particularly those muteins and proteins in which the free cysteine residue is blocked by a mixed disulfide.

The present invention further relates to purified, monoPEGylated protein variants produced by the methods disclosed herein that are not only biologically active, but also retain high specific activity in protein-dependent mammalian cell proliferation assays. Such protein variants include, for example, purified, monoPEGylated cysteine muteins of G-CSF, GH, GM-CSF and IFN-α2. For example, the in vitro biological activities of certain of the monoPEGylated G-CSF variants described herein are 3- to 50-fold greater than the biological activity of G-CSF that has been PEGylated using amine-reactive NHS-PEG reagents.

There are over 25 distinct IFN-α genes (Pestka et al., 1987). Members of the IFN-α family share varying degrees of amino acid homology and exhibit overlapping sets of biological activities. Non-natural recombinant IFN-αs, created through joining together regions of different IFN-α proteins are in various stages of clinical development (Horisberger and DiMarco, 1995). A non-natural "consensus" interferon (Blatt et al., 1996), which incorporates the most common amino acid at each position of IFN-α, also has been described. The methods of the present invention also are useful for refolding other alpha interferon species and non-natural alpha interferon proteins containing a free cysteine residue. Useful sites and regions for PEGylating cysteine muteins of IFN-α2 are directly applicable to other members of the IFN-α gene family and to non-natural IFN-αs. Kinstler et al. (1996) described monoPEGylated consensus interferon in which the protein is preferentially mono PEGylated at the N-terminal, non-natural methionine residue through amine or amide linkages. Bioactivity of the PEGylated protein was reduced approximately 5-fold relative to non-modified consensus interferon (Kinstler et al., 1996).

In one embodiment of the monoPEGylated G-CSF, the polyethylene glycol is attached to the region proximal to Helix A of G-CSF and the resulting monoPEGylated G-CSF has an $EC_{50}$ less than about 1000 pg/ml (approximately 50 pM), preferably less than about 100 pg/ml (approximately 5 pM), more preferably less than about 20 pg/ml (approximately 1 pM) and most preferably less than about about 15 pg/ml (approximately 0.7 pM). Alternatively, the polyethylene glycol moiety can be attached to the C-D loop of G-CSF and the resulting monoPEGylated G-CSF has an $EC_{50}$ less than about 1000 pg/ml (approximately 50 pM), preferably less than about 100 pg/ml (approximately 5 pM), more preferably less than about 20 pg/ml (approximately 1 pM) and most preferably less than about 15 pg/ml (approximately 0.7 pM). Alternatively, the polyethylene glycol moiety can be attached to the region distal to Helix D of G-CSF and the resulting monoPEGylated G-CSF has an $EC_{50}$ less than about 1000 pg/ml (approximately 50 pM), preferably less than about 100 pg/ml (approximately 5 pM), more preferably less than about 20 pg/ml (approximately 1 pM) and most preferably about 15 pg/ml (approximately 0.7 pM). Kinstler et al., (1996) described monoPEGylated wild type G-CSF in which the protein is preferentially monoPEGylated at the N-terminal, non-natural methionine residue through amine or amide linkages. Bioactivity of the monoPEGylated G-CSF protein was reported to be reduced approximately 30% relative to non-modified G-CSF, although $EC_{50}$s were not provided (Kinstler et al., 1996). Kinstler et al. (1996) did not determine whether modifying other amino acids in the region proximal to helix A in G-CSF with PEG resulted in biologically active G-CSF proteins. One purpose of the present invention is to disclose other amino acid positions in the region proximal to Helix A, and other regions, in G-CSF where PEG can be attached, resulting in biologically active, monoPEGylated G-CSF proteins.

In one embodiment of the monoPEGylated GM-CSF, the polyethylene glycol is attached to the region proximal to Helix A of GM-CSF and the resulting monoPEGylated GM-CSF has an $EC_{50}$ less than about 14000 pg/ml (approximately 1000 pM), preferably less than about 1400 pg/ml (approximately 100 pM), more preferably less than about 280 pg/ml (approximately $^2$0 pM) and most preferably less than about 140 pg/ml (approximately 10 pM)). Alternatively, the polyethylene glycol moiety can be attached to the B-C loop of GM-CSF and the resulting monoPEGylated GM-CSF has an $EC_{50}$ less than about 14000 pg/ml (approximately 1000 pM), preferably less than about 1400 pg/ml (approximately 100 pM), more preferably less than about 280 pg/ml (approximately 20 pM) and most preferably less than about 140 pg/ml (approximately 10 pM)). Alternatively, the polyethylene glycol moiety can be attached to the C-D loop of GM-CSF and the resulting monoPEGylated GM-CSF has an $EC_{50}$ less than about 14000 pg/ml (approximately 1000 pM), preferably less than about 1400 pg/ml (approximately 100 pM), more preferably less than about 280 pg/ml (approximately 20 pM) and most preferably less than about 140 pg/ml (approximately 10 pM).

In one embodiment of the monoPEGylated GH, the polyethylene glycol is attached to the region proximal to Helix A of GH and the resulting monoPEGylated GH has an $EC_{50}$ less than about 2000 ng/ml (approximately 100 nM), preferably less than about 200 ng/ml (approximately 10 nM), more preferably less than about 20 ng/ml (approximately 1 nM) and most preferably less than about 2 ng/ml (approximately 0.1 nM).

The present invention further provides protein variants that can be covalently attached or conjugated to each other or to a chemical group to produce higher order multimers, such as dimers, trimers and tetramers. Such higher order multimers can be produced according to methods known to those skilled in the art or as described in Examples 2 and 20. For example, such a conjugation can produce a GH, G-CSF, GM-CSF or alpha IFN adduct having a greater molecular weight than the corresponding native protein. Chemical groups suitable for coupling are preferably non-toxic and non-immunogenic. These chemical groups would include carbohydrates or polymers such as polyols.

The "PEG moiety" useful for attaching to the cysteine variants of the present invention to form "PEGylated" proteins include any suitable polymer, for example, a linear or branched chained polyol. A preferred polyol is polyethylene glycol, which is a synthetic polymer composed of ethylene oxide units. The ethylene oxide units can vary such that PEGylated-protein variants can be obtained with apparent molecular weights by size-exclusion chromatography ranging from approximately 10,000 to greater than 500,000 kDa. The size of the PEG moiety directly impacts its circulating half-life (Yamaoka et al., 1994). Accordingly, one could engineer protein variants with differing circulating half-lives for specific therapeutic applications or preferred dosing regimes by varying the size or structure of the PEG moiety. Thus, the present invention encompasses GH protein variants having an apparent molecular weight greater than about 30 kDa, and more preferably greater than about 70 kDa as determined by size exclusion chromatography, with an $EC_{50}$ less than about 400 ng/ml (18 nM), preferably less than 100 ng/ml (5 nM), more preferably less than about 10 ng/ml (0.5 nM), and even more preferably less than about 2.2 ng/ml (0.1 nM). The present invention further encompasses G-CSF protein variants having an apparent molecular weight greater than about 30 kDa, and more preferably greater than about 70 kDa as determined by size exclusion chromatography, with an $EC_{50}$ less than about 100 ng/ml (5 nM), preferably less than 1000 pg/ml (50 pM), more preferably less than 100 pg/ml (6 pM), and even more preferably less than about 15 pg/ml (0.7 pM). The present invention further encompasses alpha IFN (IFN-α) protein variants having an apparent molecular weight greater than about 30 kDa, and more preferably greater than about 70 kDa as determined by size exclusion chromatography, with an $EC_{50}$ less than about 1400 pg/ml (~1000 pM), preferably less than 1400 pg/ml (~100 pM), more preferably less than 280 pg/ml (20 pM), and even more preferably less than about 140 pg/ml (~1 pM).

The reactive PEG end group for cysteine modification includes but is not limited to vinylsulfone, maleimide and iodoacetyl moieties. The PEG end group should be specific for thiols with the reaction occurring under conditions that are not detrimental to the protein.

Antagonist hGH variants also can be prepared using a cysteine-added variant GH as described in PCT/US98/14497 and PCT/US00/00931. Conditions that would benefit from the administration of a GH antagonist include acromegaly, vascular eye diseases, diabetic nephropathy, restenosis following angioplasty and growth hormone responsive malignancies.

As used herein, the term "derivative" refers to any variant of a protein expressed and recovered by the present methods. Such variants include, but are not limited to, PEGylated versions, dimers and other higher order variants, amino acid variants, truncated variants, fusion proteins, changes in carbohydrate, phosphorylation or other attached groups found on natural proteins, and any other variants disclosed herein.

The compounds produced by the present methods can be used for a variety of in vitro and in vivo uses. The proteins and their derivatives of the present invention can be used for research, diagnostic or therapeutic purposes that are known for their wildtype, natural, or previously known modified counterparts. In vitro uses include, for example, the use of the protein for screening, detecting and/or purifying other proteins.

For therapeutic uses, one skilled in the art can readily determine the appropriate dose, frequency of dosing and route of administration. Factors in making such determinations include, without limitation, the nature of the protein to be administered, the condition to be treated, potential patient compliance, the age and weight of the patient, and the like. The compounds of the present invention can also be used as delivery vehicles for enhancement of the circulating half-life of the therapeutics that are attached or for directing delivery to a specific target within the body.

The following examples are not intended to be limiting, but only exemplary of specific embodiments of the invention.

EXAMPLES

Example 1

Refolding of the Growth Hormone Mutein T3C

Methods for expressing, purifying and determining the in vitro and in vivo biological activity of recombinant human Growth Hormone (hGH) and hGH cysteine muteins are described in PCT/US98/14497 and PCT/US/00/00931. Methods for constructing cysteine muteins of hGH also are described in PCT/US98/14497 and PCT/US/00/00931. One preferred method for expressing hGH in *E. coli* is to secrete the protein into the periplasmic using the STII leader sequence. Secreted hGH is soluble and can be purified by column chromatography as described in PCT/US00/00931. Certain cysteine muteins of hGH remain insoluble when secreted into the *E. coli* periplasmic using the STII leader sequence. Procedures for refolding insoluble, secreted hGH proteins have not been described previously. The following protocols were developed to refold insoluble hGH cysteine muteins into a biologically active form.

The insoluble GH T3C mutein (threonine at position 3 changed to cysteine; described in PCT/US98/14497 and PCT/US/00/00931) was expressed in *E. coli* as a protein secreted to the periplasmic space using the stII leader sequence as described in PCT/US00/00931. The T3C protein was solubilized and refolded using the following two procedures, both of which use cysteine as a reducing agent and as a cysteine blocking agent to stabilize the free cysteine residue. Cultures (200 ml) of an *E. coli* strain expressing the T3C mutein were grown and expression of T3C was induced as described in PCT/US00/00931. The cells were lysed and the insoluble portion was isolated by centrifugation as described in Example 14. The insoluble material containing T3C was dissolved in 20 mL of 8 M urea, 20 mM cysteine, 20 mM Tris pH 9 and mixed by shaking for 1 hour at room temperature. The solubilization mixture was next divided into two, with half being diluted into 50 mL of 10% glycerol, 20 mM Tris, pH 8 and the other half being diluted into 50 mL of 0.5% TWEEN 20, 20 mM Tris, pH 8. The refolds were held at 4° C. for 24 hours before being clarified by centrifugation and loaded onto a 5 mL Q-Sepharose Hi Trap column previously equilibrated in 20 mM Tris, 0.5% Tween 20, pH 7.6. Refolded, soluble T3C was eluted from the column during a 20 column volume gradient of 0-300 mM NaCl in 0.5% Tween 20, 20 mM Tris pH 7.6. Recovered column fractions were analyzed by non-reducing SDS-PAGE. Monomeric T3C eluted at around 160 mM NaCl. Approximately 790 µg of monomeric T3C were recovered from the refold containing glycerol in the renaturation buffer. Approximately 284 µg of monomeric T3C was recovered from the refold when Tween 20 was present in the renaturation buffer. The results indicate that soluble, monomeric T3C protein can be obtained using either refold/renaturation procedure. Based on the greater recovery yields of monomeric T3C protein, glycerol was used as a stabilizing agent in subsequent refold experiments.

Example 2

Comparison of Reducing Agents Used to Refold the Growth Hormone T3C Mutein

Cultures (200 mL) of an *E. coli* strain expressing the T3C mutein were grown and T3C expressed as described in PCT/US00/00931. Insoluble T3C was isolated by lysing the cells with detergent/lysozyme treatment of the cells as described in Examples 5 and 14. This material was suspended in 20 mL of 8 M urea, 20 mM Tris pH 9 and aliquoted into 3 tubes. No reducing agent was added to the first tube ("Refold A"), 5 mM DTT was added to the second tube ("Refold B") and 20 mM cysteine was added to the third tube ("Refold C"). After one hour of mixing at room temperature, the solubilizations were diluted into 30 mL of 10% glycerol, 20 mM Tris, pH 8. The refolds were held at 4° C. overnight The next day, the refolds were clarified by centrifugation and loaded onto 5 mL Q-Sepharose Hi Trap columns as described in PCT/US00/00931. Recovered fractions were analyzed by non-reducing SDS-PAGE. The T3C protein recovered from "Refold A" (no reducing agent) eluted as several broad peaks from the Q-Sepharose column. By SDS-PAGE, the recovered protein product had some monomeric T3C protein present, but consisted mostly of aggregated T3C dimers (eluting at 210 mM NaCl) and T3C multimers (eluting between 300 nM to 1000 mM NaCl). Final recoveries of monomeric and dimeric T3C proteins are shown in Table 1. The T3C protein recovered from "Refold B" (with 5 mM DTT) eluted as a single broad peak from the Q-Sepharose column, but was heterogeneous by non-reducing SDS-PAGE analysis. The monomeric T3C band was much broader than the pituitary hGH band and comprised a number of different molecular weight, monomeric species, which probably represent different disulfide isoforms of T3C. A small amount of dimeric T3C protein was also detected in several of the fractions. "Refold C" (with cysteine as the reducing agent) yielded mainly monomeric T3C protein, which appeared to be a single homogeneous species, as evidenced by the sharpness of the peak eluting from the Q-Sepharose column at 160 mM NaCl and by the sharpness of the protein band at the correct molecular weight (relative to the standard pituitary hGH) when analyzed by non-reducing SDS PAGE. Final recoveries of monomeric and dimeric forms of T3C from each of the refolds are given in Table 1. The data indicate that solubilizing/refolding the T3C protein in the presence of cysteine results in greater yields of soluble monomeric T3C protein than does solubilizing/refolding the protein in the absence of a reducing agent or in the presence of DTT. The results also indicate that solubilizing/refolding the T3C protein in the presence of cysteine yields a more stable, homogeneous preparation of soluble, monomeric T3C protein than does solubilizing/refolding the protein in the absence of a reducing agent or in the presence of DTT.

TABLE 1

Recoveries of T3C Proteins Prepared Using Various Refold Procedures

| Refold | Reducing Agent | Monomeric T3C protein Yield (µg)[a] | Dimeric T3C protein Yield (µg)[a] |
|---|---|---|---|
| A | none | 30 | 120 |
| B | 5 mM DTT | 370 | 25 |
| C | 20 mM Cysteine | 534 | 225 |

[a]Protein recovered per 66 ml of *E. coli* culture

The monomeric T3C protein recovered from the Refold B, which contained DTT in the solubilization mixture, can be converted to stable, disulfide-linked homodimeric T3C protein by placing the protein under conditions that allow for disulfide bond formation. These include conditions where an oxidizing agent is added to the protein, or by the addition of a second disulfide-linked reagent that is capable of undergoing a disulfide rearrangements when the pH is near neutral or alkali. Examples of oxidizing agents that could be used include sodium tetrathionate or oxygen. Optionally, trace amounts of divalent metal ions such as copper or cobalt can be added to catalyze the reaction. Useful disulfide-linked reagents include cystine, cystamine, oxidized glutathione, dithioglycolate, or other low molecular weight dithiols. Alternatively, monomeric T3C protein can be held at an acidic pH to prevent aggregation and unwanted disulfide rearrangements.

The soluble, refolded GH cysteine muteins prepared according to the procedures described in Examples 1 and 2 can be purified by various chromatography procedures known to those of skill in the art. These chromatographic procedures include ion exchange, size exclusion, hydrophobic interaction (HIC), metal chelation affinity chromatographies (IMAC), Size Exclusion Chromatography (SEC), Reversed Phase chromatography or a combination of these techniques. As one example, the GH muteins can be captured from the soluble fraction of the refold mixture using a Q-Sepharose fast flow resin (Pharmacia) equilibrated in 20 mM Tris-HCl, pH 8.0. The column can be washed with 20 mM Tris-HCl, pH 8.0 and bound proteins eluted with a linear 10-20 volume increasing salt gradient from 0 to 250 mM NaCl in 20 mM Tris-HCl, pH 8.0. Optionally, Glycerol (10% final concentration) can be added to the column buffers. Fractions containing the hGH muteins can be identified by SDS-PAGE and Western blotting. Alternative resins that can be used to capture hGH muteins from the soluble fraction of the refold/renaturation mixture include HIC, other ion exchange resins or affinity resins.

The cysteine muteins can be purified further by hydrophobic interaction chromatography. Q-Sepharose column fractions containing the GH muteins can be pooled and NaCl added to a final concentration of 2 M. The pool can be loaded onto a Butyl-Sepharose fast flow resin previously equilibrated in 2 M NaCl, 20 mM sodium phosphate, pH 7.5. GH muteins can be eluted from the resin using a reverse salt gradient from 2 M to 0 M NaCl in 20 mM phosphate, pH 7.5. Fractions containing the GH muteins can be identified by SDS-PAGE and Western blotting, and pooled. Alternatively the Q-sepharose fractions containing the GH muteines can be pooled and ammonium sulfate added to a final concentration of 2 M before being loaded onto a Phenyl-Sepharose column. The GH muteins can be eluted from the resin using a reverse salt gradient from 2 M to 0 M ammonium sulfate in 20 mM sodium phosphate, pH 7.5. Fractions containing the GH muteins can be identified by SDS-PAGE and Western blotting, and pooled.

If further purification is desired, the HIC pool containing the GH muteins can be loaded directly onto a nickel chelating resin (Qiagen) equilibrated in 10 mM sodium phosphate, 0.5 M NaCl, pH 7.5. Following a wash step, the GH muteins can be recovered using a 0-30 mM imidizole gradient in 10 mM sodium phosphate, 0.5 M NaCl, pH 7.5. GH has a high affinity for nickel, presumably through the divalent metal-binding site formed by H18, H21 and E174. As a result, GH can be obtained in highly pure form using a metal chelation column (Maisano et al., 1989). The GH muteins will bind tightly to the nickel column and elute at similar imidazole concentrations (around 15 mM) as wild-type GH. Alternatively a copper chelating column may be used in place of a nickel chelating column.

Biological activities of the purified GH cysteine muteins can be measured using the cell proliferation assay described in PCT/US00/00931. Protein concentrations can be determined using a Bradford dye binding assay (Bio-Rad Laboratories).

The T3C mutein was purified as follows. A 600 mL culture of *E. coli* was grown and T3C protein expression induced as described above. Insoluble T3C was isolated by treating the cells with a detergent/lysozyme mixture (B-Per™, Pierce) as described in Examples 5 and 14. The insoluble material was suspended in 40 mL of 8 M urea, 20 mM Tris, 20 mM Cysteine, pH 9. After one hour of mixing at room temperature, the solubilization mixture was diluted into 200 mL of 15% glycerol, 20 mM Tris, pH 8, 40 µM copper sulfate. The refold was held at 4° C. overnight. The next day, the refold was clarified by centrifugation and loaded onto a 5 mL Q-Sepharose Hi Trap column equilibrated in 10% glycerol, 20 mM Tris, pH 8. T3C was recovered by elution with a 20 column volume gradient from 0-250 mM NaCl in 20 mM Tris, pH 8, 10% glycerol. Recovered fractions were analyzed by non-reducing SDS-PAGE. Fractions containing predominantly T3C protein of the correct apparent molecular weight were pooled. Pooled fractions yielded 4.6 mg of purified T3C protein. This material was used for the PEGylation studies described in Example 3. Biological activity of the purified T3C protein was measured in the GH-R4 cell proliferation assay described in Examples 1 and 2 and PCT/US98/14497 and PCT/US0O/00931. The T3C protein stimulated proliferation of the GH-R4 cells with an $EC_{50}$ of 1.35 ng/ml.

Other cysteine muteins of GH that were prepared by this procedure include *-1C, P2C, P5C, K38C, Q40C, K41C, S55C, S57C, T60C, Q69C, N72C, N99C, L101C, V102C, Y103C, D130C, S132C, P133C, R134C, T135C, Q137C, K140C, Q141C, T142C, Y143C, K145C, D147C, N149C, S150C, H151C, N152C, D153C, E186C, and G187C. Biological activities of certain of the purified GH cysteine muteins were measured in the GH-R4 cell proliferation assay described in PCT/US00/00931. The observed $EC_{50}$s for muteins *-1C, P2C, P5C, K38C, Q40C, S55C, N99C, L101C, V102C, Y103C, P133C, Q137C, K140C, Y143C, D147C, N149C, E186C, and G87C ranged from 0.7 ng/ml to 2.2 ng/ml. These values are all nearly equivalent to the observed $EC_{50}$s for wild type GH controls in these assays which ranged from 0.3 ng/ml to 1.5 ng/ml.

Example 3

General Methods for PEGylation and Purifying PEGylated Forms of Proteins Containing Free Cysteine Residues Proteins containing free cysteine residues can be PEGylated using a variety of cysteine-reactive PEG-maleimide (or PEG-vinylsulfone) reagents that are commercially available. The recombinant proteins are generally partially reduced with dithiothreitol (DTT), Tris (2-carboxyethyl) phosphine-HCl (TCEP) or some other reducing agent in order to achieve optimal PEGylation of the free cysteine. The free cysteine is relatively unreactive to cysteine-reactive PEGs unless this partial reduction step is performed. The amount of reducing agent required to partially reduce each mutein can be determined empirically, using a range of reducing agent concentrations at different pHs and temperatures. Reducing agent concentrations typically vary from 0.5 equal molar to 10-fold molar excess. Preferred temperatures are 4° C. to 37° C. The pH can range from 6.5 to 9.0 but is preferably 7.5 to 8.5. The optimum conditions will also vary depending on the reductant and time of exposure. Under the proper conditions, the least stable disulfides (typically intermolecular disulfides and mixed disulfides) are disrupted first rather than the more thermodynamically stable native disulfides. Typically, a 5-10 fold molar excess of DTT for 30 minutes at room temperature is effective. Partial reduction can be detected by a slight shift in the elution profile of the protein from a reversed-phase column Partial reduction also can be detected by a slight shift in apparent molecular weight by non-reducing SDS-PAGE analysis of the protein sample. Care must be taken not to "over-reduce" the protein and expose additional cysteine residues. Over-reduction can be detected by reversed phase-HPLC (the over-reduced protein will have a retention time similar to the fully reduced and denatured protein) and by the appearance of protein molecules containing two PEGs following the PEGylation reaction (detectable by an apparent molecular weight change on SDS-PAGE). In the case of cysteine muteins, the corresponding wild type protein can serve as a control since it should not PEGylate under conditions that do not reduce the native intramolecular disulfides. Excess reducing agent can be removed prior to PEGylation by size exclusion chromatography or by dialysis. TCEP need not be removed before addition of the PEGylation reagent as it is does not contain a free thiol group. The partially reduced protein can be reacted with various concentrations of PEG-maleimide or PEG-vinylsulfone (typically PEG: protein molar ratios of 1:1, 5:1,10:1 and 50:1) to determine the optimum ratio of the two reagents. PEGylation of the protein can be monitored by a molecular weight shift for example, using SDS-PAGE. The lowest amount of PEG that gives significant quantities of mono-pegylated product without giving di-pegylated product is typically considered desirable. In some instances, certain additives can enhance the PEGylation yield. These additives include, but are not limited to, EDTA, borate, chaotropes (urea, guanidine, organic solvents), detergents, osmolytic stabilizers (polyols, sugars, polymers, amino acids and derivatives thereof), and other ionic compounds (citrate, sulfates, phosphates, quaternary amines, chlorides nitrates, thiocyanates, etc.) Useful concentrations of EDTA are 0.01-10 mM, with 0.5-1 mM being preferred concentrations. Generally, mono-PEGylated protein can be purified from non-PEGylated protein and unreacted PEG by size-exclusion, ion exchange, affinity, reversed phase, or hydrophobic interaction chromatography. Fractions enriched for the mono-PEGylated protein (a single PEG molecule attached to the cysteine mutein) can be identified by SDS-PAGE and/or Western blotting. These fractions can be pooled and stored frozen. The presence of the PEG moiety generally alters the protein's affinity for the resin, allowing the PEGylated protein to be separated from the non-PEGylated protein. Other purification protocols such as 2-phase organic extraction or salt precipitation also can be used. The purified, PEGylated protein can be tested in the cell proliferation/inhibition assays described in the various Examples described herein and in PCT/US98/14497 and PCT/US00/00931 to determine its specific activity. In vivo efficacy of the PEGylated proteins can be determined as described in the Examples provided herein and in PCT/US98/14497 and PCT/US00/00931. Experiments can be performed to confirm that the PEG molecule is attached to the protein at the proper site. This can be accomplished by chemical or proteolytic digestion of the protein, purification of the PEGylated peptide (which will have a large molecular weight) by size exclusion, ion exchange or reversed phase chromatography, followed by amino acid sequencing. The PEG-coupled amino acid will appear as a blank in the amino acid sequencing run.

The following conditions were used to PEGylate the GH mutein T3C and to purify the PEGylated T3C protein. Initial PEGylation reactions conditions were determined using aliquots of the refolded T3C protein prepared as described in Example 2 (using cysteine as the reducing agent and as the cysteine blocking agent to solubilize and refold the protein), TCEP [Tris (2-carboxyethyl) phosphine]-HCl as the reducing agent and 5 kDa cysteine reactive PEGs from Shearwater Polymers (Huntsville, Ala.). Two µg aliquots of purified T3 C were incubated with increasing concentrations of TCEP at room temperature in 100 mM Tris, pH 8.5 in the presence of varying amounts of excess 5 kDa maleimide-PEG or 5 kDa vinylsulfone-PEG. After 120 minutes, aliquots of the reactions were immediately analyzed by non-reducing SDS-PAGE. At pH 8.5, a 5-fold molar excess of TCEP and 15-fold excess molar of either 5 kDa maleimide or 5 kDa vinyl sulfone PEG yielded significant amounts of monoPEGylated T3C protein after two hours without detectable di or tri-PEGylated protein. The T3C mutein needed to be partially reduced by treatment with a reductant such as TCEP in order to be PEGylated. Wild type GH did not PEGylate under identical partial reducing conditions, indicating that the PEG moiety is attached to the cysteine residue introduced into the mutein. These conditions were used to scale up the PEGylation reaction for purification and evaluation of biological activity. A larger PEGylation reaction (300 µg) was performed for 2 hr at room temperature, using a 5-fold excess of TCEP and 15-fold of 10 kDa maleimide PEG. At the end of the reaction time, the PEGylation mixture was diluted 2× with ice cold 20 mM Tris, 15% glycerol, pH 8.0 and immediately loaded onto a Q-Sepharose column (1 mL, HiTrap). PEGylated T3C was eluted from the column by running a 20 mL gradient from 0-0.2 M NaCl in 20 mM Tris, 15% glycerol, pH 8. The presence of the PEG moiety decreases the protein's affinity for the resin, allowing the PEGylated protein to be separated from the non-PEGylated protein. Fractions enriched for mono-PEGylated T3C (a single PEG molecule attached to the T3C monomer) were identified by SDS-PAGE, pooled and frozen. The mono-PEGylated T3C protein eluted at approximately 80 mM NaCl and its apparent molecular weight by SDS-PAGE was approximately 30 kDa.

10K PEG-T3C, 20K PEG-T3C, and 40 K PEG-T3C were also prepared by the method described above. Bioactivity of the purified PEG-T3C proteins were measured in the cell proliferation assay described in Examples 1 and 2 and PCT/US98/14497 and PCT/US/00/00931 to determine its specific activity. The PEG-T3C proteins stimulated proliferation of GH-R4 cells similar to wild type GH and non-PEGylated T3C protein. The $EC_{50}$ for the 5K PEG-T3C protein was 1.2 ng/ml, the $EC_{50}$ for the 10K PEG-T3C was 1.2 ng/ml, and the $EC_{50}$ for the 20K PEG-T3C was 34 ng/ml. The $EC_{50}$ for the 40K- PEG-T3C can be determined using the cell proliferation assay described in Examples 1 and 2 and PCT/US98/14497 and PCT/US/00/00931. In vivo efficacy of PEG-T3C and other PEGylated GH cysteine muteins can be determined as described in PCT/US98/14497 and PCT/US00/00931 and Example 4.

Other cysteine mutants of GH that were PEGylated and purified according to the procedures outlined above include P2C, P5C, S132C, P133C, and R134C. The biological activities of these muteins that were modified with 20 kDa-PEG moieties were measured using the cell proliferation assay described in Examples 1 and 2 and PCT/US98/14497 and PCT/US/00/00931. The observed $EC_{50}$s for these PEGylated muteins muteins ranged from 1.7 ng/ml to 6.0 ng/ml. These values are all similar to, but slightly greater than, the observed $EC_{50}$s for wild type GH control assays that were performed in parallel. The $EC_{50}$s for these wild type GH controls ranged from 0.6 ng/ml to 1.2 ng/ml.

Example 4

PEG-T3C Growth Hormone Stimulates Somatic Growth in Growth Hormone Deficient Rats A. The ability of PEG-T3C to stimulate somatic growth was determined in hypophysectomized (HYPOX) rats, which are unable to synthesize growth hormone due to removal of their pituitaries. HYPOX male Sprague-Dawley rats were purchased from a commercial vendor and weighed about 90 g. The rats were acclimated for 13 days. Animals gaining more than 4 g during acclimation were culled from the study. Body weight measurements were taken at the same time every day (9:30 AM). Rats were randomized by weight to the various test groups. There were 5 rats per group except for the group receiving every day doses of 20 kDa-PEG-T3C, in which there were only four rats. Rats were weighed daily and were given daily or every other day subcutaneous injections of placebo (Phosphate Buffered Saline (PBS) containing 200 µg/ml rat serum albumin (Sigma Chemical Company)), a commercial recombinant human growth hormone, Nutropin®, or various doses of 20 kDa-PEG-T3C prepared as described in Example 3. All protein solutions were prepared in PBS containing 200 µg/ml rat serum albumin. Animals were treated for 9 consecutive days. On day 10, the animals were sacrificed and their tibias were harvested. The tibias were fixed in 10% neutral buffered formalin The fixed tibias were decalcified in 5% formic acid and split at the proximal end in the frontal plane. The tibias were processed for paraffin embedding and sectioned at 8 microns and stained with toluidine blue. The width of the tibial physis was measured on the left tibia (5 measurements per tibia). Cumulative body weight gain and tibial epiphyses measurements for the different test groups are shown in Table 2. The results show that 20 kDa-PEG-T3C stimulates body weight gain and bone growth in growth hormone deficient rats.

tive days. On day 10, the animals were sacrificed and their tibias were harvested and prepared for sectioning as described in Example 4.A.

Cumulative body weight gain and tibia epiphyses widths for the different test groups are shown in Table 3.

TABLE 2

Effects of every day or every other day administration of placeb, Nutropin or 20 kDA-PEG-T3C on body weight gain and tibial epiphyses width in hypophysectomized rats

| Compound | Dose | Injection Frequency | Cumulative Body Weight Gain (grams) | Tibial Epiphyses Width (mean +/− SE) (μm) |
|---|---|---|---|---|
| Placebo | — | Every day | −1.0 +/− 0.707 | 206.8 +/− 9.2 |
| Nutropin | 10 μg/injection | Every day | 11.2 +/− 0.97$^a$ | 348.8 +/− 8.6$^a$ |
| 20 kDa-PEG-T3C | 10 μg/injection | Every day | 14.3 +/− 0.75$^a$ | 333.0 +/− 9.8$^a$ |
| Placebo | — | Every other day | 0.6 +/− 1.03 | 204.4 +/− 8.6 |
| Nutropin | 10 μg/injection | Every other day | 8.6 +/− 1.12$^b$ | 298.8 +/− 10.1$^b$ |
| 20 kDa-PEG-T3C | 10 μg/injection | Every other day | 15.4 +/− 0.68 b$^{a,c}$ | 357.2 +/− 7.7$^b$ |
| 20 kDa-PEG-T3C | 2 μg/injection | Every other day | 5.6 +/− 0.51$^b$ | 274.8 +/− 9.0$^b$ |
| 20 kDa-PEG-T3C | 0.4 μg/injection | Every other day | −0.2 +/− 0.66 | 225.2 +/− 10.0$^b$ |

$^a$p<0.05 versus every day placebo using a two-tailed T test
$^b$p<0.05 versus every other day placebo using a two-tailed T test
$^c$p<0.05 versus every other day Nutropin using a two-tailed T test B. A second experiment was performed as described for Example 4.A. except that the test compounds were administered by subcutaneous injection every day or every third day. In addition, one dose of T3C modified with a 40 kDa-PEG was tested. HYPOX male Sprague-Dawley rats were purchased from a commercial vendor and weighed about 100 g. Body weight measurements were taken at the same time every day. Rats were randomized by weight to the various test groups. There were 5 rats per group except for the group, except for the test group receiving 40 kDa-PEG-T3C. Rats were weighed daily and were given daily or every third day subcutaneous injections of placebo (Phosphate Buffered Saline (PBS) containing 200 μg/ml rat serum albumin (Sigma Chemical Company)), a commercial recombinant human growth hormone, Nutropin®, various doses of 20 kDa-PEG-T3C or 40 kDa-PEG-T3C. The PEG-T3C proteins were prepared as described in Example 3. All protein solutions were prepared in PBS containing 200 μg/1 ml rat serum albumin. Animals were treated for 9 consecu- The results show that 20 kDa-PEG-T3C and 40 kDa-PEG-T3C stimulate body weight gain and bone growth in growth hormone deficient rats.

TABLE 3

Effects of every day or every third day administration of placebo, Nutropin, 20 kDA-PEG-T3C or 40 kDa-PEG-T3C on body weight gain and tibial epiphyses width in hypophysectomized rats

| Compound | Dose | Injection Frequence | Cumulative Body Weight Gain (grams) | Tibial Epiphyses Width (mean +/− SE) (μm) |
|---|---|---|---|---|
| Placebo | — | Every Day | 0.8 +/− 0.685 | 223 +/− 15.1 |
| Nutropin | 30 μg/injection | Every day | 21.3 +/− 1.432 | 408.4 +/− 14.2 |
| Nutropin | 10 μg/injection | Every Day | 16.2 +/− 1.232 | 399.6 +/− 15.6 |
| 20 kDa-PEG-T3C | 10 μg/injection | Every Day | 18.6 +/− 2.215 | 384.4 +/− 13.0 |
| Placebo | — | Every third day | 1.5 +/− 1.370 | 231.6 +/− 17.4 |
| Nutropin | 30 μg/injection | Every third day | 6.8 +/− 1.385 | 315.2 +/− 15.6 |
| Nutropin | 10 μg/injection | Every third day | 8.0 +/− 1.614 | 284.0 +/− 6.9 |
| 20 kDa-PEG-T3C | 30 μg/injection | Every third day | 17.5 +/− 1.162 | 428.4 +/− 18.3 |
| 20 kDa-PEG-T3C | 10 μg/injection | Every third day | 12.3 +/− 0.792 | 329.2 +/− 15.6 |
| 20 kDa-PEG-T3C | 2 μg/injection | Every third day | 8.0 +/− 1.379 | 263.2 +/− 7.1 |
| 40 kDa-PEG-T3C | 10 μg/injection | Every third day | 17.2 +/− 0.868 | 360.5 +/− 21.9 |

Example 5

Refolding and Purification of IFN-α2 Cysteine Muteins

Methods for expressing, purifying and determining the in vitro and in vivo biological activity of recombinant human alpha interferon 2 (IFN-α2) and IFN-α2 cysteine muteins are described in PCT/US00/00931. Methods for constructing cysteine muteins of IFN-α2 and preferred sites within the IFN-α2 protein for the locations of added cysteine residues also are described in PCT/US98/14497 and PCT/US00/00931. The following muteins have been constructed in E coli using those methods: C1S, Q5C, 43C44, N45C, Q46C, F47C, Q48C, A50C, D77C, C98S, Q101C, T106C, E107C, T108C, S163C, E165C, *166C, D2C, L3C, T6C, S8C, T52C, G102C, V103C, G104C, V105C, P109C, L110C, M111C, S160C, L161C, R162C and K164C. One preferred method for expressing IFN-α2 in *E. coli* is to secret the protein into the periplasmic using the STII leader sequence. A fraction of the secreted IFN-α2 is soluble and can be purified by column chromatography as described in PCT/US00/00931. Certain cysteine muteins of IFN-α2 remain insoluble when secreted into the *E. coli* periplasmic using the STII leader sequence. SDS-PAGE analysis of the osmotic shock supernatants of the muteins showed most to have reduced (as compared to wild type) levels of the 19 kDa rIFN-α2 band. SDS-PAGE analyses of whole cell lysates and the insoluble material from the osmotic shocks revealed that these muteins were expressed at relatively high levels but accumulated primarily in an insoluble form, presumably in the periplasmic. These proteins comigrated with wild type rIFN-α2 standards under reducing conditions indicating that the STII leader had been removed. Qualitative assessments of relative expression levels of the muteins are summarized in Table 4. Procedures for refolding insoluble, secreted IFN-α2 proteins have not been described previously. The following protocol (here referred to as "Protocol I") was developed to express and refold IFN-α2 cysteine muteins into a biologically active form.

For expression of IFN-α2 cysteine muteins and IFN-α2, typically, a 325 ml culture in a 2 liter shake flask, or a 500 ml culture in a 2 liter baffled shake flask, were grown at 37° C. in a gyrotory shaker water bath at ~170-220 rpm. Cultures were grown, induced, harvested, and subjected to osmotic shock as described in PCT/US00/00931. Resulting supernatants and pellets were processed immediately or stored at −80° C.

IFN-α2 cysteine muteins that were recovered as insoluble proteins in the osmotic shock pellets were denatured, reduced and refolded into their proper conformations using the following refold procedure. The pellet from the osmotic shock lysate was first treated with B-PER™ bacterial protein extraction reagent as described by the manufacturer (Pierce). B-PER is a mild detergent mixture that disrupts the *E. coli* membranes and releases the cytoplasmic contents of the cells. Insoluble material was recovered by centrifugation, resuspended in water, and recentrifuged. The resulting pellet was solubilized in 5 mL of 6 M guanidine, 50 mM cysteine in 20 mM Tris Base. The mixture was allowed to stir for 30 minutes before being dialyzed overnight at 4° C. against 400 mL of 40 mM sodium phosphate, 150 mM NaCl, pH 8.0. The next day the pH of the refold mixture was adjusted to 3.0 and the mixture was centrifuged before being loaded onto an S-Sepharose column, followed by a Cu++ IMAC column as described for the purification of rIFN-α2 from the osmotic shock supernatant in PCT/US00/00931. Six IFN-α2 cysteine muteins: Q5C, C98S, Q101C, T106C, E107C and *166C have been refolded and purified using these procedures. Similar procedures can be used to refold and purify insoluble wild type IFN-α2.

Non-reducing SDS-PAGE analysis of purified Q5C, C98S, Q101C, T106C, E107C, and *166C cysteine muteins showed that the muteins were recovered predominantly as monomers, migrating at the expected molecular weight of ~19 kDa. C98S migrated with a slightly higher molecular weight than the other rINF-α2 muteins due to the absence of the native Cys1-Cys-98 disulfide bond. Some of the purified muteins contained small amounts of disulfide-linked rIFN-α2 dimers. The molecular weights of the dimer species were approximately 37-38 kDa.

When processing a number of cyteine muteins of IFN-α2, it was discovered that certain cysteine muteins appeared to be present in both the soluble and insoluble fractions following cell lysis. Ratios of soluble verus insoluble IFN-α2 protein varied from mutant to mutant. Therefore, an alternative solubilzation/refolding procedure (here referred to as "Protocol II") that involves a whole cell solublization step was developed to enhance recovery of the IFN cysteine muteins. A modification of the culture methods was found to improve the efficiency of processing of the STII leader sequence and was employed to express IFN-α cysteine muteins for refolding and purification, as detailed below. In the modified method, 325-400 ml cultures were grown in LB media containing 100 mM MES, pH 5.0 and 100 μg/ml ampicillin at 37° C. with vigorous shaking, e.g., 220-250 rpm in a New Brunswick C25KC environmental shaker, to a cell density of 0.5-0.7 OD at 600 nm. Cultures were then induced by addition of IPTG (isopropyl-β-D-thiogalactopyranoside) to a final concentration of 0.5 mM and upon induction the temperature was reduced to 28° C. and the shaker speed was reduced to 140 rpm. Induced cultures were incubated overnight (14-18 hours) and harvested by centrifugation. Cell pellets were processed immediately or stored at −20° C. or −80° C. until processing. The cell pellets derived from a 325-400 mL induced culture are first suspended in 10 mL of 8 M Guanidine, 20 mM Cysteine, 20 mM Mes, 2% Tween 20, pH 3 and mixed until a homogeneous suspension is present The pH is then increased to between pH 8-9 and the solubilization mixture is stirred for 3 hours. The cell lysate is next diluted 1:20 with ice cold renaturation buffer (20 mM Tris, pH 0.3 M guanidine, 1 M urea, 40 μM copper sulfate, pH 8). The cloudy suspension is allowed to sit 1-2 days at 40° C. The refold is clarified by centrifugation followed by a pH adjustment to 3 and second round of centrifugation. The supernatant is diluted 1:4 with cold water and load onto a 5 mL S-Seph Hi Trap. The ion exchange column is eluted with a 100 mL gradient of 0-70% Buffer B, with Buffer A being 20 mM Mes, pH 5 and Buffer B being 10% Ethylene glycol 500 mM NaCl, 20 mM Mes pH 5. Alternatively, refolded IFN-α cysteine muteins can be captured from the refold mixture using a HIC column, such as a Phenyl-Sepharose column. The refold mixture is first centrifuged, ammonium sulfate is added to the supernatant to a final concentration of 10%, the mixture is recentrifuged, and the supernatant loaded onto a 10 mL Phenyl Sepharose column equilibrated in 10% ammonium sulfate, 20 mM Tris, pH 8. IFN-α cysteine muteins are eluted from the column using a 100 mL linear gradient from 10% ammonium sulfate, 20 mM Tris pH 8 to 30% ethylene glycol, 20 mM Tris, pH 8. The interferon pool from a Phenyl-Sepharose column can be further purified using a copper chelating column, S-Sepharose column or both.

Interferon cysteine muteins also can be solubilized and refolded using other reducing agents that also act as cysteine blocking agents. Substitution of reduced glutathione, thioglycolic acid or cysteamine for cysteine in the solubilization/refold mixtures yielded refolded, soluble IFN cysteine variants that could be purified and PEGylated following the procedures described in Example 7. When no reducing agent or 20 mM DTT was substituted for cysteine in the solubilization/refold mixtures, yields of refolded, soluble IFN cysteine muteins were reduced to non-detectable levels when the refold mixture was analyzed by Reversed Phase HPLC. Additionally, no refolded, soluble IFN cysteine mutein was recovered following S-Sepharose chromatography of the refold mixture when no reducing agent or 20 mM DTT was substituted for cysteine in the solubilization/refold mixtures.

The following muteins were expressed in E coli, refolded and purified using Protocol II: C1S, Q5C, 43C44, N45C, F47C, Q48C, A50C, C98S, Q101C, T106C, E107C, S163C, E165C, *166C, D2C, L3C, T6C, S8C, T52C, G102C, V103C, G104C, V105C, P109C, L110C, M111C, S160C, L161C, R162C, and K164C. These refolds were performed at pH 8 or in some instances 7.5.

Example 6

Bioactivities of IFN-α2 Cysteine Muteins

Biological activities of the purified Q5C, C98S, Q101C, T106C, E107C, and *166C IFN-α2 cysteine muteins that were purified using Protocol I of Example 5 were measured in the Daudi growth inhibition assay described in PCT/US00/00931. Protein concentrations were determined using Bradford or BCA protein assay kits (Bio-Rad Laboratories and Pierce). Commercial wild type rIFN-α2 and rIFN-α2 prepared as described in PCT/US00/00931 were analyzed in parallel on the same days to control for interday variability in the assays. The muteins inhibited proliferation of Daudi cells to the same extent as the wild type rIFN-α2 control proteins, within the error of the assay. Mean IC$_{50}$s for five of the muteins (Q5C, Q101C, T106C, E107C and *166C) were similar to the mean IC$_{50}$s of the wild type rIFN-α proteins ranging from 15-18 pg/ml. The mean IC$_{50}$ for the C98S protein was 28 pg/ml. These data are summarized in Table 4.

TABLE 4

Expression and in vitro Bioactivities of IFN-α2 Cysteine Muteins

| IFN-α2 Protein | Mutation Location | Relative Expression Total Cellular [1] | Percent Soluble [2] | Form Assayed | Mean IC$_{50}$ (pg/ml) | IC$_{50}$ Range [3] (pg/ml) |
|---|---|---|---|---|---|---|
| rIFN-α2 [4] | — | - | — | | 16 +/- 7 | 8-29 (n = 10) |
| rIFN-α2 [5] | — | ++++ | ~33 | Soluble | 13 +/- 4 | 7-19 (n = 10) |
| C1S | N-terminal region [6] | +/- | 0 | | | |
| Q5C | N-terminal region | ++++ | ~20 | Refolded | 17 | 15, 17, 20 |
| 43C44 | A-B loop | ++ | 0 | | | |
| N45C | A-B loop | ++ | 0 | | | |
| Q46C | A-B loop | +/- | 0 | | | |
| F47C | A-B loop | ++++ | ~5 | | | |
| Q48C | A-B loop | +/- | 0 | | | |
| A50C | A-B loop | +/- | 0 | | | |
| D77C | B-C loop | +/- | 0 | | | |
| C98S | C-helix [7] | +++++ | ~5-10 | Refolded | 28 | 22, 30, 32 |
| Q101C | C-D loop | +++++ | ~5-10 | Refolded | 18 | 10, 22, 23 |
| T106C | C-D loop | +++++ | ~5-10 | Refolded | 18 | 18, 18 |
| E107C | C-D loop | +++++ | ~5-10 | Refolded | 18 | 8, 22, 24 |
| T108C | C-D loop | +/- | 0 | | | |
| S163C | C-terminal region | ++++ | ~33 | | | |
| E165C | C-terminal region | +++ | ~20 | | | |
| *166C | C-terminus | +++ | ~20 | Refolded | 15 | 8, 16, 20 |

[1] Relative accumulation of the IFN-α2 protein in whole cell extracts
[2] Portion of the IFN-α2 protein in the osmotic shock supernatant, determined from SDS-PAGE gels
[3] IC$_{50}$ values from individual experiments. A range is shown when N > 5.
[4] Commercial wild type rIFN-α2 (Endogen, Inc.)
[5] Wild type rIFN-α2 prepared by Bolder BioTechnology, Inc.
[6] Mutation creates a free cysteine (C98) in the C-helix
[7] Mutation creates a free cysteine (C1) in the N-terminal region Biological activities of the following muteins, purified using Protocol II of Example 5, were measured in the Daudi growth inhibition assay described in PCT/US00/00931: C1S, D2C, L3C, S8C, N45C, F47C, C98S, V103C, V105C, E107C, M111C, R162C, S163C, K164C, E165C and *166C. The observed IC$_{50}$s are listed in Table 5 along with IC$_{50}$s for wild type rIFN-α protein controls used in the same experiments.

TABLE 5

In vitro Bioactivities of IFN-α2 Cysteine Muteins Purified by Protocol II with and without PEGylation

| IFNα2 Mutant | Mutation location | IC$_{50}$[1] (pg/ml) | IC$_{50}$ (pg/ml), 20K PEG-Protein[1] |
|---|---|---|---|
| RIFN-α2[2] | — | 15 to 55 | — |
| RIFN-α2[3] | — | 16 to 109 | — |
| C1S[4] | N-terminal region | 120, 130 | 100, 160 |
| D2C | N-terminal region | 39 | 300 |
| L3C | N-terminal region | 24, 75 | 105, 270 |
| S8C | N-terminal region | 37 | 220 |
| N45C | A-B loop | 52 | 104 |
| F47C | A-B loop | 66, 56, 58 | 120, 72, 240 |
| C98S[5] | C-helix | 105, 110, 100 | 500, 720, 900 |
| G104C | C-D loop | 110 | 600 |
| V105C | C-D Loop | 38 | 33 |
| E107C | C-D loop | 90, 98, 110 | 160, 220, 180 |
| M111C | C-D Loop | 40 | 190 |
| R162C | C-terminal region | 600 | 4000 |
| S163C | C-terminal region | 70, 50, 88 | 310, 125, 360 |

TABLE 5-continued

In vitro Bioactivities of IFN-α2 Cysteine Muteins Purified by Protocol II with and without PEGylation

| IFNα2 Mutant | Mutation location | $IC_{50}^1$ (pg/ml) | $IC_{50}$ (pg/ml), 20K PEG-Protein[1] |
|---|---|---|---|
| K164C | C-ter | 100 | 600 |
| E165C | C-ter | 43, 60, 51 | 160, 220, 300 |
| *166C | C-terminus | 48, 78, 96 | 120, 300 |

[1]$IC_{50}$ values from individual experiments. A range is shown when N>5.
[2]Commercial wild type rIFN-α2 (Endogen, Inc.)
[3]Wild type rIFN-α2 prepared by Bolder BioTechnology, Inc.
[4]Mutation creates a free cysteine (C98) in the C-helix
[5]Mutation creates a free cysteine (C1) in the N-terminal region Example 7

PEGylation of IFN-α2 Cysteine Muteins

The purified IFN-α2 cysteine muteins can be PEGylated using the procedures described in Example 3 and PCT/US98/14497 and PCT/US00/00931. A small-scale PEGylation experiment was performed with two of the purified rIFN-α2 cysteine muteins to identify conditions that allowed the proteins to be monoPEGylated at the free cysteine residue. Over-reduction of the proteins was monitored by non-reducing SDS-PAGE, looking for a shift to a higher than expected apparent molecular weight as a result of protein unfolding, or for the appearance of multiple PEGylated species generated as the result of native disulfide reduction. One µg aliquots of purified wild type and the rIFN-α2 muteins T106C and E107C were incubated for 1 hour with a 10-fold molar excess TCEP and a 20-fold molar excess of 5 kDA maleimide PEG at pH 8.5 at room temperature. After 60 min, the reactions were stopped and immediately analyzed by non-reducing SDS-PAGE. Both muteins yielded monoPEGylated protein under these conditions, based on SDS-PAGE analysis of the reaction mixtures. The apparent molecular weights of the monoPEGylated proteins were approximately 28 kDa by non-reducing SDS-PAGE. Wild-type rIFN-α2 showed no detectable PEGylation under these conditions. Control experiments indicated that the T106C and E107C cysteine muteins needed to be partially reduced with a reductant such as TCEP to be PEGylated. These data indicate that the PEG molecule is attached to the cysteine residue introduced into the T106C and E107C proteins.

Larger quantities of the IFN-α2 cysteine muteins can be modified with cysteine-reactive PEGs of various sizes and purified to obtain sufficient material for bioactivity measurements. For purification of the PEGylated proteins, the larger PEGylation reactions should be performed as described above for 1 hr at room temperature, diluted 10× with 20 mM MES, pH 5.0, adjusted to pH 3.0, and then loaded quickly onto an S-Sepharose column using conditions similar to those described for initial purification of the rIFN-α2 muteins. The presence of the PEG moiety decreases the protein's affinity for the resin, allowing the PEGylated protein to be separated from the non-PEGylated protein. The chromatogram from the S-Sepharose column should show two major protein peaks. The early eluting major peak (eluting at an NaCl concentration less than 230 mM) should be the mono-PEGylated IFN-α protein, which can be confirmed by non-reducing SDS-PAGE analysis. The apparent molecular weight of monoPEGylated IFN-α2 that has been modified with a 5 kDa cysteine-reactive PEG is approximately 28 kDa by SDS-PAGE. The later eluting major peak (eluting at approximately 230 mM NaCl) should be the unreacted IFN-α2 protein. Fractions from the early eluting peaks containing predominantly PEG-IFN-α2 can be pooled and used for bioactivity measurements. Biological activity of the purified PEG-IFN-α2 proteins can be measured in the Daudi cell assay described in PCT/US00/00931. Concentrations of the proteins can be determined using a Bradford dye binding assay. In vivo biological activities of the PEGylated IFN-α2 cysteine muteins can be determined as described in PCT/US98/14497 and PCT/US/US00/00931.

For PEGylation of the Q5C mutein, the purified protein was diluted to 100 µg/ml protein with 100 mM Tris, pH 8. A 15-fold excess of 5 kDa-maleimide PEG is added followed by 10-15-fold molar excess of TCEP. EDTA was also added (0.5 mM final concentration) to inhibit disulfide formation once the protein is partially reduced. The mixture was held at room temperature, 2 hours. An alternative method that also gave good PEGylation efficiency involved repeated additions of the PEG and TCEP reagents. We have found that 3 rounds of adding 10× molar excess PEG reagent and 10× molar excess TCEP over a period of 2 hours gave greater than 80% PEGylation efficiency. This latter procedure of repeated additions of the PEG and TCEP reagents was used successfully to prepare Q5C modified with 10 kDa-, 20 kDa- and 40 kDa-PEGs. The PEGylated proteins were separated from unreacted Q5C starting material and PEGylation reagents by ion-exchange chromatography using the S-Sepharose protocol described in Example 5. Alternative methods such as other ion exchangers (Q, DEAE, CM), HIC resins (Phenyl, Butyl), affinity columns, size exclusion columns, or chelating resins may be used to purify the PEGylated protein.

Biological activity of the purified 10 kDa-, 20 kDa- and 40 kDa-PEG-Q5C proteins were measured in the Daudi cell assay described in PCT/US00/00931. Concentrations of the proteins were determined using a Bradford dye binding assay. Mean $IC_{50}$s for the 10 kDa-PEG-Q5C, 20 kDa-PEG-Q5C, and 40 kDa-PEG-Q5C proteins were determined to be 70 pg/ml (N=2 assays), 100 pg/ml (N=8 assays), and 108 pg/ml (N=8 assays), respectively.

Example 8

Cloning, Expression and Purification of Wild Type G-CSF and G-CSF (C7S)

A. Cloning DNA sequences encoding G-CSF. A cDNA encoding G-CSF was amplified by PCR from total RNA isolated from the human bladder carcinoma cell line 5637 (American Type Culture Collection). The cells were grown in RPMI 1640 media supplemented with 10% FBS, 50 units/ml penicillin and 50 µg/ml streptomycin. RNA was isolated from the cells using an RNeasy Mini RNA isolation kit purchased from Qiagen, Inc. (Santa Clarita, Calif.) following the manufacturer's directions. First strand synthesis of single-stranded cDNA was accomplished using a 1st Strand cDNA Synthesis Kit for RT-PCR (AMV) from Boehringer Mannheim Corp and random hexamers were used as the primer. Subsequent PCR reactions using the products of the first strand synthesis as template were carried out with forward primer BB91 (5>CGCAAGCTTGCCACCATG-GCTGGACC TGCCACCCAG>3; SEQ ID NO:1) and reverse primer BB92 (5>CGCGGATCCTCCG-GAGGGCTGGGCAAGGT GGCGTAG >3; SEQ ID NO:2). Primer BB91 anneals to the 5' end of the coding sequence for the G-CSF secretion signal and the reverse primer, BB92, anneals to the 3' end of the G-CSF coding sequence. The resulting ~640 bp PCR product was digested with Hind III and Bam HI, gel purified and cloned into pCDNA3.1(+) vector that had been digested with Hind III and Bam HI, alkaline phosphatase treated, and gel purified. A clone with the correct DNA sequence (Souza et al., 1986; Nagata et al., 1986a,b) was designated pCDNA3.1(+)::G-CSFfus or pBBT165.

PCR was used to modify this G-CSF clone for periplasmic and cytoplasmic expression in *E. coli* of wild type G-CSF (wild type) and a variant in which the naturally occurring free cysteine at position 17 was replaced by serine (C17S). The wild type G-CSF protein contains 5 cysteines, two of which participate in critical disulfide bonds and one free cysteine (C17) that is partially buried and not required for activity (Ishikawa et al., 1992, Kuga et al., 1989, Lu et al., 1992, Wingfield et al., 1988). To avoid potential difficulties caused by the unpaired cysteine, we constructed a variant containing the Cys to Ser substitution at position 17 (C17S) as our platform molecule. All subsequent cysteine muteins were prepared with the C17S substitution present. G-CSF (C17S) has been reported to possess biological activity identical to wild type G-CSF (Ishikawa et al., 1992, Lu et al., 1992).

Secreted G-CSF does not contain an added N-terminal methionine and has an amino acid sequence identical to naturally occurring G-CSF (Souza et al., 1986). In order to express a secreted form of G-CSF, PCR was used to fuse the leader sequence of the *E. coli* heat-stable enterotoxin (STII) gene (Picken et al., 1983) to the coding sequence for mature G-CSF and a TAA stop codon was added following the carboxy-terminal residue, P174. At the same time, the aminoterminal portion of the G-CSF coding sequence was also modified. Codons for prolines at positions 2, 5, and 10 were all changed to CCG, and an Xho I restriction site was introduced by changing the L18 codon from TTA to CTC in order to facilitate subsequent mutagenesis procedures.

These constructions were carried out in parallel for the wild type and C17S genes and employed three sequential PCR reactions. For the C17S construct, the first reaction used forward primer BB116 (5>GGCCCGGCCAGCTC-CCTGCCGCAGAGCTTCCTGCTGAAGAGCCTCGAG CAAGTGCGTAAGATCCAG>3; SEQ ID NO:3) and reverse primer BB114 (5>CGCGAATTCTTAGGG CTGGGCAAGGTGGCG>3; SEQ ID NO:4) and the cloned G-CSF cDNA as template. BB116 anneals to the 5' end of the coding sequence of mature G-CSF and introduces the codon changes noted above at P2, P5, P10, and L18 which do not change the amino acids encoded. It also introduces the C17S mutation (TGC=>AGC) and changes the leucine codon at position 15 to the preferred CTG triplet. BB 114 anneals to the 3' end (18 bp) of the G-CSF coding sequence and introduces a TAA translational stop codon immediately following the the carboxy-terminal residue, P174. BB114 also contains an Eco RI site for cloning purposes. For the wild type construct, the first reaction used forward primer BB117 (5>GGCCCGGCCAGCTCCCTGCCGCAGAGCT-TCCTGCTTAAGTGCCTCGAGCAAGTGCGTAAGATC CAG>3; SEQ ID NO:5) and reverse primer BB114 (sequence above) with the cloned G-CSF cDNA as template. BB 117 is identical to BB 116 with two exceptions; the naturally occurring C 17 codon, TGC, is present and the L15 codon used is CTT. This CTT creates an Afl II restriction site in order to provide a rapid and convenient method for distinguishing wild type C17 clones from the C17S variant. The C17S clones carry the CTG codon at position 15 and therefore lack the Afl II rsetriction site. The 530 bp PCR product from each of these reactions was gel purified and used as template for the second PCR reaction.

For the second reaction each of the 530 bp gel purified products was amplified with forward primer BB115 (5>AT-GTTCGTTTTCTCTATCGCTACCAACGCG-TACGCAACCCCGCTG GGCCCGGCCAGCTCCCTG>3; SEQ ID NO:6) and reverse primer BB114 (described above). The 3' portion (27 nucleotides) of BB 115 anneals to the 5' end of the modified coding sequence of mature G-CSF which is identical in both the wild type and C17S PCR products. The 5' segment (36 nucleotides) of BB115 encodes a portion of the STII leader peptide. The 550 bp PCR products of each of these secondary reactions were gel purified and used as template for the third and final round of PCR.

In the third reaction each of the ~550 bp gel purified products was amplified with forward primer BB 11 (5>CCCCCTCTAGACATATGAAGAAGAA-CATCGCATTCCTGCTGGCATCTATGTTCGT TTTCTC-TATCG>3; SEQ ID NO:7) and reverse primer BB114 (described above). BB11 adds the remainder of the STII leader peptide and contains an Nde I site overlapping the initiator ATG of the STII leader as well as an Xba I site for cloning purposes. The ~620 bp products of the these reactions were digested with Eco RI and Xba I and cloned into similarly digested plasmid vector pBC-SK(+) (Stratagene) for sequencing.

For the wild type construct, one clone, designated pBBT187, was found to contain the correct sequence for the 620 bp Nde I-Eco RI segment containing the STII-G-CSF coding sequence. This fragment was then subcloned into (Nde I+Eco RI) cut expression vector pCYB1 (New England BioLabs). The resulting plasmid was termed pBBT188. For the C17S construct, none of three clones sequenced was found to contain the correct sequence; all had one or more errors. One clone contained a single missense mutation at the A10 position of the STII leader; the rest of the sequence of the 620 bp Nde I-Eco RI segment was correct. In vitro recombination between this clone and plasmid pBBT188 was used to generate a STII-G-CSF(C17S) construct of the correct sequence in pCYB1. pBBT188 and the C17S clone containing the single missense mutation at the A10 position of the STII leader, were both digested with Bsi WI and Eco RI. The only Eco RI site present in either plasmid is that which follows the G-CSF translational stop codon. Bsi WI also cuts only once at a site within the coding sequence of the STII leader peptide, 7 bp from the beginning of the mature G-CSF coding sequence. Therefore by replacing the ~535 bp Bsi WI-Eco RI fragment of pBBT188 with the 535 bp Bsi WI-Eco RI fragment having the correct C17S construct sequence, we generated a pCYB1 derivate to that expressed the STII-G-CSF(C17S) coding sequence. This plasmid was designated pBBT223

For cytoplasmic expression in *E. coli* the cloned STII-G-CSF wild type and STII-G-CSF (C17S) genes were modified by PCR to eliminate the STII leader sequences and add an initiator methionine codon (ATG) immediately preceding the codon of the amino-terminal amino acid (T1) of mature G-CSF. The sequence-verified STII-G-CSF wild type and STII-G-CSF(C17S) clones were amplified with primers BB166 (5>CGCCATATGACCCCGCTGGGCCCGGC-CAG>3; SEQ ID NO:8) and BB114 (described above). BB166 anneals to the 5' end of the coding sequence of mature G-CSF and encodes an initiator methionine preceding the first amino acid of mature G-CSF. An Nde I site, which overlaps the ATG was included for cloning purposes. The ~540 bp products of these PCR reactions were digested with Nde I plus Aat II which cuts ~400 bp downstream of the Nde I site. These ~400 bp fragments were gel purified and cloned into pBBT187, the pBC-SK(+)::STII-G-CSF construct described above, which had been cut with Nde I plus Aat II, treated with alkaline phosphatase and gel purified. One Met-G-CSF wild type and one Met-G-CSF(C17S) clone were sequenced and both were found to contain the correct sequences. These Met-G-CSF wild type and Met-G-CSF(C17S) genes were subcloned as Nde I-Eco RI fragments into Nde I-Eco RI cut expression vector pCYB1, which is described above. The resulting plasmids were designated: pBBT225=pCYB1::MetG-CSF and pBBT226=pCYB1::Met-G-CSF(C17S).

B. Expression of Wild Type G-CSF and G-CSF (C17S) in *E. coli* pBBT225, which encodes Met-G-CSF wild type, pBBT226 which encodes Met-G-CSF(C17S) and the pCYB1 parent vector, were transformed into *E. coli* JM109. Experiments with these strains resulted in expression of the G-CSF proteins. Secreted G-CSF, both wild type and C17S forms, are preferable because they lack the non-natural methionine residue at the N-terminus of cytoplasmically-expressed Met-G-CSF proteins.

For expression of secreted G-CSF, pBBT188 [pCYB1::STII-G-CSF], pBBT223 [pCYB1::STII-G-CSF(C17S)] and the parental vector pCYB1 were transformed into *E. coli* W3110. The resulting strains were designated as BOB130: W3110(pCYB1), BOB213: W3110(pBBT188), and BOB268: W3110(pBBT223). In preliminary screening experiments, strains were grown overnight in Luria Broth (LB media) containing 100 μg/ml ampicillin at 37° C. in roll tubes. Saturated overnight cultures were diluted to ~0.025 OD. at $A_{600}$ in LB containing 100 μg/ml ampicillin and incubated at 28, 37 or 42° C. in shake flasks Typically a 25 ml culture was grown in a 250 ml shake flasks When culture O.D.s reached ~0.3-0.5, IPTG was added to a final concentration of 0.5 mM to induce expression of G-CSF. For initial experiments, cultures were sampled at 0, 1, 3, 5 and ~16 h post-induction. Samples of induced and uninduced cultures were analyzed by SDS-polyacrylamide gel electrophoresis (SDS-PAGE) on precast 14% Tris-glycine polyacrylamide gels and stained with Coomassie Blue. Induced cultures of both BOB213 (wild type) and BOB268 (C17S) showed a band at approximately 19 kDA, which is consistent with the mature G-CSF molecular weight. This band was not detected in the uninduced cultures of BOB213 and BOB268 or in induced or uninduced cultures of BOB 130, the vector-only control. Western blot analyses showed that this ~19 kDa band in BOB213 and BOB268 lysates reacted strongly with an anti-human G-CSF antiserum (R&D Systems). This antibody did not recognize proteins in uninduced cultures of BOB213 and BOB 268 or in induced or uniduced cultures of BOB130, the vector only control. These Western blots also showed that this ~19 kDa band co-migrated with a commercial human G-CSF standard purchased from R & D Systems. This result suggests that the STII leader peptide has been removed, which is consistent with the protein having been secreted to the periplasmic. N-terminal sequencing studies presented in Example 10 indicate the STII signal sequence was properly processed.

The 16 hour post-induction samples from 28° C. and 37° C. cultures also were subjected to osmotic shock based on the procedure of Koshland and Botstein (1980). This procedure ruptures the *E. coli* outer membrane and releases the contents of the periplasmic into the surrounding medium. Subsequent centrifugation separates the soluble periplasmic components (recovered in the supernatant) from cytoplasmic, insoluble periplasmic, and cell-associated components (recovered in the pellet). At both temperatures, some of the G-CSF protein synthesized, for both wild type, by BOB213, and C17S by BOB268 was recovered in the supernatant, but the bulk of the G-CSF proteins remained associated with the pellet. This indicates that while the protein appears to be processed and secreted to the periplasmic, it is accumulated there primarily in an insoluble form.

The preliminary screen of expression conditions for G-CSF wild type and the C17S variant showed that both proteins were relatively well expressed under a variety of conditions. For large scale expression and purification cultures were grown at 28° C. and induced for 16 hours.

C. Purification of Wild Type G-CSF and G-CSF (C17S). Wild type and G-CSF (C17S) were expressed and purified at a larger scale using identical protocols. Fresh saturated overnight cultures of BOB213 (wild type) and BOB268 (C17S) were inoculated at ~0.05 OD @ $A_{600}$ in LB containing 100 μg/ml ampicillin. Typically, 400 ml cultures were grown in a 2L baffled shake flask at 28° C. in a gyrotory shaker water bath at 250 rpm. When cultures reached a density of ~0.5-0.7 OD, IPTG was added to a final concentration of 0.5 mM. The induced cultures were then incubated overnight for ~16 h. The cells were pelleted by centrifugation and frozen at −80° C. Cell pellets were thawed and treated with 5 mL of B-PER™ bacterial protein extraction reagent according to the manufacturer's (Pierce) protocols. The insoluble material, which contained the bulk of the G-CSF protein, was recovered by centrifugation and resuspended in B-PER. This mixture was treated with lysozyme (200 μg/mL) for 10 min to further disrupt the cell walls, and $MgCl_2$ (10 mM final concentration) and protease-free DNAse (2 μg/ml) were added. Insoluble G-CSF was collected by centrifugation and washed, by resuspension in water and recentrifugation, to remove most of the solubilized cell debris. The resulting pellet containing insoluble G-CSF was dissolved in 20 ml of 8 M urea, 25 mM cysteine in 20 mM Tris Base. This mixture was stirred for 30 min at room temperature then diluted into 100 ml of 40 mM sodium phosphate, 40 μM copper sulfate, 15% glycerol, pH 8.0. This refold mixture was held at 4° C. for 2 days. The pH of the refold mixture was then adjusted to 4.0 with dilute HCl and the mixture was centrifuged before being loaded onto a 5 ml S-Sepharose column (Pharmacia HiTrap) equilibrated in 40 mM sodium phosphate pH 4.0 (Buffer A). The bound proteins were eluted with a linear salt gradient from 0-100% Buffer B (500 mM NaCl, 40 mM sodium phosphate, pH 4.0). Wild type G-CSF and G-CSF (C17S) eluted from the S-Sepharose column as single major peaks at a salt concentration of approximately 300-325 mM NaCl. Column fractions were analyzed by non-reducing SDS-PAGE. Fractions containing G-CSF and no visible impurities were pooled. The final yields of G-CSF wild type and G-CSF (C17S), as determined by Bradford analysis, were about 1.1 mg and 3.3 mg, respectively from 400 ml of culture. Purified wild type G-CSF and G-CSF (C17S) comigrated under reducing and non-reducing conditions of SDS-PAGE. The apparent molecular weights of reduced and non-reduced G-CSF and G-CSF (C17S) are approximately 19 and 17 kDa, respectively.

D. In Vitro Bioactivities of Wild Type G-CSF and G-CSF (C17S). A cell proliferation assay using the murine NFS60 cell line was developed to measure bioactivities of wild type G-CSF and G-CSF (C17S). The NFS60 cell line was obtained from Dr. J. Ihle of the University of Tennessee Medical School, Memphis Tenn. This cell line proliferates in response to human or mouse G-CSF or IL3 (Weinstein et al., 1986). The cells were maintained in RPMI 1640 media supplemented with 10% FBS, 50 units/ml penicillin, 50 μg/ml streptomycin and 17-170 units/ml mouse IL-3 (R&D Systems). Bioassays were performed in cell maintenance media minus IL-3. In general, the bioassays were set up by washing the NFS60 cells three times with RPMI media (no additives) and resuspending the cells at a concentration of $0.5$-$1\times10^5$/ml in cell maintenance media minus IL-3. Fifty μl ($2.5$-$5\times10^3$ cells) of the cell suspension was aliquotted per test well of a flat bottom 96 well tissue culture plate. Serial dilutions of the protein samples to be tested were prepared in maintenance media minus IL,3. Serial dilutions of recombinant human G-CSF (E. coli-expressed; R&D Systems) were analyzed in parallel. Fifty μl of the diluted protein samples were added to the test wells and the plates incubated at 37° C. in a humidified 5% $CO_2$ tissue culture incubator. Protein samples were assayed in triplicate wells. After approximately 48-72 h, 20 μl of CellTiter 96 AQueous One Solution (Promega Corporation) was added to each well and the plates incubated at 37° C. in the tissue culture incubator for 1-4 h. Absorbance of the wells was read at 490 nm using a microplate reader. Control wells contained media but no cells. Mean absorbance values for the triplicate control wells were subtracted from mean values obtained for the test wells. $EC_{50}$s, the concentration at half maximal stimulation, were calculated for each sample.

The NFS60 cell line shows a strong proliferative response to G-CSF, as evidenced by a dose-dependent increase in cell number and absorbance values. Commercial G-CSF and G-CSF prepared by us had mean $EC_{50}$ of 19 and 10 pg/ml, respectively, in the bioassay (Table 6). Unexpectedly, G-CSF (C17S) had a mean $EC_{50}$ of 7 pg/ml and was reproducibly 1.5-to 2-fold more potent than our wild type G-CSF standard and ~3-fold more potent than the commercial wild type G-CSF standard in the bioassay (Table 3). The superior activity of G-CSF (C17S) was surprising because others have reported that wild type G-CSF and G-CSF (C17S) have identical activities (Lu et al., 1992).

Example 9

Construction, Expression, Purification and Bioactivity of G-CSF (C17S) Cysteine Muteins A. Construction of G-CSF Cysteine Muteins.

Fifteen mutant G-CSF genes were constructed using site-directed PCR-based mutagenesis procedures similar to those described in PCT/US00/00931 and Innis et al. (1990) and White (1993). We constructed five muteins in the amino-terminal region proximal to Helix A [*-1C (the addition of a cysteine residue onto the natural amino terminus), T1C, L3C, A6C and S7C]; two muteins in the B-C loop [E93C and S96C]; six muteins in the C-D loop [A129C, T133C, A136, A139C, A141C and S142C]; and two muteins in the carboxy-terminal region distal to Helix D [Q173C and *175C (the addition of a cysteine residue to the natural carboxy-terminus)]. The G-CSF cysteine muteins were all constructed in the C17S background to avoid potential difficulties and/or ambiguities that might be caused by the unpaired cysteine normally present at position 17 in wild type G-CSF. G-CSF (C17S) had previously been reported to possess full biological activity (Ishikawa et al., 1992; Lu et al., 1992) and in our E. coli secretion system we find that the yields of purified C17S are higher than that of purified wild type G-CSF. In addition, in the in vitro assay our recombinant C 17S is more active than wild type G-CSF produced by us and a second E. coli-produced recombinant wild type G-CSF obtained from a commercial vendor (R&D Systems, Inc.).

The template used for the mutagenic PCR reactions was plasmid pBBT227 in which the STII-G-CSF (C17S) gene from pBBT223 (described in Example 8) was cloned as an Nde I-Eco RI fragment into Nde I-Eco RI cut pUC18. PCR products were digested with appropriate restriction endonucleases, gel-purified and ligated with pBBT227 vector DNA that had been cut with those same restriction enzymes, alkaline phosphatase treated, and gel-purified. Transformants from these ligations were grown up and plasmid DNAs isolated and sequenced. The sequence of the entire cloned mutagenized PCR fragment was determined to verify the presence of the mutation of interest, and the absence of any additional mutations that potentially could be introduced by the PCR reaction or by the synthetic oligonucleotide primers.

The cysteine substitution mutation L3C was constructed as follows. The mutagenic forward oligonucleotide BB172 (5>ACCAACGCGTACGCAACCCCGTGTGGC-CCGGCCAGC>3; SEQ ID NO:9) was designed to change the codon CTG for leucine at position 3 of mature G-CSF to a TGT encoding cysteine and to span the nearby Mlu I site. This oligo was used in PCR with the reverse, non-mutagenic, primer BB188 (5>GCCATCGCCCTGGATCT-TACG>3; SEQ ID NO: 10) which anneals to DNA sequences encoding amino acid residues 21-27 of mature G-CSF in pBBT227. A 100 μl PCR reaction was performed in 1× Promega PCR buffer containing 1.5 mM $MgCl_2$, each primer at 0.4 μM, each of dATP, dGTP, dTTP and dCTP at 200 AIM, 3 ng of template plasmid pBBT227 (described above), 2.5 units of Taq Polymerase (Promega), and 0.5 units of Pfu Polymerase (Stratagene). The reaction was performed in a Perkin-Elmer GeneAmp® PCR System 2400 thermal cycler. The reaction program entailed: 96° C. for 3 minutes, 25 cycles of [95° C. for 60 seconds, 60° C. for 30 seconds, 72° C. for 45 seconds] and a hold at 4° C. A 10 μl aliquot of the PCR reaction was analyzed by agarose gel electrophoresis and found to produce a single fragment of the expected size ~100 bp. The remainder of the reaction was "cleaned up" using the QIAquick PCR Purification Kit (Qiagen) according to the vendor protocol and digested with Mlu I and Xho I (New England BioLabs) according to the vendor protocols. Following an additional clean up step using the QIAquick PCR Purification Kit, the digestion products were ligated with pBBT227 that had been cut with Mlu I and Xho I, treated with calf intestinal alkaline phosphatase (New England BioLabs) and gel purified. The ligation reaction was used to transform E. coli and plasmids from resulting transformants were sequenced. A clone having the L3C mutation and the correct sequence throughout the ~70 bp Mlu I-Xho I segment was identified.

The substitution mutation T1C was constructed and sequence verified using the protocols detailed above for L3C with the following difference. The mutagenic oligonucleotide BB171 (5>ACCAACGCG TACGCATGC-CCGCTGGGCCCGGCCAGC>3; SEQ ID NO: 11), which changes the ACC codon for T1 to a TGC codon for cysteine and spans the nearby Mlu I site, was used in the PCR reaction in place of BB172.

The substitution mutation Q173C was constructed and sequence verified using the protocols detailed above for L3C with the following differences. The mutagenic reverse oligonucleotide BB185 (5>CGCGA ATTC TTAGGGACAG-GCAAGGTGGCG >3; SEQ ID NO: 12), which changes the CAG codon for Q173 to a TGT codon for cysteine and spans the nearby Eco RI site, was used in the PCR reaction in place of BB172. The forward, non-mutagenic, primer BB187 (5>GCCATCGCCCTGGATCTTACG>3; SEQ ID NO: 13) which anneals to the DNA sequence encoding amino acid residues 78-84 of mature G-CSF in pBBT227 was used in place of BB188. A 10 μl aliquot of the PCR reaction was analyzed by agarose gel electrophoresis and found to produce a single fragment of the expected size 300 bp. The remainder of the reaction was "cleaned up" using the QIAquick PCR Purification (Qiagen) according to the vendor protocol and digested with Sty I and Eco RI (New England BioLabs) according to the vendor protocols. Following an additional clean up step using the QIAquick PCR Purification Kit, the digestion products were run out on a 1.5% agarose gel and the ~220 bp Sty I-Eco RI fragment of interest was gel purified using a QIAquick Gel Extraction Kit (Qiagen) according to the vendor protocol. The gel purified fragment was ligated with pBBT227 that had been cut with Sty I and Eco RI, treated with calf intestinal alkaline phosphatase (New England BioLabs) and gel purified. The ligation reaction was used to transform E. coli and plasmids from resulting transformants were sequenced. A clone having the Q173C mutation and the correct sequence throughout the 220 bp Sty I-Eco RI segment was identified.

A mutation was also constructed that added a cysteine following the carboxyterminal amino acid of the G-CSF coding sequence. This mutant, termed *175C was constructed using the protocols described above for the construction of the Q173C mutant with the following differences. The mutagenic oligonucleotide BB186 (5>CGCGAATTCTTAACAGGGCTGGGCAAG-GTGGCGTAG>3; SEQ ID NO:14), which inserts the a TGT codon for cysteine between the CCC codon for P174 and a TAA stop codon and spans the nearby Eco RI site, was used in the PCR reaction in place of BB185.

The substitution mutation A6C was constructed using the technique of "mutagenesis by overlap extension" as described in Horton et al. (1993) and PCT/US00/00931. The initial, or "primary" PCR reactions for the A6C construction were performed in a 50 μl reaction volume in 1× Promega PCR buffer containing 1.5 mM MgCl$_2$, each primer at 0.4 μM, each of dATP, dGTP, dTTP and dCTP at 200 μM, 1 ng of template plasmid pBBT227, 1.5 units of Taq Polymerase (Promega), and 0.25 units of Pfu Polymerase (Stratagene). The reactions were performed in a Perkin-Elmer Gene-Ampt3 PCR System 2400 thermal cycler. The reaction program entailed: 96° C. for 3 minutes, 25 cycles of [95° C. for 60 seconds, 60° C. for 30 seconds, 72° C. for 45 seconds] and a hold at 4° C. The primer pairs used were [BB173× BB188] and [BB174×B3125]. BB188 (5>GCCATCGC-CCTGGATCT ACG>3; SEQ ID NO:10) anneals to DNA sequences encoding amino acid residues 21-27 of mature G-CSF in pBBT227. BB125 (5>CTATGC GGCATCA-GAGCAGATA>3; SEQ ID NO:17) anneals to the pUC18 vector sequence 20 bp upstream of the cloned G-CSF sequence. BB173 and BB174 are complementary mutagenic oligonucleotides that change the GCC codon for A6 to a TGC codon for cysteine. The sequence of BB 173 is (5>CCGCTGGGCCCGTGCAGCTCCCTGCCG>3; SEQ ID NO:15) and the sequence of BB174 is (5>CGGCAGG-GAGCTGCACGGGCCCAGCGG>3; SEQ ID NO: 16). The PCR products were run out on a 2% agarose gel, which showed that the [BB173×BB188] and [BB174×BB125] PCR reactions gave products of the expected sizes: ~80 bp for [BB173×BB188] and ~140 bp for [BB174×BB125]. These fragments were excised from the gel, pooled, and eluted together from the agarose gel slices using a QIAquick Gel Extraction Kit (Qiagen) according to the vendor protocol and recovered in 30 μl 10 mM Tris-HCl (pH 8.5). These two mutagenized fragments were then "spliced" together in the subsequent, or "secondary" PCR reaction. In this reaction 3 μl of of the gel-purified PCR products of the primary reactions were used as template and BB125 and BB188 were used as primers. The reaction volume was 100 pl and 2.5 units of Taq Polymerase and 0.5 units of Pfu Polymerase were employed. Otherwise, the reaction conditions were identical to those used in the primary reactions. An aliquot of the secondary PCR was analyzed by agarose gel electrophoresis and the expected band of 190 bp was observed. The bulk of the secondary PCR reaction was "cleaned up" using the QIAquick PCR Purification (Qiagen), digested with Nde I and Xho I (New England BioLabs) according to the vendor protocols. Following an additional clean up using the QIAquick PCR Purification Kit, the digestion products were ligated with pBBT227 that had been cut with Nde I and Xho I, treated with calf intestinal alkaline phosphatase (New England BioLabs) and gel purified. The ligation reaction was used to transform E. coli and plasmids from resulting transformants were sequenced to identify a clone containing the A6C mutation and having the correct sequence throughout the ~130 bp Nde I-Xho I segment.

The substitution mutation S7C was constructed and sequence verified using the protocols detailed above for A6C with the following differences. Complementary mutagenic primers BB175 (5>CTGGGCCCGGCCTGCTCCCTGC-CGCAG>3; SEQ ID NO:18) and BB176 (5>CTGCG-GCAGGGAGCAGGCCGGGCCCAG>3; SEQ ID NO:19), which change the AGC codon for S7 to a TGC codon for cysteine, replaced BB 173 and BB 174 respectively in the primary PCR reactions.

A mutation that added a cysteine codon prior to the codon for the amino-terminal residue, T1, of mature G-CSF was constructed and sequence-verified. This mutation, termed *-1C was constructed using the protocol described above for construction of A6C with the following differences. Complementary mutagenic primers BB206 (5>AACCCG-TACGCATGTACCCCGCTGGGC>3; SEQ ID NO:20) and BB207 (5>GCC CAGCGGGGTACATGCG-TACGCGTT>3; SEQ ID NO:21), which insert a TGC codon for cysteine between the GCA codon for the carboxytermi-nal residue of the STII leader sequence and the ACC codon for the amino-terminal residue of mature G-CSF in pBBT227, replaced BB173 and BB174 respectively in the primary PCR reactions. The primary PCR reactions were performed in a 20 μl reaction volume. Each primer was present at 0.5 μM. The reaction included 0.5 ng of template plasmid pBBT227, 2 units of Taq Polymerase, and 0.25 units of Pfu Polymerase. The reaction program entailed: 95° C. for 3 minutes, 25 cycles of [940 C for 60 seconds, 60° C. for 30 seconds, 72° C. for 45 seconds ] and a hold at 4° C. The products of the primary reactions were loaded directly onto a preparative 2% agarose gel. The primary reactions gave products of the expected sizes: ~100 bp for [BB206×BB188] and ~125 bp for [BB207×BB125]. In the secondary PCR, the reaction volume was 100 μl, 5 μl of the gel-purified PCR products of the primary reactions used as template, BB187 and BB126 were used as primers, and 4 units of Taq Polymerase and 0.25 units of Pfu Polymerase were employed. Otherwise, the reaction conditions were identical to those used in the primary reactions.

The substitution mutation A129C was constructed and sequence verified using the protocols detailed above for A6C with the following differences. The primary PCR reactions employed primer pairs [BB177×BB126] and [BB178×

BB187]. The reverse, non-mutagenic primer BB126 (5>TGTGGAATTGTGAGCGGATAAC>3; SEQ ID NO:22) anneals to the pUC18 vector sequence ~40 bp downstream of the cloned G-CSF sequence. The forward, non-mutagenic, primer BB1187 (5>GCCATCGCCCTG-GATCTTACG>3; SEQ ID NO:13) anneals to the DNA sequence encoding amino acid residues 78-84 of mature G-CSF in pBBT227. BB177 and BB178 are complementary mutagenic oligonucleotides that change the GCC codon for A129C to a TGC codon for cysteine. The sequence of BB177 is (5>GGAATGGCCCCTTGCCTGCAGC-CCACC>3; SEQ ID NO:23) and the sequence of BB178 is (5>GGTGGGCTGCAGGCAAGGGGCCATTCC>3; SEQ ID NO:24). The products of the primary reactions gave products of the expected sizes: ~220 bp for [BB177×BB126] and ~170 bp for [BB178×BB187]. The secondary PCR employed BB187 and 1B126 as primers and produced a product of the expected size: 360 bp. This product was digested with Sty I and Eco RI (New England BioLabs) according to the vendor protocols. Following an additional clean up using the QIAquick PCR Purification Kit, the digestion products were ligated with pBBT227 that had been cut with Sty I and Eco RI, treated with calf intestinal alkaline phosphatase (New England BioLabs) and gel purified. The ligation reaction was used to transform *E. coli* and plasmids from resulting transformants were sequenced to identify a clone containing the A129C mutation and having the correct sequence throughout the ~230 bp Sty I-Eco RI segment.

The substitution mutation T133C was constructed and sequence verified using the protocols detailed above for A129C with the following differences. Complementary mutagenic primers BB179 (5>GCCCTGCAGCCCTGCCA-GOGTGCCATG>3; SEQ ID NO:25) and BB180 (5>CATG-GCACCCTGGCAGGGCTGCAG GGC>3; SEQ ID NO:26), which change the ACC codon for T133 to a TGC codon for cysteine, replaced BB173 and BB174 respectively in the primary PCR reactions. The products of the primary reactions gave products of the expected sizes: ~205 bp for [BB179×BB126] and ~180 bp for [BB180×BB187].

The substitution mutation A139C was constructed and sequence verified using the protocols detailed above for A129C with the following differences. Complementary mutagenic primers BB181 (5>GGTGCCATGCCGTGCT-TCGCCTCTGCT>3; SEQ ID NO:27) and BB182 (5>AG-CAGAGGCGAAGCACGGCATGGCACC>3; SEQ ID NO:28), which change the GCC codon for A139 to a TGC codon for cysteine, replaced BB173 and BB174 respectively in the primary PCR reactions. The products of the primary reactions gave products of the expected sizes: ~185 bp for [BB181×BB126] and ~200 bp for [BB182×BB187].

The substitution mutation S142C was constructed and sequence verified using the protocols detailed above for A129C with the following differences. Complementary mutagenic primers BB183 (5>CCGGCCTTCGCCTGT-GCTTTCCAGCGC>3; SEQ ID NO:29) and BB184 (5>GCGCTGGAAAGCACAGGCGAAGGCCGG>3; SEQ ID NO:30), which change the TCT codon for S142 to a TGT codon for cysteine, replaced BB173 and BB174 respectively in the primary PCR reactions. The products of the primary reactions gave products of the expected sizes: ~180 bp for [B3B183×BB126] and ~210 bp for [BB184×BB187].

The substitution mutation A136C was constructed and sequence verified using the protocols detailed above for A129C with the following differences. Complementary mutagenic primers BB224 (5>CCCACCCAGGGTTGCAT-GCCGGCCTTC>3; SEQ ID NO:31) and BB225 (5>GAAGGCCGGCATGCAACCCTGGGTGGG>3; SEQ ID NO:32), which change the GCC codon for A136 to a TGC codon for cysteine, replaced BB 173 and BB174 respectively in the primary PCR reactions. The primary PCR reactions were performed in a 20 μl reaction volume. Each primer was present at 0.5 μM. The reaction included 0.5 ng of template plasmid pBBT227, 2 units of Taq Polymerase, and 0.25 units of Pfu Polymerase. The reactions were performed a Perkin-Elmer GeneAmp® PCR System 2400 thermal cycler. The reaction program entailed: 95° C. for 3 minutes, 25 cycles of [94° C. for 60 seconds, 60° C. for 30 seconds, 72° C. for 45 seconds] and a hold at 4° C. The products of the primary reactions were loaded directly onto a preparative 2% agarose gel. The primary reactions gave products of the expected sizes: ~195 bp for [BB224×BB126] and ~190 bp for [BB225×BB187]. In the secondary PCR, the reaction volume was 100 μl, 5 μl of the gel-purified PCR products of the primary reactions were used as template, BB187 and BB126 were used as primers, and 4 units of Taq Polymerase and 0.25 units of Pfu Polymerase were employed. Otherwise, the reaction conditions were identical to those used in the primary reactions.

The substitution mutation A141C was constructed and sequence verified using the protocols detailed above for A136C with the following differences. Complementary mutagenic primers BB226 (5>ATGCCGGCCTTCT-GCTCTGCTCCAG>3; SEQ ID NO:33) and BB227 (5>CTGGAAAGCAGAGCAGAAGGCCGGCAT>3; SEQ ID NO:34), which change the GCC codon for A141 to a TGC codon for cysteine, replaced BB224 and BB225 respectively in the primary PCR reactions. The products of the primary reactions gave products of the expected sizes: ~180 bp for [BB226×BB 126] and ~205 bp for [BB227×BB 187].

The substitution mutation E93C was constructed using the technique of "mutagenesis by overlap extension". The primary PCR reactions for the E93C construction were performed in a 20 μl reaction volume in 1× Promega PCR buffer containing 1.5 mM MgCl$_2$, each primer at 0.5 μM, each of dATP, dGTP, dTTP and dCTP at 200 μM, 0.5 ng of template plasmid pBBT227, 2 units of Taq Polymerase (Promega), and 0.25 units of Pfu Polymerase (Stratagene). The reactions were performed in a Perkin-Elmer Gene-Amp® PCR System 2400 thermal cycler. The reaction program entailed: 95° C. for 3 minutes, 25 cycles of [94° C. for 60 seconds, 60° C. for 30 seconds, 72° C. or 45 in seconds] and a hold at 4° C. The primer pairs used were [BB218×BB211] and [BB219×BB210]. The reverse, non-mutagenic primer BB211 (5>GGCCATTCCCAGTTCTTC-CAT>3; SEQ ID NO:35) anneals to DNA sequences encoding amino acid residues 121-127 of mature G-CSF in pBBT227. The forward, non-mutagenic primer BB210 (5>TTC GTTTCTCTATCGCTACCAAC>3; SEQ ID NO:36) anneals to DNA sequences encoding amino acid residues 13-20 of the stII leader peptide in pBBT227. BB218 and BB219 are complementary mutagenic oligonucleotides that change the GAA codon for E93 to a TGT codon for cysteine. The sequence of BB218 is (5>CTGCAGGCCCT-GTGTGGGATCTCCCCC>3; SEQ ID NO:37) and the sequence of BB219 is (5>GGGGGAGATCCCACA-CAGGGCCTGCAG>3; SEQ ID NO:38). The products of the primary reactions were loaded directly onto a preparative 2% agarose gel which showed that PCR reactions gave products of the expected sizes: ~115 bp for [BB218×BB211] and ~325 bp for [BB219×BB210]. These fragments were excised from the gel, pooled, and eluted together from the agarose gel slices using a QIAquick Gel Extraction Kit (Qiagen) according to the vendor protocol and recovered in 30 µl 10 M Tris-HCl (pH 8.5). In the secondary PCR reaction, 5 i of the pool of gel-purified PCR products of the primary reactions was used as template and BB211 and BB210 were used as primers. The reaction volume was 100 µl and 4 units of Taq Polymerase and 0.25 units of Pfu Polymerase were employed. Otherwise, the reaction conditions were identical to those used in the primary reactions. An aliquot of the secondary PCR was analyzed by agarose gel electrophoresis, and the expected band of ~415 bp was observed. The bulk of the secondary PCR reaction was "cleaned up" using the QIAquick PCR Purification (Qiagen) and digested with Sty I and Xho I (New England BioLabs) according to the vendor protocols. Following an additional clean up using the QIAquick PCR Purification Kit, the digestion products were ligated with pBBT227 that had been cut with Sty I and Xho L treated with calf intestinal alkaline phosphatase (New England BioLabs) and gel purified. The ligation reaction was used to transform *E. coli* and plasmids from resulting transformants were sequenced to identify a clone containing the E93C mutation and having the correct sequence throughout the ~260 bp Sty I-Xho I segment The substitution mutation S96C was constructed and sequence verified using the protocols detailed above for E93C with the following differences. Complementary mutagenic primers BB220 (5>CTG AAA GGG ATC TGC CCC GAG TTG GGT>3; SEQ ID NO:39) and BB221 (5>ACC CAA CTC GGG GCA GAT CCC TTC CAG >3; SEQ ID NO:40), which change the TCC codon for S96 to a TGC codon for cysteine, replaced BB218 and BB219 respectively in the primary PCR reactions. The products of the primary reactions gave products of the expected sizes: ~110 bp for [BB220×BB211] and ~330 bp for [BB221× BB210].

For expression in *E. coli* as proteins secreted to the periplasmic space, the STII-G-CSF (C17S) genes encoding the muteins were excised from the pUC18-based pBBT227 derivatives as Nde I-Eco RI fragments of ~600 bp, subcloned into the pCYB1 expression vector, and transformed into *E. coli* W3110.

Using procedures similar to those described here, one can construct other cysteine muteins of G-CSF and G-CSF (C17S). The cysteine muteins can be substitution mutations that substitute cysteine for a natural amino residue in the G-CSF coding sequence, insertion mutations that insert a cysteine residue between two naturally occurring amino acids in the G-CSF coding sequence, or addition mutations that add a cysteine residue preceding the first amino acid, Ti, of the G-CSF coding sequence or add a cysteine residue following the terminal amino acid residue, P174, of the G-CSF coding sequence. The cysteine residues can be substituted for any amino acid, or inserted between any two amino acids, anywhere in the G-CSF coding sequence. Preferred sites for substituting or inserting cysteine residues in G-CSF are in the region preceding Helix A, the A-B loop, the B-C loop, the C-D loop, and the region distal to Helix D. Other preferred sites are the first or last three amino acids of the A, B, C, and D Helices. In addition to the mutations described above, other preferred residues in these regions for creating cysteine substitutions are P2, G4, P5, S8, L9, P10, Q11, S12, T38, K40, S53, G55, 156, W58, A59, P60, L61, S62, S63, P65, S66, Q67, A68, Q70, A72, Q90, A91, L92, G94, I95, S96, E98, G100, G125, M126, A127, Q131, Q134, G135, S142, A143, Q145, and P174. All of the variants described in this Example are provided in the context of the natural protein sequence or a variant protein in which the naturally occurring "free" cysteine residue (cysteine-17) has been changed to another amino acid, preferably serine or alanine.

One also can construct G-CSF and G-CSF (C17S) muteins containing a free cysteine by substituting another amino acid for one of the naturally occurring cysteine residues in G-CSF that normally forms a disulfide bond. The naturally occurring cysteine residue that normally forms a disulfide bond with the substituted cysteine residue is now free. The cysteine residue can be replaced with any of the other 19 amino acids, but preferably with a serine or alanine residue. These variants are provided in the context of the natural protein sequence or a variant protein in which the naturally occurring "free" cysteine residue (cysteine-17) has been changed to another amino acid, preferably serine or alanine. A free cysteine residue also can be introduced into G-CSF by chemical modification of a naturally occurring amino acid using procedures such as those described by Sytkowski et al. (1998).

Using procedures similar to those described in Examples 8, 9, 10, 11 and 13, one can express the proteins in *E. coli*, purify the proteins, PEGylate the proteins and measure their bioactivities in in vitro and in vivo bioassays. The proteins can be expressed cytoplasmically in *E. coli* or as proteins secreted to the periplasmic space. The muteins also can be expressed in eukaryotic cells such as insect or mammalian cells, using procedures similar to those described in PCT/US00/00931, or related procedures well known to those skilled in the art. If secretion from eukaryotic cells is desired, the natural G-CSF signal sequence, or another signal sequence, can be used to secrete the proteins from eukaryotic cells.

B. Expression and Purification of G-CSF (C17S) Cysteine Muteins. *E. coli* strains expressing 13 G-CSF (C17S) muteins (*-1C, TiC, L3C, A6C, S7C, E93C, A129C, T133C, A136C, A136C, A139C, A141C, Q173C, and *175C) were grown, induced and harvested using the protocols described in Example 8 that were employed for BOB213 (wild type) and BOB268 (C17S). All of the muteins were largely insoluble. The muteins were refolded and purified using the protocols described in Example 8 for G-CSF wild type and G-CSF (C17S). Non-reducing SDS-PAGE analysis revealed that the 13 purified cysteine muteins were recovered predominantly as monomers, migrating at approximately 17 kDa The purified muteins comigrated with wild type G-CSF and G-CSF (C17S), with the exception of the *-IC mutein, which migrated slightly slower than wild type G-CSF. All but one of the muteins eluted from the ion-exchange column at a salt concentration similar to wild type G-CSF and G-CSF (C17S). The one exception, E93C, eluted later during the gradient (NaCl concentration of approximately 400 mM), possibly due to the substitution of cysteine for the charged amino acid, glutamic acid.

C. Bioactivities of G-CSF (C17S) Cysteine Muteins. The 13 purified G-CSF (C17S) cysteine muteins were assayed in the NFS60 cell proliferation assay described in Example 8. Protein concentrations were determined using a Bradford protein assay kit (Bio-Rad Laboratories). Commercial wild type G-CSF and wild type G-CSF and G-CSF (C17S) prepared by us were analyzed in parallel on the same days to control for interday variability in the assays. All 13 muteins stimulated proliferation of the NFS60 cells to the same extent as the wild type G-CSF control proteins, within the error of the assay. Mean $EC_{50}$s for the 13 muteins ranged from 5-9 pg/ml. Mean $EC_{50}$s for the cysteine muteins were similar to the mean $EC_{50}$ of the G-CSF (C17S) control protein and 1.5 to 2-fold lower, i.e., more potent, than the mean $EC_{50}$ for our 5 wild type G-CSF control protein and ~3-fold lower than the mean $EC_{50}$ for the commercial wild type G-CSF protein. These data are summarized in Table 6.

TABLE 6

Bioactivities of Wild Type G-CSF, G-CSF (C17S) and G-CSF (C17S) Cysteine Muteins

| G-CSF Protein | Mutation Location | Mean EC$_{50}$ (pg/ml) | EC$_{50}$ Range[1] (pg/ml) |
|---|---|---|---|
| R&D G-CSF[2] | — | 18.6 +/− 6.6 | 12-35 (N = 12) |
| BBT G-CSF[3] | — | 10.2 +/− 1.6 | 8.5-13 (N = 8) |
| G-CSF (C17S) | — | 7.2 +/− 2.0 | 5-12 (N = 18) |
| *-1C/C17S | N-terminus | 7.0 | 5.8, 6.0, 7.5, 8.5 |
| T1C/C17S | N-terminus | 7.8 | 4.5, 5.0, 9.0, 10 |
| L3C/C17S | Proximal to A Helix | 8.0 | 4.5, 7.5, 9.0, 9.0, 10 |
| A6C/C17S | Proximal to A Helix | 8.2 | 4.5, 9.0, 11 |
| S7C/C17S | Proximal to A Helix | 7.3 | 3.8, 8.0, 10 |
| E93C/C17S | B-C loop | 7.6 | 6.5, 7.5, 8.0, 8.5 |
| A129C/C17S | C-D loop | 6.0 | 6.0, 6.0, 6.0 |
| T133C/C17S | C-D loop | 6.6 | 5.0, 6.0, 6.5, 7.5, 8.0 |
| A136C/C17S | C-D loop | 8.3 | 7.0, 7.5, 8.5, 10 |
| A139C/C17S | C-D loop | 5.2 | 5.0, 5.0, 5.5 |
| A141C/C17S | C-D loop | 8.9 | 7.5, 8.5, 9.5, 10 |
| Q173C/C17S | Distal to D Helix | 6.2 +/− 1.3 | 5.2-9.0 (N = 7) |
| *175C/C17S | C-terminus | 5.6 | 5.0, 5.5, 5.5, 6.0, 6.0 |

[1]EC$_{50}$ values from individual experiments; a range is shown when N>5
[2]Commercial wild type G-CSF (R&D Systems)
[3]Wild type G-CSF prepared by Bolder BioTechnology, Inc.

D. Construction of G-CSF double cysteine mutants

Multiple mutants containing two or more added free cysteine residues can be constructed either by sequential rounds of mutagenesis using the procedures described in Examples 9, 14 and 15, or alternatively by in vitro recombination of individual mutants to construct recombinant expression plasmids encoding muteins containing two or more free cysteine residues. The preferred multiple mutants would be those that combined two or more cysteine muteins that each retained high activity when PEGylated. Examples would be L3C plus T133C, L3C plus *175C, and T133C and *175C. Other preferred multiple mutants can be deduced based on the data from Table 3 and Table 4, and would include combinations containing two or more mutations selected from the group consisting of L3C, T133C, A141C and *175C.

We constructed the following G-CSF double cysteine mutants: L3C/T133C, L3C/*175C, and T133C/*175C. To produce L3C/T133C, the L3C derivative of pBBT227 (G-CSF C17S in pUC18) was digested with Xho I and EcoR I and treated with Calf Intestine Alkaline Phosphatase. The DNA was extracted using the Qiagen PCR cleanup kit, and is called G-CSF L3C X-R1-Cip vector. Next, the T133C derivative of pBBT227 was digested with Xho I and EcoR I, and the 480 bp fragment was gel purified and ligated with the G-CSF L3C X-R1-Cip vector. E. coli JM109 was transformed with the ligation reaction and clones having the correct sequence were identified.

To produce L3C/*175C, the *175C derivative of pBBT227 was digested with Xho I and EcoR I, and the ~480 bp fragment was gel purified and ligated with the G-CSF L3C X-R1-Cip vector (see above). E. coli JM109 was transformed with the ligation reaction and clones having the correct sequence were identified.

To produce T133C/*175C, the T133C derivative of pBBT227 served as template in a PCR reaction using the reverse mutagenic oligonucleotide primer BB186 (5>CGC GAA TTC TTA ACA GGG CTG GGC AAG GTG GCG TAG>3; SEQ ID NO: 14) and the forward non-mutagenic oligonucleotide BB125, which anneals to pUC18 vector sequences upstream of the G-CSF insert. The PCR was a 50 µl reaction performed in 1X Promega PCR buffer containing 1.5 mM MgCl$_2$, each primer at 0.4 µM, each of dATP, dGTP, dTTP and dCTP at 200 µM, 0.5 ng of template fragment, 1 unit of Taq Polymerase (Promega), and 0.1 unit of Pfu Polymerase (Stratagene). The reaction was performed in a Perkin-Elmer GeneAmp® PCR System 2400 thermal cycler. The reaction program entailed: 95° C. for 5 minutes, 22 cycles of [94° C. for 30 seconds, 55° C. for 30 seconds, 72° C. for 45 seconds], a 7 min hold at 72° C. and a hold at 4° C. Twenty µl of the PCR were analyzed by agarose gel electrophoresis, and the 630 bp fragment was isolated from the gel. This fragment was digested with Xho I and EcoR I, extracted using the Qiagen PCR cleanup kit. This DNA was ligated to a vector prepared by digesting the T133C derivative of pBBT227 with Xho I and EcoR I, treating with Calf Intestine Alkaline Phosphatase and extracting using the Qiagen PCR cleanup kit. E. coli JM109 was transformed with the ligation reaction and clones having the correct sequence were identified.

Example 10

PEGylation, Purification and Bioactivity of G-CSF Cysteine Muteins

A. Preliminary PEGylation studies. Initial PEGylation reaction conditions were determined using T1C as the test protein, TCEP [Tris (2-carboxyethyl) phosphine]-HCl as the reducing agent and 5 kDa cysteine reactive PEGs from Shearwater Polymers, Inc. Over-reduction of the protein was monitored by non-reducing SDS-PAGE, looking for a shift to a higher than expected apparent molecular weight as a result of protein unfolding, or for the appearance of multiple PEGylated species generated as the result of native disulfide reduction. One µg aliquots of purified TiC were incubated with increasing concentrations of TCEP at room temperature in 100 mM Tris, pH 8.5 in the presence of varying amounts of excess 5 kDa maleimide-PEG or 5 kDa vinylsulfone-PEG. After 60 min, the reactions were immediately analyzed by non-reducing SDS-PAGE. The amounts of TCEP and particular PEG reagent that yielded significant amounts of monoPEGylated TIC protein, without modifying wild type G-CSF, were used for further experiments. The titration experiments indicated that at pH 8.5, a 10-fold molar excess of TCEP and 20-fold excess of 5 kDa maleimide PEG yielded significant amounts of monoPEGylated TIC protein (apparent molecular weight of 28 kDa by SDS-PAGE) without detectable di- or tri-PEGylated protein. Wild type G-CSF and G-CSF (C17S) were not modified under identical PEGylation conditions. These reaction conditions were used to scale up the PEGylation of the other G-CSF muteins. Control experiments indicated that the TIC protein needed to be partially reduced by treatment with a reductant such as TCEP in order to be PEGylated.

B. Preparation and Purification of PEGylated G-CSF Cysteine Muteins: Aliquots of 200 to 300 µg of the 13 purified G-CSF cysteine muteins were PEGylated with a 5 kDa maleimide PEG to provide sufficient material for purification and characterization. The larger PEGylation reactions also were performed for 1 hr at room temperature, using the conditions described above. These reaction conditions yielded monoPEGylated protein for all of the muteins. Eleven of the monoPEGylated muteins have been purified using the procedure described below. At the end of the reaction time, the PEGylation mixture was diluted 10x with 40 mM sodium phosphate (monobasic) and the pH adjusted to 4.0 before being loaded quickly onto an S-Sepharose column (1 mL, HiTrap) using conditions similar to those described for the initial purification of the G-CSF muteins (20 mL gradient, 0-0.5 M NaCl in 40 mM sodium phosphate pH 4). The presence of the PEG moiety decreased the protein's affinity for the resin, allowing the PEGylated protein to be separated from the non-PEGylated protein. The chromatograms from the S-Sepharose columns showed two major protein peaks eluting at approximately 275 mM NaCl and 300-325 MM NaCl for most muteins. The early eluting major peak was determined to be the mono-PEGylated G-CSF (C17S) mutein by SDS-PAGE. The later eluting major peak was determined to be the unreacted G-CSF (C17S) mutein. The PEG-E93C mutein eluted at about 325 mM NaCl versus about 400 mM NaCl for unreacted E93C protein. Fractions from the early eluting peak containing predominantly the monoPEGylated G-CSF (C17S) mutein were pooled and used for bioactivity measurements. Five cysteine muteins (L3C, T133C, A141C, Q173C and *175C) also were PEGylated using a 20 kDa PEG-maleimide and the PEGylation and purification procedures described above. The 20 kDa-PEGylated proteins eluted from the S-Sepharose column at approximately 250 mM NaCl. SDS-PAGE analyses indicated that the purified PEGylated proteins contained less than 10%, and probably less than 5%, unPEGylated protein. The cysteine muteins needed to be partially reduced by treatment with a reductant such as TCEP in order to be PEGylated. Wild type G-CSF and G-CSF (C17S) did not PEGylate under identical partial reducing conditions, indicating that the PEG moiety is attached to the cysteine residue introduced into the muteins.

C. Purification and PEGylation of the L3C G-CSF Cysteine Mutein: Time courses of the refold and the PEGylation reactions for L3C were performed. The refold for this particular mutein was found to be complete by 4 hours. The refold reaction progression was monitored by reverse phase HPLC (C4 column). Yields were 10 mg/400 mL of culture grown as described in Example 8. Time courses were performed for the PEGylation of the L3C mutein with 10 kDa, 20 kDa and 40 kDa PEGs. PEGylation reaction conditions were as described above in Example 10, with the exeception that 0.5 mM EDTA was included in the PEGylation buffers. For 0.5-1 mg reactions, longer reactions times of 2-4 h at room temperature yielded greater amounts of PEGylated product The efficiencies of PEGylation was ~80% with the extended time. Larger (up to 5 mg) PEGylation reactions were performed with equal efficiency. PEGylated protein was purified from non-PEGylated protein on a 5 mL S-Sepharose column using the purification methodology previously described in Example 10. The 20 kDa PEGylated protein eluted at 200 mM NaCl, while the 40 kDa-PEG protein and 10 kDa-PEG protein eluted at ~150 mM and ~220 mM, respectively. The unPEGylated G-CSF L3C mutein eluted at ~260 mM. The presence of EDTA significantly reduced the formation of protein diners in the PEGylation reaction.

D. N-terminal sequencing of 20 kDa-PEG-L3C. The N-terminal amino acid of natural G-CSF is threonine (Souza et al., 1986). N-terminal sequencing of the purified 20 kDa-PEG-L3C protein using automated Edman degradation chemistry yielded the sequence TPXGPAS, which indicates that the N-terminus is correctly processed and is consistent with the third residue being PEGylated; PEGylated amino acids show up as blanks in sequencing runs, as indicated by the X.

E. Structural Determination of PEGylated G-CSF Cysteine Muteins by Circular Dichroism (CD) Analysis: CD analysis was performed on a Jasco 720 CD spectropolarimeter in a 1 cm pathlength 300 μL cell at ambient temperature. Data were collected from 260 nm-200 nm at a sensitivity of 50m° and 32 accumulations. Initial experimentation was performed with the L3C mutein and 10K PEG-L3C protein. Both had CD spectra very similar to that found in the literature for wild-type G-CSF. Similar analyses can be performed on other G-CSF cysteine muteins and their PEGylated derivatives.

F. Bioactivities of PEGylated G-CSF (C17S) Cysteine Muteins: Biological activities of the 11 purified 5 kDa-PEG-G-CSF (C17S) cysteine muteins and 5 purified 20 kDa-PEG-G-CSF (C17S) cysteine muteins were measured in the NFS60 cell proliferation assay described in Example 8. Concentrations of the proteins were determined using a Bradford dye binding assay. All of the PEGylated G-CSF (C17S) cysteine muteins showed similar dose-response curves and reached the same level of maximal growth stimulation as G-CSF (C17S), within the error of the assay. Mean $EC_{50}$s for the 5 kDa-PEG modified cysteine muteins ranged from 2-11 pg/ml. These PEGylated muteins were 1.5- to 2-fold more potent than our wild type G-CSF and 3-fold more potent than the commercial wild type G-CSF in the bioassay. Mean $EC_{50}$s for the 20 kDa-modified cysteine muteins ranged from 9 to 14 pg/ml. Biological activities of the PEGylated G-CSF (C17S) cysteine muteins were equal to, or superior to, that of wild type G-CSF. All of the NFS60 cell stimulatory activity of 5 kDa-PEG-L3C could be abolished by a neutralizing monoclonal antibody to G-CSF (R & D Systems, Inc.), indicating that the growth promoting activity is due to the PEG-L3C G-CSF protein and not to a contaminant in the protein preparation. The bioactivity data are summarized in Table 7. The $EC_{50}$ of L3C modified with a 40 kDa-PEG was determined to be 30-50 pg/ml using the NFS60 cell proliferation assay.

Biological activities of the PEGylated G-CSF (C17S) cysteine muteins described here are superior to the activities of previously described PEGylated G-CSF proteins, all of which have biological activities that are reduced relative to wild type G-CSF (Tanaka et al., 1991; Kinstler et al., 1996a; Bowen et al., 1999). Tanaka et al. (1991) reported that G-CSF modified with an amine-reactive 10 kDa NHS-PEG consisted of multiple molecular weight species and multiple isoforms modified at different lysine groups or the N-terminal amino acid. Biological activity of this NHS-PEG mixture was determined to be reduced approximately 3-fold relative to unmodified G-CSF (Tanaka et al., 1991; Satake-Ishikawa et al., 1992). Bowen et al. (1999) reported that a G-CSF variant modified with 5 kDa-, 10 kDa- and 20 kDa-amine-reactive PEGs were reduced approximately 6-fold, 10-fold and 20-fold relative to unmodified G-CSF. Bowen et al. (1999) purified a single molecular weight species of the PEGylated G-CSF variant modified with a 20 kDa-amine-reactive-PEG and found that its biological activity was reduced approximately 4-fold relative to unmodified G-CSF. Although the single molecular weight species isolated by Bowen et al. (1999) corresponded to the G-CSF variant modified with a single PEG molecule, the PEG-protein preparation was heterogeneous due to the PEG molecule being attached to the protein at multiple sites. Kinstler et al. (1996) purified a PEGylated Met-G-CSF species that is modified preferentially at the non-natural amino-terminal methionine residue of *E. coli*-expressed Met-G-CSF (cytoplasmically expressed) via amine or amide linkages. This PEGylated Met-G-CSF protein possessed only 68% of the in vitro bioactivity of wild type Met-G-CSF (Kinstler et al., 1996).

TABLE 7

Bioactivities of PEGylated G-CSF Cysteine Muteins

| | $EC_{50}$s (pg/ml) | | | |
|---|---|---|---|---|
| | 5 kDa PEG | | 20 kDa PEG | |
| G-CSF Protein | Mean | Range[1] | Mean | Range[a] |
| *-1C/C17S | 5.6 | 5.5, 5.5, 5.5, 6.0 | | |
| T1C/C17S | 7.0 | 6.0, 7.0, 8.0 | | |
| L3C/C17S | 5.5 | 5.0, 5.3, 6.2 | 8.8 | 8.0, 8.0, 9.0, 10 |
| A6C/C17S | 6.9 | 6.0, 6.0, 7.5, 8.0 | | |
| S7C/C17S | 2.4 | 1.7, 3.0 | | |
| E93C/C17S | 1.9 | 1.6, 2.0, 2.0, 2.0 | | |
| A129C/C17S | 7.1 | 5.0, 5.2, 11 | | |
| T133C/C17S | 7.4 | 5.2, 6.0, 11 | 9.0 | 6.0, 7.0, 11, 12 |
| A136C/C17S | 6.9 | 6.0, 6.5, 6.5, 8.5 | | |
| A139C/C17S | 6.8 | 5.0, 5.5, 10 | | |
| A141C/C17S | 7.1 | 6.5, 7.0, 7.0, 8.0 | 9.3 | 6.0, 6.0, 12, 13 |
| Q173C/C17S | 7.0 | 5.5, 5.5, 10 | 11 | 9.0, 10, 12, 13 |
| *175C/C17S | 11 | 10, 11, 12 | 14 | 12, 12, 16, 16 |

[a]$EC_{50}$ values from individual experiments

Example 11

Use of A Cysteine Blocking Agent Improves Recovery of Properly Folded G-CSF Cysteine Muteins Insoluble, *E. coli*-expressed wild type G-CSF and G-CSF (C17S/Q173C) were refolded by procedures that varied the amount and type of reducing agent and the presence or absence of catalytic amounts of copper sulfate. 5 mM dithiothreitol (DTT) was chosen as the standard reducing agent based on a literature reference that describes its use in an optimized refold protocol for G-CSF (Kuga et al., 1989). Lu et al. (1992) describes a protocol for refolding/renaturing insoluble G-CSF that has no reducing agent present during the solubilization step but does contain 40 μM copper sulfate in the renaturation buffers.

*E. coli* cultures (400 mL) were grown and expression of each G-CSF protein was induced as described in Example 8. The cells were lysed and the insoluble portion was isolated by centrifigation as described in Example 8. The insoluble material, which contained a majority of the insoluble G-CSF proteins, was suspended in 20 mL of 8 M urea, 20 mM Tris, pH 8 and stirred until homogeneous. The mixture was aliquotted into 6 tubes. 5 mM DTT or 25 mM cysteine were added to certain of the tubes as described in Table 6. After one hour the solublization mixtures were diluted into 25 mL of 40 mM sodium phosphate, 15% glycerol, pH 8 with and without 40 μM copper sulfate The refolds were allowed to sit at 4° C. for two days. At this time the pH of each was adjusted to 4. The refolds were centrifuged, the supernatants loaded onto an S-Sepharose column and the G-CSF wild type and Q173C proteins purified as described in Example 8. Column fractions were pooled based on non-reducing SDS-PAGE analysis, as described in Example 8. The amount of each protein recovered after chromatography is shown in Table 5.

TABLE 8

Recoveries of G-CSF Proteins Refolded/Renatured in the Presence And Absence of Different Reducing Agents

| Refold Protocol | Reducing Agent | Copper Sulfate | G-CSF (WT) Yield (μg)[a] | G-CSF (C17S/Q173C) Yield (μg)[a] |
|---|---|---|---|---|
| A | None | None | 49 | 161 |
| B | None | 40 μM | 24 | 73 |
| C | 5 mM DTT | None | 17 | 23 |
| D | 5 mM DTT | 40 μM | 47 | 53 |
| E | 25 mM cysteine | None | 60 | 243 |
| F | 25 mM cysteine | 40 μM | 80 | 275 |

[a]Protein recovered from 67 ml of *E. coil* culture

As shown in Table 8 the greatest yields of G-CSF wild type and the G-CSF cysteine mutein were achieved when cysteine was used as the reducing agent during the solubilization step. The presence of copper sulfate (40 μM) appeared to marginally enhance recoveries when used in conjunction with a reducing agent Non-reducing SDS-PAGE analysis of wild type G-CSF proteins recovered using Refold protocols A-F showed that each contained predominantly a single molecular weight species of the size expected for monomeric G-CSF (approximately 17 kDa under non-reducing conditions). In contrast, when the S-Sepharose column pools from G-CSF (C17S/Q173C) Refolds A-D were analyzed by non-reducing SDS-PAGE, the final product band was broad and contained a number of different apparent molecular weight species in the monomeric range. Presumably the different molecular weight, monomeric species represent different disulfide isoforms of the G-CSF (C17S/Q173C) protein. The G-CSF (C17S/Q173C) protein recovered from refolds E and F ran as a single sharp band that comigrated with wild type G-CSF, indicating that a single, predominant folded species had been recovered. The data show that addition of cysteine during the solubilization and refolding steps significantly enhances the yield of properly folded G-CSF (C17S/Q173C) protein. Although not wishing to be bound by any particular theory, we postulate that the added cysteine forms a mixed disulfide with the free cysteine residue in the mutein. The mixed disulfide limits possible disulfide rearrangements that could occur involving the free cysteine residue. Cysteine may be more effective than DTT because DTT typically does not form mixed disulfides due to a thermodynamically preferred intramolecular bond that forms upon oxidation.

Example 12

Comparison of G-CSF Protein Stabilities Prepared in the Presence and Absence of Cysteine Wild type G-CSF and G-CSF (C17S/Q173C) proteins prepared as described in Example 11 using Refold procedure A (no reducing agent, no copper sulfate) and Refold procedure F (25 mM cysteine, 40 μM copper sulfate) were placed at 50° C. at pH 4 and pH 8. At times 0, 5 minutes, 30 minutes, 1, 2, 3, 4, 5, and 20 hours, the protein samples were centrifuged to remove any denatured protein precipitates. Aliquots were removed from the supernatants and frozen. At the end of the experiment, all aliquots were analyzed by non-reducing SDS-PAGE to determine what portion of the original G-CSF protein sample remained in solution and was monomeric. Each protein's soluble half-life was determined based on relative band intensities as visualized on the gel. The results are shown in Table 9.

TABLE 9

Stabilities of G-CSF Proteins Prepared Using Different Refold/Renaturation Procedures

| Protein Sample | pH | Estimated Half-life |
|---|---|---|
| G-CSF WT Refold A | 4 | 3-4 hours |
| G-CSF WT Refold F | 4 | 3-4 hours |
| G-CSF WT Refold A | 8 | ~1 hour |
| G-CSF WT Refold F | 8 | ~1 hour |
| G-CSF (C17S/Q173C) Refold A | 4 | ~30 minutes |
| G-CSF (C17S/Q173C) Refold F | 4 | >20 hours |
| G-CSF (C17S/Q173C) Refold A | 8 | <15 minutes |
| G-CSF (C17S/Q173C) Refold F | 8 | >20 hours |

The results show that wild type G-CSF has a longer soluble half-life at pH 4 than at pH 8, which is consistent with results previously reported by Arakawa et al.(1993). The soluble half-life of wild type G-CSF was not substantially different whether the protein was refolded using Refold Procedure A or F. In contrast, G-CSF (C17S/Q173C) had a much longer soluble half-life when the protein was refolded using Procedure F (>20 hours) rather than Procedure A (<30 minutes). Thus, in addition to increasing the recovery of properly folded G-CSF cysteine muteins, use of cysteine in the solubilization/refolding process increases the thermal stability of the final product.

Additional studies can be performed to compare the stabilities of G-CSF cysteine muteins to wild type G-CSF. For example, a matrix of experiments can be performed by exposing the proteins to various pHs, temperatures and serum concentrations. At various time points, the intregrity of the proteins can be monitored by assays such as, but not limited to, the NFS60 in vitro cell proliferation bioactivity assay described in Example 8, size exclusion chromatography, Circular Dichroism, ELISA assays and Western blot analysis.

Example 13

In Vivo Efficacy of PEG-G-CSF Cysteine Muteins

Groups of three male Sprague Dawley rats, weighing 320 g each, received a single intravenous injection (lateral tail vein) of wild type recombinant G-CSF (prepared by Bolder BioTechnology), Neupogen® (a recombinant G-CSF sold by Amgen, Inc.) or PEG-L3C at a dose of 100 μg/kg. Protein concentrations were determined using a Bradford dye binding assay. At selected time points blood samples (0.3 to 0.4 ml) were drawn from the rats into EDTA anti-coagulant tubes. Aliquots of the blood samples were sent to a commercial firm for a complete blood cell (CBC) count. The remainder of the blood sample was centrifuged and the plasma frozen at −80° C. Blood samples were drawn at 0.25, 1.5, 4, 8, 12, 16, 24, 48, 72, 96, 120 and 144 h post-injection. A 0 h baseline sample was obtained 24 h prior to injection of the test compounds. Tables 10 and 11 show the mean blood neutrophil and total white blood cell counts for the different test groups over time. All three test compounds stimulated an increase in peripheral white blood cells and neutrophils over baseline values. White blood cell and neutrophil counts for the test groups receiving wild type recombinant G-CSF and Neupogen® peaked ~24 h post-injection and returned to baseline values by ~48 h. In contrast, white blood cell and neutrophil counts for the rats receiving PEG-L3C peaked ~48-72 h post-injection and did not return to baseline values until ~120 h post-injection.

Peak white blood cell and neutrophil levels observed in the rats receiving PEG-L3C were significantly higher than for the groups receiving wild type recombinant G-CSF or Neupogen® ($p<0.05$). The data indicate that PEG-L3C is capable of stimulating an increase in circulating neutrophil and white blood cells, and that the absolute increase in peripheral white blood cell counts and neutrophils is greater and longer lasting than that seen with wild type G-CSF or Neupogen®. Similar experiments can be performed to demonstrate efficacy of other PEGylated G-CSF cysteine muteins (C17 or C17S versions). Similar studies also can be performed using the subcutaneous route for administration of the proteins.

TABLE 10

Effects of G-CSF, Neupogen ® and PEG-L3C on Neutrophil Blood Cell Counts Following Single Intravenous Administration of the Proteins (100 μg/kg)

| Time (Hr) | Neutrophils Mean +/− SE (cells/μl blood) | | |
|---|---|---|---|
| | G-CSF[a] | Neupogen | PEG-L3C |
| 0 | 1,147 +/− 167 | 1,906 +/− 564 | 1,596 +/− 462 |
| 4 | 6,752 +/− 923 | 4,504 +/− 549 | [b]4,237 +/− 624 |
| 8 | 8,437 +/− 546 | 5,525 +/− 894 | [b]5,939 +/− 664 |
| 12 | 10,744 +/− 549 | 11,891 +/− 1,545 | [b]8,470 +/− 833 |
| 24 | 11,035 +/− 788 | 11,148 +/− 977 | [b]14,849 +/− 1,398 |
| 48 | 2,355 +/− 218 | 2,610 +/− 245 | [b,c]18,488 +/− 2,954 |
| 72 | 2,113 +/− 438 | 3,077 +/− 590 | [b,c]17,353 +/− 2,515 |
| 96 | 2,086 +/− 496 | 2,675 +/− 673 | [b,c]5,467 +/− 914 |
| 120 | 2,179 +/− 373 | 2,063 +/− 469 | 2,390 +/− 238 |

[a]Wild type G-CSF prepared by Bolder BioTechnology, Inc.
[b]$p < 0.05$ versus 0 hour neutrophil levels
[c]$p < 0.05$ versus G-CSF and Neupogen at same time point

TABLE 11

Effects of G-CSF, Neupogen ® and PEG-L3C on White Blood Cell Counts Following Single Intravenous Administration of the Proteins (100 μg/kg)

| Time (Hr) | White Blood Cells Mean +/− SE (cells/μl blood) | | |
|---|---|---|---|
| | G-CSF[a] | Neupogen | PEG-L3C |
| 0 | 11,100 +/− 252 | 11,100 +/− 829 | 12,900 +/− 1,320 |
| 4 | 16,000 +/− 1,059 | 13,600 +/− 570 | 13,700 +/− 1,923 |
| 8 | 15,200 +/− 371 | 14,900 +/− 260 | 13,800 +/− 1,044 |
| 12 | 18,400 +/− 240 | 20,100 +/− 674 | [b]16700 +/− 586 |
| 24 | 23,900 +/− 1,110 | 25,500 +/− 1,734 | [b]29,200 +/− 2,321 |
| 48 | 14,700 +/− 426 | 15,300 +/− 1,715 | [b,c]37,400 +/− 4,971 |
| 72 | 15,300 +/− 426 | 14,800 +/− 764 | [b,c]37,800 +/− 4,715 |
| 96 | 14,200 +/− 1,000 | 14,700 +/− 689 | [b]18,100 +/− 2,550 |
| 120 | 11,000 +/− 2,651 | 11,300 +/− 1,477 | 13,800 +/− 1,189 |

[a]Wild type G-CSF prepared by Bolder BioTechnology, Inc.
[b]$p<0.05$ versus 0 hour white blood cell levels
[c]$p<0.05$ versus G-CSF and Neupogen at same time point Plasma G-CSF and PEGylated G-CSF cysteine mutein protein levels can be quantitated using commercially available G-CSF ELISA kits (R & D Systems, Inc.). Titration experiments can be performed to determine relative sensitivity of the ELISA for detecting wild type G-CSF, unmodified G-CSF cystein muteins and PEGylated G-CSF cysteine muteins. Similar studies can be performed using the subcutaneous of administration of the proteins.

Plasma concentrations of the proteins from the efficacy experiment outlined above in Example 13 were measured using human G-CSF ELISA kits purchased from R & D Systems, Inc. Results are shown in Table 12. The results indicate that 20 kDa-PEG-L3C has a significantly longer circulating half-life than wild type G-CSF or Neupogen® following intravenous administration of the proteins to rats.

TABLE 12

Plasma concentrations of G-CSF, Neupogen® and 20 kDa-PEG-L3C Following a Single Intravenous Administration of the Proteins (dose of 100 µg/kg)

| Time Post-injection (hour) | G-CSF[a] (ng/ml) Mean +/− S.D. | Neupogen (ng/ml) Mean +/− S.D. | 20 kDa-PEG-L3C (ng/ml) Mean +/− S.D. |
|---|---|---|---|
| 0 | 0 +/− 0 | 0 +/− 0 | 0 +/− 0 |
| 0.25 | 6,974 +/− 1,809 | 7,546 +/− 486 | 9,667 +/− 1,382 |
| 1.5 | 1,866 +/− 292 | 2,083 +/− 461 | 8,368 +/− 1,215 |
| 4 | 399 +/− 73 | 534 +/− 131 | 7,150 +/− 892 |
| 8 | 101 +/− 21 | 167 +/− 26 | 5,692 +/− 1,094 |
| 12 | 14 +/− 5 | 26 +/− 1.1 | 4,165 +/− 783 |
| 16 | 2 +/− 3 | 2.9 +/− 0.5 | 3,669 +/− 513 |
| 24 | 0.9 +/− 0.3 | 0.08 +/− 0.03 | 2,416 +/− 462 |
| 48 | 0.16 +/− 0.01 | 0 +/− 0 | 773 +/− 137 |
| 72 | 0.08 +/− 0.02 | 0 +/− 0 | 36 +/− 36 |
| 96 | 0.11 +/− 0.02 | 0 +/− 0 | 0.62 +/− 0.13 |
| 120 | 0.05 +/− 0.02 | 0 +/− 0 | 0.15 +/− 0.02 |
| 144 | 0.03 +/− 0.02 | 0 +/− 0 | 0.03 +/− 0.01 |

[a]Wild type G-CSF prepared by Bolder BioTechnology, Inc.

In vivo efficacy of the PEGylated G-CSF cysteine muteins (C17 or C17S versions) can be measured in normal or neutropenic rodents such as mice or rats by demonstrating that the proteins stimulate increases in circulating neutrophil levels and granulopoiesis compared to vehicle-treated animals. G-CSF stimulates neutrophil levels in normal and neutropenic rodents at a dose of 100 µg/kg (Kubota et al., 1990; Kang et al., 1995). For demonstrating efficacy in normal mice, groups of 5 mice (weighing ~20 g each) can receive subcutaneous injections of G-CSF, PEG-G-CSF cysteine muteins or placebo (vehicle solution) at specified intervals for up to five days. Normal mice such as ICR mice can be purchased from a commercial vendor. On day 6 the animals can be sacrificed and blood samples collected for complete blood cell count (CBC) analysis. Hematopoietic tissues (liver and spleen) can be collected, weighed and fixed in formalin for histopathologic analyses to look for evidence of increased granulopoiesis. Bone marrow can be removed from various long bones and the sternum for unit particle preps and histopathologic analysis to look for evidence of increased granulopoiesis. Comparisons between groups should be made using a Students T test for single comparisons and one-way analysis of variance for multiple comparisons. $P<0.05$ should be considered significant. The PEGylated G-CSF cysteine muteins should stimulate greater increases in circulating neutrophil levels and granulopoiesis in the mice compared to the vehicle-treated mice. Efficacy of the PEGylated G-CSF cysteine muteins modified with 5 kDa, 10 kDa, 20 kDa or 40 kDa PEGs can be tested when administered once, once per day, every other day, or every third day. In initial experiments, different groups of mice can receive subcutaneous injections of 0.0032, 0.016, 0.08, 0.4 and 2 µg per injection of the PEGylated G-CSF cysteine muteins. Control mice can receive vehicle solution only. Additional control groups can receive wild type G-CSF (2 µg/every day (ED) for 5 days) and 2 µg wild type G-CSF using the same dosing regimen as the PEGylated G-CSF cysteine muteins.

Efficacy of the PEGylated G-CSF cysteine muteins also can be demonstrated in neutropenic mice. Neutropenia can be induced by treatment with cyclophosphamide (CPA; 100 mg/kg), which is a commonly used myelosuppressive chemotherapeutic agent and relevant to the human clinical setting. G-CSF accelerates recovery of normal neutrophil levels in cyclophosphamide-treated animals (Kubota et al., 1990; Kang et al., 1995; Matsuzaki et al., 1996). Mice (20 g) can receive an intraperitoneal injection of cyclophosphamide on day 0 to induce neutropenia The animals should be divided into different groups, which should receive subcutaneous injections of G-CSF, PEGylated G-CSF cysteine muteins or placebo at specified intervals for up to five days. One control group should not receive cyclophosphamide but should receive placebo injections. Efficacy of the PEGylated G-CSF cysteine muteins modified with 5 kDa, 10 kDa, 20 kDa or 40 kDa PEGs can be tested when administered once, every other day, or every third day. In initial experiments, different groups of mice can receive subcutaneous injections of 0.0032, 0.016, 0.08, 0.4 and 2 µg per injection of the PEGylated G-CSF cysteine muteins. Control mice can receive vehicle solution only. Additional control groups can receive wild type G-CSF (2 µg/every day (ED) for 5 days) and 2 µg/injection of wild type G-CSF using the same dosing regimen as the PEGylated G-CSF cysteine muteins. On days 0-10, five mice per group can be sacrificed and blood and tissue samples analyzed as described for the normal mouse experiments above. The PEGylated G-CSF cysteine muteins should stimulate an accelerated increase in circulating neutrophil levels and granulopoiesis in the mice compared to the vehicle-injected, CPA-injected control group.

Alternatively, efficacy of PEGylated G-CSF cysteine muteins can be demonstrated in neutropenia studies using a rat model. G-CSF accelerates the recovery of normal neutrophil levels in rats treated with myleosuppressive chemotherapeutic agents. In this case, groups of Spague Dawley rats (weighing ~300 g each) can receive an intraperitoneal dose of CPA (100 mg/kg) at Day 0 to induce neutropenia. The animals can then be divided into three groups, those who receive subcutaneous injections of G-CSF, PEGylated G-CSF cysteine muteins or placebo at specified intervals for up to 10 days. One control group can receive placebo injections rather than cyclophosphamide. In initial experiments, efficacy of the PEGylated G-CSF cysteine muteins modified with 10 kDa, 20 kDa and 40 kDa PEGs can be measured by performing subcutaneous doses of ~0.1 µg-500 µg/kg (with the preferential range being 1-100 µg/kg) when doses are administered once, every day, every other day or every third day. An additional control group can receive commercially available wild type G-CSF (100 µg/kg) every day for 5 days and another control group can receive wild type G-CSF with the same dose and dosing regimen as with the PEGylated G-SCF cysteine mutants. Control rats can receive vehicle solution only. On days 0-6, 8, 10, 12, and 14 blood samples can be collected for CBC analysis. At the completion of the time course, the rats can be sacrificed for collection of the hematopoietic tissues and bone marrow to investigate evidence of increased granulopoiesis. The PEGylated G-CSF cysteine mutants should stimulate an accelerated increase in circulating neutrophil levels and granulopoiesis in the rats compared to the vehicle-injected, CPA injected control group.

Example 14

Cloning, Expression, Purification and Bioactivity of Wild Type GM-CSF

A. Cloning DNA sequences encoding GM-CSF. We cloned and sequenced a cDNA encoding human GM-CSF by RT-PCR of total RNA isolated from the human bladder carcinoma cell line 5637 (obtained from the American Type Culture Collection). A cDNA encoding G-CSF was amplified by PCR from total RNA isolated from the human bladder carcinoma cell line 5637 (American Type Culture Collection). The cells were grown in RPM11640 media supplemented with 10% FBS, 50 units/ml penicillin and 50 µg/ml streptomycin. RNA was isolated from the cells using an RNeasy Mini RNA isolation kit purchased from Qiagen, Inc. (Santa Clarita, Calif.) following the manufacturer's directions. First strand synthesis of single-stranded cDNA was accomplished using a 1st Strand cDNA Synthesis Kit for RT-PCR (AMV) from Boehringer Mannheim Corp and random hexamers were used as the primer. Subsequent PCR reactions using the products of the first strand synthesis as template were carried out with forward primer BB267 (5>GAC ACT GCT GCT GAG ATG AAT G>3; SEQ ID NO:75) and reverse primer BB268 (5>CTT GTA GTG GCT GGC CAT CAT G>3; SEQ ID NO:76). Primer BB268 anneals to the 5' end of the coding sequence for the GM-CSF secretion signal and the reverse primer, BB268, anneals to the 3' end of the GM-CSF coding sequence. The resulting ~450 bp PCR product was digested with Hind III and Bam HI, gel purified and cloned into pCDNA3.1(+) vector that had been digested with Hind III and Bam HI, alkaline phosphatase treated, and gel purified. A clone with the correct DNA sequence was designated pCDNA3.1(+)::GM-CSFfus or pBBT267. We used PCR to modify this GM-CSF clone for periplasmic expression in *E. coli*. When expressed in *E. coli*, via secretion to the periplasmic, GM-CSF does not contain an added N-terminal methionine and has an amino acid sequence identical to naturally occurring GM-CSF (Lee et al., 1985). In order to express a secreted form of GM-CSF, PCR was used to fuse the leader sequence of the *E. coli* heat-stable enterotoxin (STII) gene (Picken et al., 1983), proceeded by an Nde I restriction site, to the amino-terminal coding sequence of mature GM-CSF. In addition, a TAA stop codon, followed immediately by an Eco RI restriction site, was added following the carboxy-terminal residue, E127. At the same time, codons for prolines at positions 2, 6, 8, 12, 117 and 124 were all changed to CCG, and the codon for leucine at position 114 was changed to CTG. The PCR reaction used forward primer BB300 (5>CGC AAC GCG TAC GCA GCA CCG GCC CGC TCG CCG AGC CCG AGC ACG CAG CCG TGG GAG>3; SEQ ID NO:77) and reverse primer BB301 (5>CGC GAA TTC TTA CTC CTG GAC CGG CTC CCA GCA GTC AAA CGG GAT GAC CAG CAG AAA>3; SEQ ID NO:78) with pBBT267 as template. The resulting ~400 bp PCR product was digested with Mlu I and Eco RI, gel purified, and cloned into pBBT227 which is described in Example 9 above. pBBT227 DNA was digested with Mlu I and Eco RI, alkaline phosphatase treated, and run out on a 1% agarose gel. The ~2.4 kb vector fragment was purified and used in ligation. The resulting recombinants carry a complete stII leader fused to GM-CSF and this "stII-GM-CSF" construct can be excised as an Nde I-Eco RI fragment of ~450 bp. One clone with the correct sequence was designated pUC18:::stII-GM-CSF. For expression studies the Nde I-Eco RI fragment of this plasmid was subcloned into the expression vector pBBT257, which is described in below. The resulting plasmid, pBBT257; stII-muGM-CSF, or pBBT271 was introduced into *E coli* W3110 for expression.

The plasmid pBBT257 was derived from the expression vector pCYB1 (New England BioLabs) by deleting the ampicillin resistance gene of pCYB1 and replacing it with the gene for tetracycline resistance derived from the classic cloning vector pBR322 (Bolivar et al, 1977) In both pBBT257 and pCYB1, expression of the cloned gene is under the control of the tac promoter, which is regulated by the product of the plasmid-borne lacI^q^ gene These vectors allow genes to be expressed as unfused proteins or as fusions to a chitin binding domain; our constructs were created so that the proteins are expressed as unfused proteins. Plasmid pBBT257 was constructed as follows. The tetracycline resistance gene ($Tc^R$ gene) of plasmid pBR322 (purchased from New England bioLabs) was amplified by PCR using primers BB228 (5>CGC GCT GCA GTT CTC ATG TTT GAC AGC TTA TCA TC>3; SEQ ID NO:41) and BB229 (5>CGC GCT GCA G AT TTA AAT TAG CGA GGT GCC GCC GGC TTC CAT >3; SEQ ID NO:42). Forward primer BB228 anneals to nucleotides 1 through 25 of the pBR322 sequence (GenBank Accession # J01749), which are located upstream of the $Tc^R$ gene and include the "-35" portion of the $Tc^R$ gene promoter. Oligo BB228 contains an added Pst I site for cloning purposes. The reverse primer BB229 anneals to nucleotides 1277 through 1300, which are located immediately downstream of the translational stop codon that follows the coding sequence of the $Tc^R$ gene. BB229 contains an added Dra I site for cloning purposes. The 40 µl PCR reaction was performed in 50 mM KCl, 10 mM Tris-HCl (pH 9.0 @ 25° C. C), 0.1% Triton®D X-100, 1.5 mM $MgCl_2$ and included dNTPs at 200 µM each, 20 µmole of each primer, 0.5 ng of pBR322 DNA, 2.5 units of Taq polymerase (Promega), and 0.5 units of PFU polymerase (Stratagene). The PCR reaction consisted of: 95° C. for 3 minutes, 25 cycles of [94° C. for 30 seconds, 60° C. for 30 seconds, 72° C. for 90° seconds] followed by a 4° C. hold. The resulting 1300 bp product was gel purified, digested with Pst I and Dra I and used in a ligation reaction as described below. Purified pCYB 1 DNA was digested with Pst I and Swa I and treated with calf intestine alkaline phosphatase according to the vendor (New England BioLabs) protocols. Pst I and Swa I each cut the vector once and flank the ampicillin resistance ($Ap^R$) gene. The digestion products were cleaned up using a Qiaquick PCR Cleanup Kit (Qiagen) according to the vendor protocol and subsequently run out on a 1% agarose gel. The ~5.3 kb vector fragment, deleted for the $AP^R$ gene, was gel purified and ligated with the Pst I-Dra I cut PCR product containing the $Tc^R$ gene. Both Dra I and Swa I generate blunt-ended digestion products that can be ligated together. The ligation reaction was used to transform *E. coli* DH5α and tetracycline-resistant transformants were selected. Three isolates were subsequently analyzed and all were found to be sensitive to ampicillin. Restriction endonuclease digestion products obtained from these isolates were also consistent with deletion of the ~1500 bp Pst I and Swa I fragment containing the $Ap^R$ gene and its replacement by the ~1300 bp Pst I-Dra I fragment that carries the $Tc^R$ gene. One isolate, designated pBBT257, was chosen for use in expression of recombinant proteins.

B. Expression of Wild Type GM-CSF in *E. coli* For expression of secreted GM-CSF, pBBT271 [pBBT257:: STII-GM-CSF] and the pBBT257 parent vector, were transformed into *E. coli* W3110. The resulting strains were designated as BOB340: W3110(pBBT257) and BOB350: W3110(pBBT271). Fresh saturated overnight cultures were inoculated at ~0.05 OD @ $A_{600}$ in LB containing 10 μg/ml tetracycline. These 100 ml cultures were grown in a 500 mL baffled shake flask at 28° C. in a gyrotory shaker water bath at ~250 rpm. When the culture reached a density of ~0.6 OD, IPTG was added to a final concentration of 0.5 mM and the induced culture was then incubated overnight for 16 h. Samples of induced and uninduced cultures were analyzed by SDS-polyacrylamide gel electrophoresis (SDS-PAGE) on precast 16% Tris-glycine polyacrylamide gels and stained with Coomassie Blue. The induced culture of BOB350 (GM-CSF) gave a band at approximately 14 kDA, which is consistent with the mature GM-CSF molecular weight. This band was not detected in an uninduced culture of BOB350 or in induced or uninduced cultures of BOB340, the vector-only control. Western blot analyses showed that this ~14 kDa band reacted strongly with an anti-human GM-CSF antiserum (R&D Systems). This antiserum did not recognize proteins in uninduced cultures of BOB340 and BOB 350 or in the induced culture BOB340, the vector only control. These Western blots also showed that this 14 kDa band co-migrated with a commercial, *E. coli*-derived human GM-CSF standard purchased from R & D Systems. This result suggests that the STII leader peptide has been removed, which is consistent with the protein having been secreted to the periplasmic N-terminal sequencing studies presented below indicate the STII signal sequence was properly processed.

The 16 hour post-induction samples from these cultures also were subjected to osmotic shock based on the procedure of Koshland and Botstein (1980). This procedure ruptures the *E. coli* outer membrane and releases the contents of the periplasmic into the surrounding medium. Subsequent centrifugation separates the soluble periplasmic components (recovered in the supernatant) from cytoplasmic, insoluble periplasmic, and cell-associated components (recovered in the pellet). Little of the GM-CSF protein synthesized was recovered in the supernatant The bulk of the GM-CSF remained associated with the pellet This indicates that while the protein appears to be processed and secreted to the periplasmic, it accumulates there primarily in an insoluble form. Similar results have been reported by others for GM-CSF secreted to the *E coli* periplasmic (Libby et al., 1987; Greenberg et al., 1988).

C. Purification of Wild Type GM-CSF. Wild type GM-CSF was expressed and purified at a larger scale using the following protocols. A fresh saturated overnight culture of BOB350 (wild type) was inoculated at ~0.05 OD @ $A_{600}$ in LB containing 10 μg/ml tetracycline. The 400 ml culture was grown in a 2 L baffled shake flask at 28° C. in a gyrotory shaker water bath at ~250 rpm. When the culture reached a density of ~0.6 OD, IPTG was added to a final concentration of 0.5 mM. The induced culture was then incubated overnight for ~16 h. The cells were pelleted by centrifugation and frozen at −80° C. The cell pellet was thawed and treated with 5 mL of B-PER™ bacterial protein extraction reagent according to the manufacturer's (Pierce) protocols. The insoluble portion, and the bulk of the GM-CSF protein, was recovered by centrifugation and resuspended in B-PER This mixture was treated with lysozyme (200 μg/mL) for 10 min to further disrupt the cell walls, and $MgCl_2$ (10 mM final) and protease-free DNAse (2 μg/ml) were added. Insoluble GM-CSF was collected by centrifugation and washed, by resuspension in water and recentrifugation, to remove most of the solubilized cell debris. For refolding, the resulting pellet containing insoluble GM-CSF was dissolved in 10 ml of 8 M urea, 25 mM cysteine in 20 mM Tris Base. This mixture was stirred for 30 min at room temperature then diluted into 100 ml of 20 mM Tris, 40 μM copper sulfate, 15% glycerol, pH 8.0. This refold mixture was held at 4° C. for 2 days and then centrifuged and loaded onto a 5 ml Q-Sepharose column (Pharmacia HiTrap) equilibrated in 20 mM Tris, pH 8.0 (Buffer A). The bound proteins were eluted with a linear salt gradient from 0-35% Buffer B (IM NaCl, 20 mM Tris, pH 8). Column fractions were analyzed by non-reducing SDS-PAGE. GM-CSF eluted at approximately 230 mM NaCl. Fractions containing primarily GM-CSF were pooled.

The Q-Sepharose pool was diluted with an equal volume of 30% ammonium sulfate and warmed to room temperature before being loaded onto a 1 mL Phenyl HP column (Pharmacia HiTrap) previously equilibrated with 15% ammonium sulfate in 20 mM sodium phosphate, pH 7.5. Purified GM-CSF was recovered from the column by elution with a reverse salt gradient (15% ammonium sulfate to 0% ammonium sulfate in 20 mM sodium phosphate, pH 7.5). The Phenyl HP column elution profile for GM-CSF showed a single major peak, eluting at approximately 6.5% ammonium sulfate. Column fractions across the peak were analyzed by non-reducing SDS-PAGE. Fractions containing GM-CSF and no visible contaminants were pooled. The final yield of wild type GM-CSF as determined by Bradford analysis, was about 2.6 mg from 400 ml of culture. N-terminal sequencing of wild type GM-CSF using automated Edman degradation chemistry yielded the sequence APARSPS, which identically matches the first seven amino acids of mature human GM-CSF, and indicates that the N-terminus is correctly processed (Lee et al., 1985). Purified wild type GM-CSF and commercially available GM-CSF (*E. coli*-expressed; R&D Systems) co-migrated under reducing and non-reducing conditions as shown by Western blot analysis. Both proteins exhibited the expected mobility shift to a higher apparent molecular weight under reducing conditions because of the disruption of the intramolecular disulfide bonds.

D. In Vitro Bioactivities of Wild Type GM-CSF. A cell proliferation assay using the human TF-1 erythroleukemic cell line (Kitamura et al., 1989) was developed to measure bioactivity of wild type GM-CSF. The human TF-1 cell line was obtained from the American Type Culture Collection. The cells were maintained in RPMI 1640 media supplemented with 10% FBS, 50 units/ml penicillin, 50 pg/ml streptomycin and 2 ng/ml recombinant human GM-CSF (*E. coli*-derived; R&D Systems). In general, the bioassays were set up by washing the TF-1 cells three times with RPM 1640 media (no additives) and resuspending the cells at a concentration of $1 \times 10^5$/ml in RPMI 1640 media containing 10% FBS, 50 units/ml penicillin and 50 μg/ml streptomycin (assay media). Fifty μl ($5 \times 10^3$ cells) of the cell suspension was aliquotted per test well of a flat bottom 96 well tissue culture plate. Serial dilutions of the protein samples to be tested were prepared in assay media . Serial dilutions of commercial recombinant human GM-CSF (*E. coli*-expressed; R&D Systems) were analyzed in parallel. Fifty μl of the diluted protein samples were added to the test wells and the plates incubated at 37° C. in a humidified 5% $CO_2$ tissue culture incubator. Protein samples were assayed in triplicate wells. After ~3 days, 20 μl of an MTS/PMS mixture (CellTiter 96 AQueous One Solution, Promega) was added to each well and the plates incubated at 37° C. in the tissue culture incubator for 1-4 h Absorbance of the wells was read at 490 nm using a microplate reader. Control wells contained media but no cells. Mean absorbance values for the triplicate control wells were subtracted from mean values obtained for the test wells. $EC_{50}$s, the concentration at half maximal stimulation, were calculated for each sample to compare bioactivities of the proteins.

The TF-1 cell line shows a strong proliferative response to GM-CSF, as evidenced by a dose-dependent increase in cell number and absorbance values. Commercial GM-CSF and GM-CSF prepared by us had mean $EC_{50}$s of 97 and 105 pg/ml, respectively, in the bioassay (Table 13).

Example 15

Construction, Expression, Purification and Bioactivity of GM-CSF Cysteine Muteins A. Construction of GM-CSF Cysteine Muteins. Thirteen mutant GM-CSF genes were constructed using site-directed PCR-based mutagenesis as described in general by Innis et al., 1990) and Horton et all, (1993) and in the Example 9. We constructed five muteins in the amino-terminal region proximal to Helix A [*-1C (the addition of a cysteine residue onto the natural amino terminus), A1C, A3C, S5C and S7C]; one mutein in the B-C loop [S69C]; three muteins in the C-D loop [E93C, T94C, and T102C]; and three muteins in the carboxy-terminal region distal to Helix D [V125C, Q126C and *128C (the addition of a cysteine residue to the natural carboxy-terminus)]. We also constructed one mutein at a putative N-linked glycosylation site [N27C], which is located at the distal end of Helix A. The template used for the mutagenic PCR reactions was plasmid pBBT268 in which the STII-GM-CSF gene is cloned as an Nde I-Eco RI fragment in pUC18. PCR products were digested with appropriate restriction endonucleases, gel-purified and ligated with pBBT268 vector DNA that had been cut with those same restriction enzymes, alkaline phosphatase treated, and gel-purified. Transformants from these ligations were grown up and plasmid DNAs isolated and sequenced. The sequence of the entire cloned mutagenized PCR fragment was determined to verify the presence of the mutation of interest, and the absence of any additional mutations that potentially could be introduced by the PCR reaction or by the synthetic oligonucleotide primers.

For expression in *E. coli* as proteins secreted to the periplasmic space, the STII-GM-CSF genes encoding the 13 muteins were excised from the pUC18-based pBBT268 derivatives as Nde I-Eco RI fragments of ~450 bp, subcloned into the pBBT257 expression vector, and transformed into *E. coli* W3110.

Using procedures similar to those described here, one can construct other cysteine muteins of GM-CSF. The cysteine muteins can be substitution mutations that substitute cysteine for a natural amino residue in the GM-CSF coding sequence, insertion mutations that insert a cysteine residue between two naturally occurring amino acids in the GM-CSF coding sequence, or addition mutations that add a cysteine residue preceding the first amino acid, A1, of the GM-CSF coding sequence or add a cysteine residue following the terminal amino acid residue, E127, of the GM-CSF coding sequence. The cysteine residues can be substituted for any amino acid, or inserted between any two amino acids, anywhere in the GM-CSF coding sequence. Preferred sites for substituting or inserting cysteine residues in GM-CSF are in the region preceding Helix A, the A-B loop, the B-C loop, the C-D loop, and the region distal to Helix D. Other preferred sites are the first or last three amino acids of the A, B, C, and D Helices. Some preferred positions for cysteine mutations are described in Table 13. Other preferred positions include R67C, G68C, L70C, R30C, T32C, A33C, E35C, N37C, T39C, E45C, D48C, Q50C, E51C, Q99C, T98C, E113C and E127C. In addition to the mutations described above, other preferred residues in these regions for creating cysteine substitutions are described in PCT/US98/14497.

One also can construct GM-CSF muteins containing a free cysteine by substituting another amino acid for one of the naturally occurring cysteine residues in GM-CSF that normally forms a disulfide bond. The naturally occurring cysteine residue that normally forms a disulfide bond with the substituted cysteine residue is now free. The cysteine residue can be replaced with any of the other 19 amino acids, but preferably with a serine or alanine residue. A free cysteine residue also can be introduced into GM-CSF by chemical modification of a naturally occurring amino acid using procedures such as those described by Sytkowski et al. (1998).

Multiple mutants containing two or more added free cysteine residues can also be constructed either by sequential rounds of mutagenesis using the procedures described in Examples 8, 9, 14 and 15 or alternatively by in vitro recombination of individual mutants to construct recombinant expression plasmids encoding muteins containing two or more free cysteines. The preferred multiple mutants would be those that combined two or more cysteine muteins that each retain high activity when PEGylated for example A3C plus S69C, S69C plus E93C, and A3C plus E93C. Other preferred multiple mutants can be deduced based on the data from Table 9 and Table 10 and would include combinations containing two or more mutations from the group including *1C, A1C, A3C, S5C, S7C, S69C and E93C.

Using procedures similar to those described in Examples 14-16, one can express the proteins in *E. coli*, purify the proteins, PEGylate the proteins and measure their bioactivities in an in vitro bioassay. The proteins can be expressed cytoplasmically in *E. coli* or as proteins secreted to the periplasmic space. The muteins also can be expressed in eukaryotic cells such as insect or mammalian cells, using procedures similar to those described in PCT/US00/00931, or related procedures well known to those skilled in the art.

If secretion from eukaryotic cells is desired, the natural GM-CSF signal sequence, or another signal sequence, can be used to secrete the proteins from eukaryotic cells.

B. Expression and Purification of GM-CSF Cysteine Muteins. *E. coli* strains expressing the 13 GM-CSF cysteine muteins were grown, induced and harvested using the protocols described for wild type GM-CSF in Example 14. The muteins were refolded and purified using the protocols described for wild type GM-CSF in Example 14. The muteine eluted from the Q-Sepharose column at approximately 200-230 mM NaCl and from from the Phenyl HP column at approximately 6-8% ammonium sulfate. The muteins were recovered predominantly as monomers, with apparent molecular weights of ~14 kDa by non-reducing SDS-PAGE.

C. Bioactivities of GM-CSF Cysteine Muteins. The 13 purified GM-CSF cysteine muteins were assayed in the TF-1 cell proliferation assay. Protein concentrations were determined using a Bradford protein assay kit (Bio-Rad Laboratories). Commercial wild type GM-CSF and wild type GM-CSF prepared by us were analyzed in parallel on the same days to control for interday variability in the assays. All 13 muteins stimulated proliferation of the TF-1 cells to the same extent as the wild type GM-CSF control proteins. Mean $EC_{50}$s for the 13 muteins ranged from 80 to 134 pg/ml (Table 13).

TABLE 13

Properties of GM-CSF Cysteine Muteins

| GM-CSF Protein | Mutation Location | Mean EC$_{50}$ ± SD (pg/ml) | EC$_{50}$ Range[a] (pg/ml) |
|---|---|---|---|
| R&D wt[b] | — | 97 ± 5 | 90-100 (6) |
| BBT wt[c] | — | 105 ± 8 | 90-115 (14) |
| *-1C | N-terminus | 111 ± 5 | 105-115 (4) |
| A1C | N-terminus | 80 ± 0 | 80-80 (4) |
| A3C | Proximal to A Helix | 108 ± 3 | 105-110 (4) |
| S5C | Proximal to A Helix | 125 ± 6 | 120-130 (4) |
| S7C | Proximal to A Helix | 106 ± 6 | 100-110 (4) |
| N27C | A Helix | 134 ± 30 | 105-160 (4) |
| S69C | B-C loop | 103 ± 10 | 90-110 (4) |
| E93C | C-D loop | 103 ± 14 | 90-115 (4) |
| T94C | C-D loop | 120 ± 4 | 115-125 (4) |
| T102C | C-D loop | 114 ± 3 | 110-115 (4) |
| V125C | Distal to D Helix | 110 ± 0 | 110-110 (4) |
| Q126C | Distal to D Helix | 126 ± 9 | 120-140 (4) |
| *128C | C-terminus | 124 ± 3 | 120-125 (4) |

[a]Observed range of EC$_{50}$ values; number of assays in parentheses.
[b]Commercial wild type GM-CSF (R&D Systems)
[c]Wild type GM-CSF prepared by Bolder BioTechnology Example 16

PEGylation, Purification and Bioactivity of GM-CSF Cysteine Muteins

A1 Preliminary PEGylation studies. Initial PEGylation reaction conditions were determined using A1C, S7C and S69C as the test proteins, TCEP [Tris (2-carboxyethyl) phosphine]-HCl as the reducing agent and 5 kDa cysteine reactive PEGs from Shearwater Polymers. Three jig aliquots of the purified cysteine muteins or wild type GM-CSF were incubated with increasing concentrations of TCEP at room temperature in 100 mM Tris, pH 8.5 in the presence of excess 5 kDa maleimide-PEG or 5 kDa vinylsulfone-PEG (linear forms of a polyethylene glycol polymer composed of a molecular weight average of 5 kDa with a reactive maleimide or vinylsulfone group at one of the polymer ends). The maleimide and vinyl sulfone groups react with Michael nucleophiles, with a high selectivity for mercaptan groups such as those contained on cysteine side chains. After 90 min, the reactions were immediately analyzed by non-reducing SDS-PAGE. The amounts of TCEP and particular PEG reagent that yielded significant amounts of monoPEGylated cysteine protein, without modifying wild type GM-CSF, were chosen for use in subsequent experiments. The titration experiments indicated that at pH 8.5, a 15-fold molar excess of TCEP and 20-fold excess of 5 kDa maleimide-PEG yielded significant amounts of monoPEGylated A1C protein and monoPEGylated S7C protein without detectable di- or tri-PEGylated protein. In the case of GM-CSF S69C, 5 kDa vinylsulfone-PEG was preferred over 5 kDa maleimide-PEG, and yielded significant amounts of monoPEGylated S69C protein. Recombinant wild type GM-CSF was unreactive to the PEGs, even in the presence of a 50-fold molar excess of TCEP. Control experiments indicated that the muteins needed to be partially reduced to be PEGylated.

B. Preparation and Purification of PEGylated GM-CSF Cysteine Muteins: Aliquots of 200 to 300 µg of 10 purified GM-CSF cysteine muteins were PEGylated to provide sufficient material for purification and characterization. The larger PEGylation reactions also were performed for 1.5 hr at room temperature. For each of the mutants, a 15-fold excess of TCEP and 20-fold excess of 5 kDa maleimide-PEG was used. The only exception was S69C where 5 kDa vinylsulfone-PEG was used. These reaction conditions yielded monoPEGylated protein for all ten muteins. At the end of the reaction time, the PEGylation mixture was diluted 20× with ice cold 20 mM Tris, pH 8.0 before being loaded quickly onto an Q-Sepharose column (1 mL, HiTrap) using conditions similar to those described for the initial purification of the GM-CSF muteins (25 mL gradient, 0-0.35 M NaCl in 20 mM Tris pH 8). The presence of the PEG moiety decreases the protein's affinity for the resin, allowing the PEGylated protein to be separated from the non-PEGylated protein. Non-reducing SDS-PAGE analyses of the PEGylation reactions showed that only detectable PEGylated species was the PEG-GM-CSF cysteine mutein monomer, which migrates with an apparent molecular weight 26 kDa. The chromatogram from the Q-Sepharose column showed two major protein peaks. The early eluting major peak (160-200 mM NaCl) was determined to be mono-PEGylated GM-CSF protein by SDS-PAGE. The second major peak (200-230 mM NaCl) was determined to be unreacted GM-CSF protein. Fractions from the early eluting peak containing predominantly monoPEGylated GM-CSF cysteine mutein were pooled and used for bioactivity measurements. All the GM-CSF muteins were PEGylated and purified by the identical protocol. The PEGylated proteins displayed similar apparent molecular weights by SDS-PAGE, except for the PEG-E93C and PEG-T94C muteins, which displayed slightly smaller apparent molecular weights. Four of the cysteine muteins in the N-terminal region (*-1C, A1C, A3C, and S7C) also have been PEGylated on a small scale using 10- and 20 kDa maleimide PEGS. These reactions were performed with 3 µg of each mutein using the conditions described above, and analyzed by SDS-PAGE. Each of these proteins reacted readily with the 10 kDa and 20 kDa PEG reagents, yielding monoPEGylated protein. 40 kDa-PEG-A3C was also prepared following the protocol described above. This protocol was scaled up to provide larger quantities of the 10 kDa-, 20 kDa- and 40-kDa-PEG-A3C protein.

C. Bioactivities of PEGylated GM-CSF Cysteine Muteins: We purified sufficient quantities of 7 muteins (*-1C, A1C, A3C, S5C, S7C, S69C and E93C) modified with a 5 kDa PEG for accurate protein concentration and specific bioactivity measurements. Biological activities of the 7 purified 5 kDa-PEG-GM-CSF cysteine muteins were measured in the TF-i cell proliferation assay. Concentrations of the proteins were determined using a Bradford dye binding assay. All of the PEGylated GM-CSF cysteine muteins showed similar dose-response curves and reached the same level of maximal growth stimulation as wild type GM-CSF. Mean EC$_{50}$s for the PEG-GM-CSF cysteine muteins ranged from 80-123 pg/ml (Table 14).

TABLE 14

Bioactivities of PEGylated GM-CSF Cysteine Muteins

| GM-CSF Protein | 5 kDa PEG Protein Mean EC$_{50}$ ± SD (pg/ml) | 5 kDa PEG Protein EC$_{50}$ Range[a] (pg/ml) |
|---|---|---|
| *-1C | 96 ± 5 | 90-100 (4) |
| A1C | 115 ± 4 | 110-120 (4) |
| A3C | 106 ± 3 | 105-110 (4) |
| S5C | 80 ± 11 | 70-100 (6) |
| S7C | 123 ± 15 | 110-140 (4) |

TABLE 14-continued

Bioactivities of PEGylated GM-CSF Cysteine Muteins

| GM-CSF Protein | 5 kDa PEG Protein Mean $EC_{50}$ ± SD (pg/ml) | 5 kDa PEG Protein $EC_{50}$ Range[a] (pg/ml) |
|---|---|---|
| S69C | 88 ± 6 | 80-95 (4) |
| E93C | 86 ± 5 | 80-90 (4) |

[a]Observed range of $EC_{50}$ values, number of assays in parentheses.

Biological activities of the A3C mutein modified with 10 kDa-, 20 kDa- and 40 kDa-PEG molecules were measured in the TF-I cell proliferation assay. Concentrations of the proteins were determined using a Bradford dye binding assay. Each of the PEG-A3C proteins stimulated proliferation of TF-I cells. Mean $EC_{50}$s for the 10 kDa-, 20 kDa- and 40 kDa-PEG A3C cysteine muteins were 78+/−3 pg/ml, 113+/−5 pg/ml, and 300+/−50 pg/ml, respectively (N=4 assays for each protein).

D. Apparent Molecular weights A3C modified with 5 kDa-, 10 kDa-, 20 kDa- and 40 kDa-K PEGs: The apparent molecular weights of the PEGylated GM-CSF A3C proteins were determined by size exclusion HPLC (SEC) using a Biorad Bio-Sil SEC400-5 column on a Beckman System Gold HPLC. An isocratic gradient consisting of Phosphate Buffered Saline was used as the eluant. Retention times for each protein were used to calculate molecular weights based on a standard curve generated with gel filtration protein standards (BioRad Laboraories, Richmond, Calif.). The PEGylated proteins displayed dramatically increased apparent molecular weights relative to the non-PEGylated GM-CSF (Table 15). Larger PEGs increased the apparent molecular weight of the protein more than smaller PEGs. Similar data were recorded for PEGylated cysteine muteins of GH, IFN-α2, and G-CSF.

TABLE 15

Apparent Molecular Weights of PEGylated GM-CSF Cysteine Muteins by size Exclusion Chromatography

| Protein | Apparent SEC Molecular Weight (daltons) |
|---|---|
| GM-CSF | 20,000 |
| 5 kDa-PEG A3C | 80,000 |
| 10 kDa-PEG A3C | 200,000 |
| 20 kDa-PEG A3C | 470,000 |
| 40 kDa-PEG A3C | 680,000 |

Example 17

Cloning, Expression, Purification and Bioactivity of Wild Type Murine GM-CSF and Cysteine Muteins of Murine GM-CSF We cloned and sequenced a cDNA encoding the mature mouse GM-CSF by RT-PCR of total RNA isolated from the mouse EL4.1L-2 cell line (catalogue # TIB-181) obtained from the American Type Culture Collection (Rockville, Md.). The cells were grown in DMEM media supplemented with 10% FBS, 50 units/ml penicillin and 50 μg/ml streptomycin. The cells were induced for 6 or 24 h with 1 μg/ml PHA-L (Sigma-Aldrich Chemical Company, catalogue # L4144) and 10 ng/ml PMA (Sigma-Aldrich Chemical Company, catalogue # P-1585) in DMEM medium, 10% FBS, 50 units/ml penicillin, 50 λg/ml streptomycin at 37° C. prior to RNA isolation. RNA was isolated from the cells using an RNeasy Mini RNA isolation kit purchased from Qiagen, Inc. (Santa Clarita, Calif.) following the manufacturer's directions. First strand synthesis of single-stranded cDNA was accomplished using a 1st Strand cDNA Synthesis Kit for RT-PCR (AMV) from Boehringer Mannheim Corp and random hexamers were used as the primer. A subsequent PCR reaction using the products of the first strand synthesis as template was carried out with forward primer BB481 [5>GCG AC GCG TAC GCA GCA CCC ACC CGC TCA CCC ATC ACT>3; SEQ ID NO:43] and reverse primer BB482. BB481 anneals to the 24 nucleotides encoding the first eight amino acids of mature mouse GM-CSF. BB481 also adds, immediately 5' to this sequence, nucleotides that overlap the sequences encoding the carboxyterminal 4 amino acids of the E. coli stII signal sequence described above in Example 7 and by Picken et al. (1983). These 11 nucleotides include an Mlu I restriction site. BB482 [5>GCG GAA TTC TTA TTT TTG GAC TGG TTT TTT GCA TTC AAA GGG >3; SEQ ID NO:44] anneals to the nucleotides encoding the carboxyterminal ten amino acids of mouse GM-CSF and adds a TAA translational stop codon and an Eco RI restriction site immediately following the coding sequence. Both the 6 h and 24 h RNA samples yielded a GM-CSF RT-PCR product. The resulting ~400 bp PCR product from the 6 h RNA sample was digested with Mlu I and Eco RI, gel purified, and cloned into pBBT227 [pUC18::stII-CSF(C17S)] which is described in Example 8 above. pBBT227 DNA was digested with Mlu I and Eco RI, alkaline phosphatase treated, and run out on a 1% agarose gel. The ~24 kb vector fragment was purified and used in ligation. The resulting recombinants carry a complete stII leader fused to murine GM-CSF and this "stII-muGM-CSF" construct can be excised as an Nde I-Eco RI fragment of ~450 bp. One clone with the correct sequence (Gough et al, 1984) was designated pUC18:::stII-muGM-CSF or pBBT435. For expression studies the Nde I-Eco RI fragment of pBBT435 was subcloned into the expression vector pBBT257, which is described in Example 14 above. The resulting plasmid, pBBT257:::stII-muGM-CSF or pBBT456 was introduced into E coli W3110 for expression. Wild type mouse GM-CSF was expressed and purified using the protocols for expression and purification of human GM-CSF described in Example 14 above.

Mutant mouse GM-CSF genes can be constructed using site-directed PCR-based mutagenesis as described in general by Innis et al., 1990) and Horton et all, (1993) and in the other Examples above. One mutein, T3C, was constructed in the amino-terminal region proximal to Helix A. The mutagenic PCR reaction was carried out using plasmid pBBT435 (described in Example 17) as template and forward primer BB504 [5>GCG AC GCG TAC GCA GCA CCC TGC CGC TCA CCC ATC ACT>3; SEQ ID NO:45] and reverse primer BB482 [5>GCG GAA TTC TTA TTT TTG GAC TGG TTT TTT GCA TTC AAA GGG>3; SEQ ID NO:46]. BB504 Changes the ACC codon for threonine at position 3 of mature mouse GM-CSF to a TGC codon for cysteine. The resulting ~400 bp PCR product was digested with Mlu I and Eco RI, gel purified, and cloned into pBBT435 that was digested with Mlu I and Eco RI, alkaline phosphatase treated, and gel-purified. One clone with the correct sequence was designated pUC18:::stII-muGM-CSF (T3C). For expression studies the Nde I-Eco RI fragment of this plasmid was subcloned into the expression vector pBBT257, which is described in Example 14 above. The resulting plasmid, pBBT257:::stII-muGM-CSF(T3C), or pBBT469 was introduced into *E coli* JM109 for expression. The T3C mutein of mouse GM-CSF was expressed and purified using the protocols for expression and purification of human GM-CSF described in Example 14 above.

Using procedures similar to those described here, and in Examples 9 and 15 above, one can construct other cysteine muteins of mouse GM-CSF. The cysteine muteins can be substitution mutations that substitute cysteine for a natural amino residue in the GM-CSF coding sequence, insertion mutations that insert a cysteine residue between two naturally occurring amino acids in the mouse GM-CSF coding sequence, or addition mutations that add a cysteine residue preceding the first amino acid of the mouse GM-CSF coding sequence or add a cysteine residue following the terminal amino acid residue of the mouse GM-CSF coding sequence. The cysteine residues can be substituted for any amino acid, or inserted between any two amino acids, anywhere in the mouse GM-CSF coding sequence. Preferred sites for substituting or inserting cysteine residues are in the region preceding Helix A, the A-B loop, the B-C loop, the C-D loop, and the region distal to Helix D. Other preferred sites are the first or last three amino acids of the A, B, C, and D Helices. One also can construct muteins containing a free cysteine by substituting another amino acid for one of the naturally occurring cysteine residues in GM-CSF that normally forms a disulfide bond. The naturally occurring cysteine residue that normally forms a disulfide bond with the substituted cysteine residue is now free. The cysteine residue can be replaced with any of the other 19 amino acids, but preferably with a serine or alanine residue. A free cysteine residue also can be introduced into GM-CSF by chemical modification of a naturally occurring amino acid using procedures such as those described by Sytkowski et al. (1998).

Multiple mutants containing two or more added free cysteine residues can also be constructed either by sequential rounds of mutagenesis using the procedures described in Examples 9 and 15 above or alternatively by in vitro recombination of individual mutants to construct recombinant expression plasmids encoding muteins containing two or more free cysteines. The preferred multiple mutants would be those that combined two or more cysteine muteins that each retain high, or complete, specific activity when PEGylated.

Using procedures similar to those described in Examples 12-14, 15 and 16, one can express purify, and PEGylate mouse GM-CSF muteins and measure biological activities of these proteins in an in vitro bioassay and in vivo efficacy models. The proteins can be expressed cytoplasmically in *E. coli* or as proteins secreted to the periplasmic space. The muteins also can be expressed in eukaryotic cells such as insect or mammalian cells, using procedures similar to those described in PCT/US00/00931, or related procedures well known to those skilled in the art. If secretion from eukaryotic cells is desired, the natural GM-CSF signal sequence, or another signal sequence, can be used to secrete the proteins from eukaryotic cells.

The purified mouse GM-CSF wild type protein, cysteine muteins, and PEGylated forms of the cysteine muteins can be assayed for biological activity with a cell proliferation assay using the NFS60 cell line as described in Examples 8 and 9 above.

Murine wild type GM-CSF and the murine T3C GM-CSF cysteine mutein were isolated from *E. coli* following the procedure described for human WT-GM-CSF (Examples 14-16) with the exception that 30% ammonium sulfate was used to bind the murine proteins to a Phenyl-Sepharose column rather than 15% as described for human GM-CSF. The murine T3C cysteine mutant readily PEGylated with 10 kDa, 20 kDa and 40 kDa PEG maleimide reagents using the protocols described above for human GM-CSF A3C cysteine mutein. Bioactivities of these PEGylated proteins can be measured in the NFS60 cell proliferation assay as described in Examples 8 and 9.

Example 18

*E. coli* Expression and Purification of Wild Type human Erythropoietin

A. Expressing Erythropoietin by secretion in *E. coli*. The DNA encoding wild type human Erythropoietin (Epo) was amplified by PCR from the plasmid pBBT358 (see below), which contains a gene for Epo in the vector pBlueBac 4.5 (Invitrogen), which has been used for expression of Epo in insect cells. The gene for Epo in pBBT358 is similar to the natural cDNA, except for three silent mutations at codons for amino acids 84 and 85 (of mature Epo) that create an XhoI restriction site to facilitate the mutagenesis process.

The three mutations that created the Xho I site were incorporated using the technique of "mutagenesis by overlap extension" as described in Horton et al. (1993) and PCT/US00/00931. The initial, or "primary" PCR reactions for the So I construction were performed in a 50 pl reaction volume in 1X Promega PCR buffer containing 1.5 mM $MgCl_2$, each primer at 0.4 µM, each of dATP, dGTP, dTTP and dCTP at 200 A, 1 ng of template plasmid pBBT132 (the wild type Epo-Flag gene cloned as a BamH I-EcoR I fragment in pUC19, (described in PCT/US00/00931), 2 units of Taq Platinum (BRL), and 0.25 units of Pfu Polymerase (Stratagene). The reactions were performed in a Perkin-Elmer GeneAmp® PCR System 2400 thermal cycler. The reaction program entailed: 95° C. for 5 minutes, 25 cycles of [94° C. for 30 seconds, 56° C. for 30 seconds, 72° C. for 45 seconds], a 7 min hold at 72° C. and a hold at 4° C. The primer pairs used were [BB361×BB125] and [3B362× BB126]. BB361 (S>GTTGGTCAAC TCGAGCCAGC CGTGGGAG>3; SEQ ID NO:79] anneals to DNA sequences encoding amino acid residues 81-89 of mature Epo. BB125 (5>CTATGC GGCATCAGAGCAGATA >3; SEQ ID NO:17) anneals to the pUC19 vector sequence 20 bp downstream of the cloned Epo sequence. The PCR products were run out on a 1.5% agarose gel, excised from the gel, and isolated using a QIAquick Gel Extraction Kit (Qiagen) according to the vendor protocol. These two mutagenized fragments were then "spliced" together in the subsequent, or "secondary" PCR reaction. In this reaction 0.3 µl of each of the gel-purified PCR products of the primary reactions were used as template and BB125 and BB126 were used as primers. The reaction volume was 50 µl and 2.5 units of Taq Polymerase and 0.5 units of Pfu Polymerase were employed. Otherwise, the reaction conditions were identical to those used in the primary reactions. An aliquot of the secondary PCR was analyzed by agarose gel electrophoresis and the expected band of ~190 bp was observed. The bulk of the secondary PCR reaction was "cleaned up" using the QIAquick PCR Purification (Qiagen), digested with Kpn I and Stu I (New England BioLabs) according to the vendor protocols. Following an additional clean up using the QIAquick PCR Purification Kit, the digestion products were ligated with pBBT138 (the wild type Epo-Flag gene cloned as a BamH I~EcoR I fragment in pBlueBac 4.5, (PCT/US00/00931)), that had been cut with with Kpn I and Stu I, treated with calf intestinal alkaline phosphatase (New England BioLabs) and gel purified. The ligation reaction was used to transform *E. coli* and plasmids from resulting transformants were sequenced to identify a clone containing the Xho I site and having the correct sequence throughout the 433 bp Kpn I-Stu I segment. This clone is designated pBBT358.

For expression of Epo fused to the STII signal peptide, (a peptide sequence which directs secretion of the mature protein into the *E. coli* periplasmic, the oligonucleotides used in the PCR reaction were BB583 (5>CCAACGCGTA CGCAGCCCCA CCACGCCTCATC3>; SEQ ID NO:46), which anneals to the N-terminal coding region of the gene, and either BB585 (5>CCGGAATTCT TAACGGTCAC CTGTGCGGCA GGC>3; SEQ ID NO:47) or BB3586 (5>CCGGAATTCT TAGTCACCTG TGCGGCAGGC >3; SEQ ID NO:48), which anneal to the C-terminal coding region of the gene. BB585 includes the codon for Arg166, the C-terminal amino acid predicted by the cDNA sequence, whereas BB586 deletes the Arg166 codon and codes for Asp165 as the C-terminal amino acid. The resulting ~600 bp PCR products were digested with MluI and Eco RI and cloned into a similarly digested pBBT227 (Example 9) vector to create fusions between the STII leader sequence and the amino terminal coding sequence of wild type Epo. The gene formed by PCR using BB583 and BB585 is termed STII-Epo-full length (STII-Epo-FL), and the gene formed by PCR using BB583 and BB586 is termed STII-Epo-des Arg (STII-Epo-dR). STII-Epo-FL and STII-Epo-dR clones with the correct sequence were then subcloned as Nde I-Eco RI fragments into pBBT257 (described in Example 14) to create pBBT477 and pBBT478, respectively. pBBT477 and pBBT478 were transformed into JM109 to create strains BOB578 and BOB579. These strains, along with BOB490 (pBBT257/JM109) were grown overnight in Luria Broth (LB media) containing 10 µg/ml tetracycline at 37° C. in roll tubes. Saturated overnight cultures were diluted to ~0.025 O.D. at $A_{600}$ in LB media containing 10 µg/ml tetracycline and incubated at 37° C. in shake flasks. Typically a 25 ml culture was grown in a 250 ml shake flask. When culture O.D.s reached ~0.3-0.5, IPTG was added to a final concentration of 0.5 mM to induce expression either Epo wild type or Epo des Arg166. For initial experiments, cultures were sampled at 4 and ~19 h post-induction. Samples were analyzed by SDS-polyacrylamide gel electrophoresis (SDS-PAGE) on precast 14% Tris-glycine polyacrylamide gels and stained with Coomassie Blue. Induced cultures of both BOB578 and BOB579 showed a band at approximately 20 kDA, which is consistent with the molecular weight of wild type Epo. This band was not detected in the induced culture of BOB490, the vector-only control.

B. Expressing Met-Erythropoietin in the cytoplasm of *E. coli*. As described in Example 18. A. the DNA encoding wild type human Erythropoietin (Epo) was amplified by PCR from the plasmid pBBT358, which contains a gene for wild type Epo. For expression of met-Epo in the cytoplasm of *E. coli*, the oligonucleotides used in the PCR reaction were BB584 (5>TTC GCTAGCATG CAT GAC CTG CAG GAG GAA ATT TAA ATG GCC CCA CCA CGC CTC ATC 3>; SEQ ID NO:49), which anneals to the N-terminal coding region of the gene, and either BB585 (5>CCGGAATTCT TAACGGTCAC CTGTGCGGCA GGC>3; SEQ ID NO:47) or BB586 (5>CCGGAATTCT TAGTCACCTG TGCG-GCAGGC>3; SEQ ID NO:48), which are described above. The resulting ~600 bp PCR products were digested with MluI and Eco RI and cloned into a similarly digested pBBT227 (Example 9) vector to create genes encoding methionyl-Epo. The gene formed by PCR using BB583 and BB585 is termed met-Epo-full length (met-Epo-FL), and the gene formed by PCR using BB583 and BB586 is termed met-Epo-des Arg (met-Epo-dR). Met-Epo-FL and met-Epo-dR clones with the correct sequence were then subcloned as Nde I-Eco RI fragments into pBBT257 (described in Example 14) to create pBBT479 and pBBT480, respectively.

pBBT479 and pBBT480 were transformed into JM109 to create strains BOB580 and BOB581. Expression experiments with these strains, along with BOB490 (pBBT257/JM109) were the same as those described above for the STII-Epo constructs. Induced cultures of both BOB580 and BOB581 showed a band at approximately 20 kDA, which is consistent with the molecular weight of wild type Epo. This band was not detected in the induced culture of BOB490, the vector-only control.

Example 19

Construction, *E. coli* Expression, Purification and Bioactivity of Erythropoietin Cysteine Muteins A. Construction of Epo Cysteine Muteins. Methods for constructing Epo cysteine muteins using site-directed PCR-based mutagenesis procedures and preferred sites for locations of cysteine muteins in EPO are described in PCT/US00/00931, PCT/US98/14497, and Innis et al. (1990) and White (1993) and the various Examples provided herein. In addition, L80 is another preferred site for a cysteine substitution mutein.

Recombinant erythropoietin and cysteine muteins of erythropoietin can be expressed in *E. coli* using the procedures described in Example 18 for wild type EPO. The cells are lysed using B-per (Pierce) following the manufacture's instructions and the insoluble portion is isolated by centrifigation. The pellet is solubilized using 20 mM cysteine, 6 M guanidine, 20 mM Tris. The mixture is stirred for 1-2 hours at room temperature before being diluted 1:20 (v/v) with 20 m Tris, pH 8, 40 µm copper sulfate, 2% lauroyl sarcosine. The renaturation is allowed to sit at 4° C. for 2448 hours. The refolded EPO and EPO cysteine muteins are purified using an S-Sepharose column equilibrated in 20 mM Mes, pH 5, 0.01% Tween and 20% glycerol (Buffer A). EPO can be eluted from the S-Sepharose column using a linear gradient of 0-1 M NaCl in Buffer A. Secondary columns for further purification of the recombinant EPO, if necessary, include SEC, Blue-sepharose, hydroxyapitite, or MC resins (phenyl, butyl).

Example 20

Construction of Disulfide-linked Trimers and Disulfide-linked Higher Order Multimers of Cysteine Muteins GH variants having more than one "free" cysteine could be constructed and used to create higher order disulfide-linked multimers of hGH as described in PCT/US00/00931. Such a variant could be expressed in *E. coli*, refolded and purified as disclosed in Examples 1 and 2 and PCT/US/00/00931. Subsequent processing steps could then be employed to induce disulfide bond formation as described in Example 2 and PCT/US00/00931. Under such conditions some hGH variants having one free cysteine, such as T3C, are converted virtually quantitatively to disulfide-linked dimers. Under the same or similar conditions intermolecular disulfide formation by an hGH variant having two free cysteines, e.g. a double mutant that combined T3C and another cysteine mutein, would result in a polymerization of hGH molecules and the chain length of such polymers would in principle be unlimited. The chain length could be limited and to some extent controlled by addition to the polymerization reaction of hGH molecules having only one free cysteine such as the T3C variant and/or other cysteine muteins. Disulfide bond formation between the growing polymer and a molecule having only one free cysteine will "cap" or prevent further extension of one of the two polymerization sites in the nascent polymer. A subsequent reaction of a second hGH molecule that has only one free cysteine with the other polymerization site of that nascent polymer terminates polymerization and fixes the length of that polymeric molecule. The average polymer length could be controlled by the stoichiometry of the reactants, i.e. the ratio of hGH molecules with two free cysteines to hGH molecules with one free cysteine. Average shorter polymers would be favored by lower ratios and average longer polymers would be favored by higher ratios. More complex "branched" polymers could be constructed from reactions involving hGH variants with 3 or more free cysteines with hGH variants having only one free cysteine.

Discrete size classes of certain polymers could subsequently be purified by chromatographic methods such as size exclusion chromatography, ion exchange chromatography, hydrophobic interaction chromatography, and the like. Similar procedures to those described for GH could be used to create disulfide-linked dimers and higher order multimers of G-CSF, alpha interferon, GM-CSF and other proteins.

Example 21

Cloning, Expression and Purification of Wild Type human Endostatin

A. Cloning DNA sequences encoding Endostatin. A cDNA encoding Endostatin was amplified by PCR from a human fetal liver cDNA library (Clontech). PCR reactions were carried out with forward primer BB383 (5>GCTAACGCGTACGCACACAGCCACCGC-GACTTCCAGCCG>3; SEQ ID NO:50) and reverse primer BB384 (5>CGGAATTCCTCGAGCTACTTGGAG-GCAGTCATGAAGCT>3; SEQ ID NO:51). Primer BB383 anneals to the 5' end of the coding sequence of human Endostatin and the reverse primer, BB92, anneals to the 3' end of the Endostatin coding sequence. The resulting ~600 bp PCR product was digested with MluI and Eco RI and cloned into a similarly digested pBBT227 (Example 9) vector to create a fusion between the STII leader sequence and the amino terminal coding sequence of human Endostatin After confirming its sequence, the gene was modified for intracellular expression by PCR amplification with forward primer BB434 (5'>GTGCACCATA TGAAGAAGAA CATCGCATTC CTGCTGGCTA GCATGCATGA CCTG-CAGGAG GAAATTTAAA TGCACAGCCA CCGCGACTTC>3'; SEQ ID NO:52) and BB384 (SEQ ID NO:51). BB434 fuses a methionine (met) codon to the amino terminus of Endostatin. The resulting 630 bp fragment was digested with NdeI and SacII and cloned into a similarly digested STII-Endostatin-pUCI 8 plasmid described above. A met-Endostatin clone with the correct sequence (pBBT370) was then subcloned as a Nde I-Eco RI fragment into pBBT257 (described in Example 14) to create pBBT371.

B. Expression of Wild Type met-Endostatin in *E. coli*. pBBT371, which encodes Met-Endostatin wild type, and pBBT257, the parent vector, were transformed into *E. coli* JM109 to create strains BOB460 and BOB490, and into W3110 to create strains BOB461 and BOB340. These strains were grown overnight in Luria Broth (LB media) containing 10 μg/ml tetracycline at 37° C. in roll tubes. Saturated overnight cultures were diluted to ~0.025 O.D. at $A_{600}$ in LB 10 μg/ml tetracycline and incubated at 37° C. in shake flasks. Typically a 25 ml culture was grown in a 250 ml shake flask When culture O.D.s reached ~0.3-0.5, IPTG was added to a final concentration of 0.5 mM to induce expression of human met-Endostatin. For initial experiments, cultures were sampled at 0, 4 and ~19 h post-induction. Samples were analyzed by SDS-polyacrylamide gel electrophoresis (SDS-PAGE) on precast 14% Tris-glycine polyacrylamide gels and stained with Coomassie Blue. Induced cultures of both BOB460 and BOB461 showed a band at approximately 20 kDA, which is consistent with the mature human Endostatin. This band was not detected in the uninduced cultures of BOB460 and BOB461 or in induced or uninduced cultures of BOB490 and BOB340, the vector-only controls. The ~20 kDa band co-migrated with commercially prepared human Endostatin purchased from Calbiochem.

Example 22

Construction, Expression, Purification and Bioactivity of human Endostatin Cysteine Muteins A. Construction of Endostatin Cysteine Muteins. Eleven mutant human Endostatin genes were constructed using site-directed PCR-based mutagenesis procedures similar to those described in PCT/US00/00931 and Innis et al. (1990) and White (1993). Four muteins [*-1C, H2C, RSC, and F7C] were constructed in the amino-terminal region (the amino acid residues are numbered by subtracting 130 from the numbered residues in Hohenester et al. (1998)); three muteins were at residues encoded by sequences around the center of the gene [G90C, G98C, and HI 12C]; and three muteins were in the carboxy-terminal region [Li54C, R157C and S162C]. One additional mutein [R28C] was constructed at a residue within the active site of Endostatin. This could serve as a control protein in the bioassay.

The source of template fragments used for the mutagenic PCR reactions was plasmid pBBT370. PCR products were digested with appropriate restriction endonucleases, extracted using the Qiagen PCR cleanup kit and ligated with pBBT370 vector DNA that had been cut with those same restriction enzymes, alkaline phosphatase treated, and extracted using the Qiagen PCR cleanup kit Transformants from these ligations were grown up and plasmid DNAs isolated and sequenced. The sequence of the entire cloned mutagenized PCR fragment was determined to verify both the presence of the mutation of interest and the absence of any additional mutations that potentially could be introduced by the PCR reaction or by the synthetic oligonucleotide primers.

The cysteine substitution mutation *-1C was constructed using three PCR amplifications as follows. The mutagenic forward oligonucleotide BB531 (5>GAGGAAATTT AAATGTGCCA CAGCCATCGC GACTTCC>3; SEQ ID NO:53) was designed to insert a TGC cysteine codon between the N-terminal ATG methionine codon and the first CAC histidine codon. This oligo was used in PCR#1 with the reverse, non-mutagenic primer BB126 (5>TGTG-GAATTG TGAGCGGATA AC>3; SEQ ID NO:54) which anneals to pUC18 vector sequences within 60 bp downstream of the Endostatin coding sequence. The template for this PCR was a purified 1264 bp Nhe I-ApaL I fragment derived from pBBT370. This fragment contains the entire Endostatin coding sequence and 670 bp of pUC18 sequence downstream of the Endostatin gene, including the sequence to which BB126 anneals. PCR #1 was a 25 μl reaction performed in 1× Promega PCR buffer containing 1.5 MM MgCl$_2$, each primer at 0.4 μM, each of dATP, dGTP, dTTP and dCTP at 200 ELM, 0.5 ng of template fragment, 1 unit of Taq Polymerase (Promega), and 0.1 unit of Pfu Polymerase (Stratagene). The reaction was performed in a Perkin-Elmer GeneAmp® PCR System 2400 thermal cycler. The reaction program entailed: 95° C. for 5 minutes, 22 cycles of [94° C. for 30 seconds, 55° C. for 30 seconds, 72° C. for 45 seconds], a 7 min hold at 72° C. and a hold at 4° C.

PCR #2 was performed using the mutagenic reverse oligonucleotide BB532 (5>GGAAGTCGCG ATGGCT-GTGG CACATTTAAA TTTCCTC>3; SEQ ID NO:55), which is the inverse complement of BB531, and the non-mutagenic primer BB125 (5>TATGCGGCA TCAGAGCA-GATh3; SEQ ID NO: 17), which anneals to pUC18 sequences 40 bp upstream of the Nde I site. The template for PCR#2 was a purified 990 bp Ssp I -EcoR I fragment from pBBT370 containing the entire Endostatin coding sequence and 367 bp of pUC18 sequence upstream of the Nde I site at the 5' end of the Endostatin gene fragment, including the sequence to which BB125 anneals. The components and program for PCR#2 are the same as PCR#1. Ten μl aliquots of PCR#1 and #2 were analyzed by agarose gel electrophoresis and each found to have produced a single fragment of the expected size.

PCR #3 was a 50 μl reaction performed using non-mutagenic primers BB125 and BB126. The template for this PCR was 1 μl of PCR #1 and 0.3 td of PCR #2. The components of PCR #3 were the same as reactions 1 and 2. The reaction program entailed: 95° C. for 5 minutes, 23 cycles of [94° C. for 30 seconds, 56° C. for 30 seconds, 72° C. for 1 min], a 7 min hold at 72° C. and a hold at 4° C. A 10 μl aliquot of PCR #3 was analyzed by agarose gel electrophoresis and found to have generated a 740 bp fragment, as expected. The remainder of the reaction was "cleaned up" using the QIAquick PCR Purification Kit (Qiagen) according to the vendor protocol and digested with Nhe I and BsrG I (New England BioLabs) according to the vendor protocols. Following an additional clean up step using the QIAquick PCR Purification Kit, the digestion products were ligated with pBBT370 that had been cut with Nhe I and BsrG I, treated with calf intestinal alkaline phosphatase (New England BioLabs) and "cleaned up" using the QIAquick PCR Purification Kit The ligation reaction was used to transform *E. coli* JM109 and plasmids from resulting transformants were sequenced. A clone having the *-1C mutation and the correct sequence throughout the 205 bp Nhe I-Bsr I segment was identified.

The substitution mutations H2C, R5C, F7C, and R28C (i.e. changing histidine at position 2 to cysteine, etc.) were constructed and sequence verified using the protocols detailed above for *-1C, except that different mutagenic oligonucleotides were used (Table 16). The forward mutagenic oligonucleotides were always used in conjunction with the reverse, non-mutagenic, primer BB 126 and the purified 1264 bp Nhe I-ApaL I fragment as template, and the reverse mutagenic oligonucleotides were always used in conjunction with forward, non-mutagenic, primer BB 125 and the purified 990 bp Ssp I -EcoR I fragment as template.

TABLE 16

Oligonucleotides used to construct Endostatin cysteine muteins

| Mutation | Oligonucleotide | Direction | Sequence (5'> 3'): Cys codon shown in bold | |
|---|---|---|---|---|
| H2C | BB533 | Forward | GAGGAAATTTAAATTGCAGCCATCGCGACTTCCAG | SEQ ID NO:56 |
| H2C | BB534 | Reverse | CTGGAAGTCGCGATGGCTGCACATTTAAATTTCCTC | SEQ ID NO:57 |
| R5C | BB535 | Forward | ATGCACAGCCACTGCGACTTCCAGCCG | SEQ ID NO:58 |
| R5C | BB536 | Reverse | CGGCTGGAAGTCGCAGTGGCTGTGCAT | SEQ ID NO:59 |
| F7C | BB537 | Forward | GCCACCGCGACTGTCAACCGGTGCTCCAC | SEQ ID NO:60 |
| F7C | BB538 | Reverse | GTGGAGCACCGGTTGACAGTCGCGGTGGC | SEQ ID NO:61 |
| R28C | BB539 | Forward | CATGCGGGGCATCTGCGGCGCCGACTTCCAG | SEQ ID NO:62 |
| R28C | BB540 | Reverse | CTGGAAGTCGGCGCCGCAGATGCCCCGCATG | SEQ ID NO:63 |
| G90C | BB543 | Forward | GGCTCTGTTCTCGTGCTCTGAGGGTCC | SEQ ID NO:64 |
| G90C | BB544 | Reverse | GGACCCTCAGAGCACGAGAACAGAGCC | SEQ ID NO:65 |
| G98C | BB545 | Forward | CCGCTGAAGCCCTGCGCACGCATCTTC | SEQ ID NO:66 |
| G98C | BB546 | Reverse | GAAGATGCGTGCGCAGGGCTTCAGCGG | SEQ ID NO:67 |
| H112C | BB547 | Forward | GACGTCCTGAGGTGCCCGACCTGGCCCAG | SEQ ID NO:68 |
| L154C | BB548 | Forward | GGCCAGGCCTCCAGCCTCTGCGGGGGCAGGCTC | SEQ ID NO:69 |
| L154C | BB549 | Reverse | GAGCCTGCCCCCGCAGAGGCTGGAGGCCTGGCC | SEQ ID NO:70 |
| R157C | BB550 | Forward | CTGCTGGGGGGCTGCCTCCTGGGCCAGAGTGCCGCG | SEQ ID NO:71 |

TABLE 16-continued

Oligonucleotides used to construct Endostatin cysteine muteins

| Mutation | Oligonucleotide | Direction | Sequence (5'> 3'): Cys codon shown in bold | |
|---|---|---|---|---|
| R157C | BB551 | Reverse | CGCGGCACTCTGGCCCAGGAGGCAGCCCCCCAGCAG | SEQ ID NO:72 |
| S162C | BB552 | Forward | CTCCTGGGGCAGTGCGCAGCGAGCTGCCATC | SEQ ID NO:73 |
| S162C | BB553 | Reverse | GATGGCAGCTCGCTGCGCACTGCCCCAGGAG | SEQ ID NO:74 |

Muteins G90C and G98C were constructed by methods similar to those described for *1C, except the mutagenic oligonucleotides were different (Table 16) and the template for PCR #3 was 0.5 µl of PCR #1 and 0.5 µl of PCR #2. In addition, after "clean up," PCR #3 was digested with BsrG I and Bsu36 I (New England BioLabs) and following an additional clean up step, the digestion products were ligated with pBBT370 that had been cut with BsrG I and Bsu36 I, treated with calf intestinal alkaline phosphatase (New England BioLabs) and "cleaned up" using the QIAquick PCR Purification Kit.

Muteins L1,54C, R157C, and S162C were constructed by methods similar to those described for *-1C, except the mutagenic oligonucleotides were different (Table 16) and the template for PCR #3 was 0.3 pl of PCR #1 and 1 µl of PCR #2. In addition, after "clean up," PCR #3 was digested with Bsu36 I and Eco RI and following an additional clean up step, the digestion products were ligated with pBBT370 that had been cut with Bsu36 I and Eco RI, treated with calf intestinal alkaline phosphatase (New England BioLabs) and "cleaned up" using the QIAquick PCR Purification Kit.

Mutein H112C was constructed by methods different in several respects from those described for *-1 C. First, the sequence of the mutagenic forward oligonucleotide used in PCR #1 was different (Table 16) and the volume of the reaction was 50 µl instead of 25 µl. PCR #2 and PCR #3 were not performed, because they were not necessary. Instead, after a 10 µl aliquot was analyzed by gel electrophoresis, this reaction was treated much the same as PCR #3 is normally treated. That is, the remainder of the reaction was "cleaned up" using the QIAquick PCR Purification and digested with Bsu36 I and EcoR I (New England BioLabs) according to the vendor protocols. Following an additional clean up step using the QIAquick PCR Purification Kit, the digestion products were ligated with pBBT370 that had been cut with Bsu36 I and EcoR I, treated with calf intestinal alkaline phosphatase (New England BioLabs) and "cleaned up" using the QIAquick PCR Purification Kit. The ligation reaction was used to transform E. coli JM109 and plasmids from resulting transformants were sequenced.

B. Expression of Cysteine muteins of met-Endostatin in E. coli: Each met-Endostatin Cysteine mutein clone with the correct sequence was subcloned as a Nde I-Eco RI fragment into pBBT257 (described in Example 14) to generate a set of expression plasmids which were transformed in JM109 to create the strains used in expression studies.

These strains were grown overnight in Luria Broth (LB media) containing 10 µg/ml tetracycline at 37° C. in roll tubes. Saturated overnight cultures were diluted to ~0.025 OD. at $A_{600}$ in LB 10 pg/ml tetracycline and incubated at 37° C. in shake flasks. Typically a 25 ml culture was grown in a 250 ml shake flask When a culture O.D. reached ~0.3-0.5, IPTG was added to a final concentration of 0.5 mM to induce expression of the Endostatin Cysteine mutein specific for that stain. Preinduction, 4 hour post-induction, and 16 hr post-induction samples were collected. Samples were analyzed by SDS-polyacrylamide gel electrophoresis (SDS-PAGE) on precast 14% Tris-glycine polyacrylamide gels and stained with Coomassie Blue. Induced cultures of each of the Endostatin cysteine mutein strains showed a band at approximately 20 kDA, which is consistent with the mature human Endostatin. This band was not detected in the uninduced cultures or in induced or uninduced cultures of BOB490, the vector-only control. The ~20 kDa band co-migrated with commercially prepared human Endostatin purchased from Calbiochem.

C. Expression and purification of endostatin and endostatin cysteine muteins: E. coli containing expressed wild type endostatin or endostatin cysteine mutein R5C were pelleted by centrifugation and frozen at −80° C. Cell pellets were thawed and treated with 5 mL of B-PER™ bacterial protein extraction reagent according to the manufacturer's (Pierce) protocols. The insoluble material, which contained the bulk of the endostatin protein, was recovered by centrifugation and resuspended in B-PER This mixture was treated with lysozyme (200 µg/mL) for 10 min to further disrupt the cell walls, and $MgCl_2$ (10 mM final concentration) and protease-free DNAse (2 µg/ml) were added. Insoluble endostatin was collected by centrifugation and washed, by resuspension in water and recentrifugation, to remove most of the solubilized cell debris. For refolding, the resulting pellet containing insoluble endostatin was dissolved in 20 ml of 8 M urea, 10 mM cysteine in 20 mM Tris Base. This mixture was stirred for 120 min at room temperature. Cystine was added to a final concentration of 10 mM before the solublization was diluted into 200 ml of ice cold 3 M urea, 40 µM copper sulfate, 20 mM Tris, pH 7.5. This refold mixture was slowly stirred at 4° C. for 3 days. The pH of the refold mixture was then adjusted to 5.0 with dilute HCl and the mixture was centrifuged before being loaded onto a 5 ml S-Sepharose column (Pharmacia HiTrap) equilibrated in 40 mM sodium phosphate pH 5.0 (Buffer A). The bound proteins were eluted with a linear salt gradient from 0-100% Buffer B (500 mM NaCl, 20 mM sodium phosphate, pH 5.0). The S-Sepharose fractions containing predominantly endostatin were pooled with their pH being adjusted to 7.4 before being loaded onto Heparin-Sepharose (Hi trap) column, previously equilibrated in 20 mM Tris, pH 7.4. The column was eluted with a 0-1 M NaCl salt gradient Heparin column fractions with pure endostatin were pooled and frozen. Endostatin cysteine mutants G90C, G98C, H112C, and R157C have also been partially purified using the above protocol, with the heparin column step omitted.

R5C endostatin cysteine mutein was PEGylated using a 15× excess of 5 kDa PEG maleimide and 10-15-fold excess of TCEP. The reaction yielded monoPEGylated R5C protein.

D. Endostatin Bioassay: Refolded wild type recombinant endostatin and the refolded R5C endostatin cysteine mutein were shown to be biologically active using the MMP-2 inhibition assay described by Kim, et al. (2000).

Bioactivity of the proteins also can be measured in an endothelial cell proliferation inhibition assay. In vitro inhibition of endothelial cell proliferation can be performed as follows. Five thousand HMVEC-L cells (Clonetics) can be plated onto gelatinized 96-well culture plates and incubated (37° C., 5% $CO_2$) for 24 hr in 100 µl HMVEC-L medium containing bFGF. The medium is then replaced with 20 µl of medium containing serial dilutions of endostatin, endostatin cysteine muteins or PEGylated endostatin cysteine muteins, and incubated for 20 min. Eighty µl of fresh HMVEC-L medium containing bFGF is then added to the well. After 72 hr, cell numbers can be determined. The various Endostatin proteins iwill nhibit proliferation of the endothelial cells, as demonstrated by dose-dependent decreases in endothelial cell numbers at the end of the assay.

Example 23

Refolding of Recombinant Angiostatin Cysteine Muteins

Angiostatin is fully active when non-glycosylated and thus, does not require a eukaryotic expression system for production. The coding sequence for human angiostatin, consisting of the first four kringle subunits of human plasminogen, can be PCR-amplified from a human plasminogen cDNA template (available from the American Type Culture Collection, Rockville, Md.). Wild type angiostatin and angiostatin cysteine muteins can be secreted from E. coli by fusing bacterial signal sequences such as those from the STII or ompA proteins onto the N-terminus of mature angiostatin for the purpose of transporting the protein into the periplasmic space. This method has also been used successfully for fragments of angiostatin (Kringle(K)1, K2, K3, and K2-3, (Cao et al., (1996)). Alternatively, angiostatin and angiostati cysteine muteins can be expressed cytoplasmically in E. coli. or other host cell. Angiostatin has 26 cysteines that form 13 disulfides. Therefore, conventional refold protocols without an added cysteine blocking would likely be unsuccessful with a cysteine rich protein like angiostatin. Preferred sites for introducing cysteine residues into angiostatin include K97C (a cysteine residue added onto the N-terminus of mature angiostatin), T365C, 371C, S460C, A463C, and *466C (a cysteine residue added onto the C-terminus of the mature angiostatin protein.

Bacterial cells expressing recombinant angiostatin or the angiostatin cysteine muteins can be lysed using B-per as described by the manufacturer's protocol (Pierce). The insoluble portion can be isolated by centrifugation. The pellet can be solublized using a mixture of 20 mM cysteine, 6 M guanidine, 20 mM Tριs base. The mixture can be stirred for 2 hours at room temperature before being diluted 10 fold into 20 mM Tris, The refold can be held at 4° C. for 1-2 days. At the end of this time, the refold can be centrifuged and the angiostatin protein (or cysteine muyteins) can be purified by using a lysine-sepharose column The refold mixture can be loaded directly onto the column which is previously equilibrated in 20 mM Hepes, 0.15 M NaCl, pH 7.4 Angiostatin (or an angiostatin cystine mutein) can be released from the resin using a gradient of 0-12 mM E-aminocaprioic acid. Further purification, if necessary, can be accomplished using various ion exchange or HIC resins.

Example 24

Peptide mapping of PEGylated proteins

In many instances, peptide maps can be used to verify the site of PEGylation. Typically the PEGylated protein is specifically digested such that the cysteine mutein is present in a peptide with no other cysteine residues. The presence of a PEG covalently attached to the peptide will dramatically change the retention time when the digestion mix is assayed by Reversed Phase HPLC. When GH is digested with trypsin using conditions from the literature (Clark et al., 1996), 21 possible tryptic peptides (T1-T21, numbered consecutively) can be isolated. T1, representing residues 1-8 which includes the mutation T3C, shifts to a slightly earlier retention time for the cysteine mutant (61 minutes) versus wild type (64 minutes) or pituitary growth hormone. When PEGylated with a 5 K PEG, the T1 peptide moves to the end of the chromatogram with a retention time greater than 100 minutes. When GH is digested with endoprotease Lys-C, 10 peptides (L1-10, numbered consecutively) L1 representing residues 1-38 elutes at around 59 minutes for wild type GH and around 61 minutes for the mutein T3C. When PEGylated with a 20 K PEG, L1 is missing from the chromatogram. These data confirm that indeed the PEG moiety is attached to the cysteine residue at postion 3 as predicted rather than at a native cysteine. Enzymatic digestion and RP HPLC analysis of cysteine mutiens of IFN (trypsin and endoprotease Glu-C), GM-CSF (endoprotease Glu-C), and G-CSF (endoprotease Lys-C) before and after PEGylation also showed data that was consistent with a single site of PEGylation at the newly introduced cysteine residue.

Example 25

Peripheral Blood Progenitor Cell Mobilization Initiated by PEG-G-CSF and PEG-GM-CSF Cysteine Muteins Treatment with recombinant G-CSF and recombinant GM-CSF has been shown to mobilize peripheral blood progenitor cells (PBPC) that give rise to more rapid production and engraftment of neutrophils and platelets following chemotherapay. The enhancement of PBPC mobilization (and potentially engraftment rates) can be evaluated in the presence of the PEGylated G-CSF and PEGylated GM-CSF cysteine muteins. Spleenectomized mice strains known to have well defined marrow cell profiles and proliferation kinetics can be given a single or daily (up to 7 days) intravenous or subcutaneous dose(s) of G-CSF (wild-type or Neupogen®) or PEGylated G-CSF cysteine muteins. Each experiment can also contain a group of mice treated only with a carrier, consisting of mouse serum albumin suspended in isotonic saline. Following treatment, peripheral blood can be harvested by cardiac puncture and collected in EDTA-containing tubes. CBC analysis can be performed Bone marrow cells can be harvested by flushing the contents of the femur and marrow. White cell count numbers can be determined by staining with crystal violet and hemacytometer enumeration. Low density cells can be isolated using blood density gradient fractionation and used in progenitor cell assays. The protocol for the progenitor cell assays is outlined in Briddell, et al (1993). Basically, a double-layer agar based system (Bradley et al, 1978) can be used to evaluate both primitive (high proliferative potential-colony-forming cells) and mature (granulocyte-macrophage colony forming cells) progenitor cells. A methylcellulose-based assay system developed by Iscove et al (1974) can be used to evaluate erythroid colony formation. PEGylated G-CSF cysteine muteins will increase mobilization of progenitor and stem cells. Similar studies can be performed with PEGylated GM-CSF cysteine muteins and wild type GM-CSF. Ultimately, the efficiency of transplantation in lethally irradiated mice and the ability to expedite the engraftment process in the presence of PEGylated G-CSF and PEGylated GM-CSF cysteine muteins can be investigated.

REFERENCES

Abrahmsen, L., Moks, T., Nilsson, B. and Uhlen, M. (1986) Nucleic Acids Res.14:7487-7500.

Abuchowski, A., Kazo, G. M., Verhoest, C. R., van Es, T., Kafkewitz, D., Nucci, M. L., Viau, A. T. and Davis, F. F. (1984) Cancer Biochem. Biophys. 7: 175-186.

Alt, F. W., Kellems, R. E., Bertino, J. R., and Schimnke, R. T. (1978) J. Biol. Cher 253:1357-1370.

Arakawa, T., Prestrelski, S. J., Narhi, L. O., boone, T. C. and Kenney, W. C. (1993) J. Protein Chem 12: 525-531.

Balkwill, F. R., Goldstein, L. and Stebbing, N. (1985) Int. J. Cancer 35: 613-617.

Balkwill, F. R. (1986) Methods Enzymology 119: 649-657.

Barik, S. (1993) in "methods in Molecular Biology", White, B. A., ed. (Humana Press, Totawa, N.J.), 15: 277-286.

Bazan, F. (1990) Immunology Today 11: 350-354.

Bazan, J. F. (1991) Cell 65: 9-10.

Bazan, J. F. (1992) Science 257: 410-411.

Becker, G. W. and Hsiung, H. M. (1986) FEBS Lett. 204: 145-150.

Bewley et al., (1969) Biochem. 8: 4701-4708.

Blatt, L. M., Davis, J. M., Klein, S. B. and Taylor, M. W. (1996) J. Interferon and Cytokine Research 16: 489-499.

Blezinger, P., Wang, J., Gondo, M., Quezada, A., Mehrens, D., French, M., Singhal, A., Sullivan, S., Rolland, A., Ralston, R., and Min, W. (1999) Nature Biotechnology 17: 343 Blumberg, H., Conklin, D., xu, W., Grossman, A., Brender, T., Carollo, S., Eagen, M., foster, D., Haldeman, B. A., Hammond, k, Haugen, H., Jelinek, L., Kelley, J.d., madden, K., Maurer, M. F., Parrish-novak, j., Prunkard, D., sexson, S., Sprecher, C., Waggie, K., west, J., Whitmore, T. E., Yao, L., Kuechle, M. k., Dale, B. and chandrasekher, Y. A. (2001) Cell 104: 9-19.

Bolivar, F., Rodriguez, R. L., Greene, P. J., Betlach, M. C., Heyneker, H. L., Boyer, H. W., Crosa, J. H. and Falkow, S. (1977) Gene 2:95-113.

Bollag, D. M., Rozycki, M. D. and Edelstein, S. J. (1996) Protein Methods, 415 pages, Wiley-Liss, NY, N.Y.

Bowen, S., Tare, N., Inoue, T., Yamasaki, M., Okabe, M., Horii, I. And Eliason, J. (1999) Exp. Hematol. 27,425-432.

Bradley, T., Hodgson, G. and Rosendaal, M. (1978) J. Cell Physiol. 94: 517

Braxtor, S. M. (1998) U.S. Pat. No. 5,766,897.

Briddell, R. A., Hartley, C. A., Smith, K. A. and McNiece, I. K. (1993) Blood 82 (6), 1720-1723.

Cantrell, M. A., Anderson, D. and Cerretti, D. P. (1985) Proc. Natl. Acad. Sci. USA 82: 6250-6254.

Cao Y., Ji R. W., Davidson D., Schaller J., Marti D., Sohndel S., McCance S. G., O'Reilly M. S., Llinas M. and Follkan J. (1996) 271:29461-29467.

Cecil, R. and McPhee, J. R. (1959). Advances in Protein Chemistry 14, 255-389.

Chamow & Ashkenazi (1996), Trends in Biotech 14:52-60.

Chang, C. N., Rey, B., Bochner, B., Heyneker, H. and Gray, G. (1987) Gene: 189-196.

Cheah, K-C., Harrison, S., King, R., Crocker, L., Wells, J. R. E. and Robins, A. (1994) Gene, 138: 9-15.

Clark, R., Olson, K., Fuh, G., Marian, M., Mortensen, D., Teshima, G., Chang, S., Chu, H., Mukku, V., Canova-Davis, E., Somers, T., Cronin, M., Winkler, M. and Wells, J. A. (1996) J. Biol. Chem. 271: 21969-21977.

Cox, G. N. and McDermott, M. J. (1994) WO 9412219.

Cox, G. N., McDermott, M. J., Merkel, E., Stroh, C. A., Ko, S. C., Squires, C. H., Gleason, T. M. and Russell, D. (1994) Endocrinology 135: 1913-1920.

Crouse, G. F., McEwan, R. N., and Pearson, M. L. (1983) Mol. Cell. Biol. 3:257-266.

Cunningham, B. C. and Wells, J. A. (1989) Science 244: 1081-1085.

Daopin, S., Piez, K. A., Ogawa, Y., and Davies, D. R. (1992) Science 257: 369-373.

Denefle, P., Kovarik, S., Ciora, T. Gosselet, M., Benichou, J.-C., Latta, M. Guinet, F., Ryter, A. and Mayaux, J.-F. (1989) Gene 85, 499-510.

Donahue, R. E., Wang E. A., Stone, D. K., Kamen, R. L., Wong, G. G., Sehgal, P. K., Nathan, D. G. and Clark, S. C. (1986a) Nature 321:872-5 Donahue, R. E., Wang, E. A., Kaufaman, R. J., Foutch, L., Leary, A. C. and Witek-Giannetti, J. S. (1986b) Cold Spring Harbor Symp. Quant. Biol. 51: 685-692.

Evinger, M. and Pestica, S. (1981) Methods Enzyrol. 79:362-368.

Fuh, G., Cunningham, B. C., Fukanaga, R., Nagata, S., Goeddel, D. V. and Wells, J. A. (1992) Science 256: 1677-1680.

Fujimoto, K., Fukuda, T., and Marumoto., R. (1988) J. Biotechnol. 8:77-86.

Gamba-Vitalo, C., DiGiovanna, M. P., and Sartorelli, A C. (1991) Blood Cells 17:193-205.

Geisse, S., Gram, H., Kleuser, B. and Kocher, H. P. (1996) Prot. Express. Purif. 8:271-282.

Goffin, V., Bernichtein, S., Carriere, O., Bennett, W. F., Kopehick, J. J. and Kelley, P. A. (1999) Endocrinology 140: 3853-3856.

Goodson, R. J. and Katre, N. V. (1990) Biotechnology 8: 343-346.

Gough, N. M., Metcalf, D., Gough, J., Grail, D. and Dunn, A. R. (1985) EMBO J. 4:645-53.

Gough, N. M., Gough, J., Metcalf, D., Kelso, A., Grail, D., Nicola, N. A., Burgess, A. W. and Dunn, A. R. (1984) Nature 309:763-7.

Greenberg, R., Lundell, D., Alroy, Y. and Bonitz, S. (1988) Curr. Microbiol. 17:321-332.

Greenspan, F. S., Li., C. H., Simpson, M. E. and Evans, H. M. (1949) Endocrinology 45:455-463.

Ghrayeb, J., Kirnura, H., Takahara, M., Hsiung, H., Masui, Y. and Inouye, M. (1984) EMBO J. 3:2437-2442.

Hannum, C., Culpepper, J., Campbell, D., McClanahan, T., Zurawski, S. et al. (1994) Nature 368: 643-648.

Henco, K., Brosius, J., et al., (1985) J. Mol. Biol. 185: 227-260.

Hershfield, M. S., Buckley, R. H., Greenberg, M. L. et al., (1987) N.Engl. J. Medicine 316: 589-596.

Hoffman, C. S. and Wright, A (1985) Proc. Nad. Acad. Sci. USA 82: 5107-5111.

Hohenester, E., Sasaki, T., Olsen, B. R. and Timpl, R. (1998) EMBO J. 17:1656-1664.

Horisberger, M. A. and Di Marco, S. (1995) Pharmac. Ther. 66: 507-534.

Horoszewicz, J. S., Leong, S. S. and Carter, W. A. (1979) Science 206:1091-1093.

Horton, R. M. (1993) in "Methods in Molecular Biology", White, B. A., ed. (Humnana Press, Totawa, N.J.), v.15, 214-250.

Hsiung, H. M., Mayne, N. G. and Becker, G. W. (1986) Biotechnology 4: 991-995.

Innis, M. A., Gelfand, D. H., Sninsky, J. J. and White, T. J. eds. (1998) "PCR Protocols: A Guide to Methods and Applications" (Academic Press, San Diego, Calif.).

Iscove, N. N., Sieber, F. and Winterhalter, K. H. (1974) J. Cell Physiol. 83: 309 Ishikawa, M., Iijima, H., Satake-Ishikawa, R., Tsunura, H., et al., (1992) Cell Struct. Function 17, 61-65.

Johns, T. G., Mackay, I. R., Callister, I. A., Hertzog, P. J., Devenish, P. J. and Linnane, A. W. (1992) J. Natl. Cancer Institute 84: 1185-1190.

Johnson, D. L., Middleton, S. A., McMahon, F. Barbone, F. P., Kroon, D., Tsao, E., Lee, W. H., Mulcahy, L. S. and Jolliffe, L. K. (1996) Protein Expression Purif. 7:104-113.

Kadonaga, J., Gautier, A. Straus, D. R., Charles, A. D., Edge, M. D. and Knowles, J. R. (1984) J. Biol. Cher 259: 2149-2154.

Kajigaya, S., Suda, T., Suda, J., Saito, M., Miura, Y., Iizuka, M., Kobayashi, S., Minato, N. and Sudo, T. (1986) J Exp Med 164:1102-13 Kang, S.-H., Na, K-H., Park, J.-H. Park C-I, Lee, S.-Y. and Lee, Y-I. (1995) Biotech. Lett 17, 687-692.

Katre, N. V. (1990) J. Immunology 144: 209-213.

Katre, N. V., Knauf, M. J. and Laird, W. J. (1987) Proc. Natl. Acad. Sci. USA 84: 1487-1491.

Kaufman, R. J. (1990) Meth. Enzymol. 185:537-566.

Khan, F. R. and Rai, V. R. (1990) Bioprocess Technology 7:161-169.

Kim, Y. M., Jang, J., Lee, O., Yeon, J., Choi, E., Kim, K., Lee, S. and Kwon, Y. (2000) Cancer Research 60, 5410-5413.

Kingsley, D. M. (1994) Genes Dev. 8: 133-146.

Kinstler, O. B., Gabriel, N. E., Farrar, C. E. and DePrince, R. B. (1996) International Patent Application Number WO 96/11953.

Kitamura, T., Tange, T., Terasawa, T., Chiba, S., Kuwaki T., Miyagawa, K., Piao, Y. F., Miyazono, K., Urabe, A. and Takaku, F. (1989) J.Cell. Physiol. 140:323-334.

Knusli, C., Delgado, C., Maik, F., Dornine, M., Tejedor, M. C., Irvine, A. E., Fisher, D. and Francis, G. E. (1992) Brit. J Haematol. (1992) 82:654663.

Koshland, D. and Botstein, D. (1980) Cell 20: 749-760.

Kubota, N., Orita, T., Hattori, K., Oh-eda, M., Ochi, N. and Yamazak, T. (1990) J. Biochem. 107: 486-492.

Kuga, T., Komatsu, Y., Yamasaki M., De4kine, S., Miyaji H., Nishi, T., Sato, M., Yokoo, Y., Asano, M., Okabe, M., Morimoto, M. and Itoh, S. (1989) Bioch. Biophys. Res. Comm. 159:103-111

Kutty G., Kutty, R. K., Samuel, W., Duncan, T., Jaworsid, C., and Wiggert, B. (1998) Biochem Biophys. Res. Commun 246: 644-649.

Lawton, L. N., Bonaldo, M. F., Jelenc, P. C., Qiu, L., Baumes, S. A., Marcelino, R. A., de Jesus, G. M., Wellington, S., Knowles, J. A., Warburton, D., Brown, S., and Soares, M. B. (1997) Gene 203: 17-26.

Lee, F., Yokota, T., Otsuka, T., Giemmell, L., Larson, N., Luh, J., Arai, K-I. And Rennick, D. (985) Proc. Natl. Acad. Sci. USA 82:4360-64.

Libby, R. T., Braedt, G., Kronheirn, S. R., March, C. J., Urdal, D. L., Chiaverotti, T. A., Tushinski, R. J., Mochizuki, D. Y., Hopp, T. P., and Cosman, D. (1987) DNA 6:221-229.

Lindner, D. J. and Borden, E. C. (1997) J. Interferon and Cytokine Research 17:681-693.

Lu, H. S., Boone, T. C., Souza, L. M., and Lai, P. H. (1989) Arch. Biochem.Biophys. 268: 81-92.

Lu, H. S., Clogston, C. L., Narhi, L. O., Merewether, L. A., Pearl, W. R. and Boone, T. C. (1992) J. Biol. Chem 267: 8770-8777.

Lucas, B. K., Giere, L. M., DeMarco, M. A., Shen, A., Chisoln, V., and Crowley, C. W. (1996) Nucleic Acids Res. 24:1774-1779.

Lydon, N. B., Favre, C., Bove, S., Neyret, O., Benureau, S., Levine, A. M., Seelig, G. F., Nagabhushan, T. L. and Trotta, P. P. (1985) Biochemistry 24: 4131-4141.

Maisano, F., Testori, S. A., and Grandi, G. (1989) J. Chromatograph. 472: 422-427.

Malik, F., Delgado, C., Knusli, C., Fisher, D. and Francis, G. E. (1992) Exp. Hematol. 20: 1028-1035.

Mark, D. F., Lin, L. S. and Lu, S-D. Y. (1985) U.S. Pat. No. 4,518,584.

Mark, D. F., Lu, S.d., Creasey, Aa., Yanamoto, R. and Lin, L. S. (1984) Proc. Natl. Acad. Sci. USA 81: 5662-5666.

Martin, F. H., Suggs, S. V., Langley, K-E., Lu, H. S., Ting, J., Okino, K. H., Morris, F. C., McNiece, I. K., Jacobsen, F. W., Mendiaz, E. A., Birkett, N. C. et al., (1990) Cell 63: 203-211.

Massague, J. (1990) Annu. Rev. Cell Biol. 6: 597-641.

Matsuzaki, G., Li X.-Y., Ohyama, Y. and Nomoto, K. (1996) Int. J. Immunopharmac. 18: 363-369.

Mayer, P., Lam, C., Obenaus, H., Liehl, E., and Besemer, J. (1987a) Ann N Y Acad Sci 511:17-29.

Mayer, P., Larn, C., Obenaus, H., Liehl, E., and Besemer, J. (1987b) Blood 70:206-13.

Mayer, P., Schutz, E., Lam, C., Kricek, F., and Liehl, E. (1991) J. Infect. Dis.163:584590.

Mayer, P., Werner, F., Lam, C., and Besemer, J. (1990) Exp. Hematol. 18:1026-1033, McDonald, N. Q. and Hendrickson, W. A. (1993) Cell 73: 421-424.

McKay, D. B. (1992) Science 257: 412.

Meyers, F. J., Paradise, C., Scudder, S. A., Goodman, G. and Konrad, M. (1991) Clin.Pharmacol. Ther. 49: 307-313.

Monkarsh, S. P., Ma, Y., Aglione, A., Bailon, P. et al. (1997) Anal. Biochem. 247: 434-440.

Morehead, H., Johnson, P. D. and Wetzel, R. (1984) Biochemistry 23: 2500-2507.

Morioka-Fujimoto, K., Marumoto, R. and Fukuda, T. (1991) J. Biol. Chem 266: 1728-1732.

Moschera, J. A., Woehle, D., Tsai, K. P., Chen, C.-H. and Tarnowski, S. J. (1986) Methods in Enzymology 119:177-183.

Mott, H. R. and Campbell, I. D. (1995) Current Opinion in Structural Biology 5: 114-121.

Nagata, S., Tsuchiya, M., Asano, S., Kziro, Y., Yamazaki, T., Yamamoto, O., Hirata, Y., Kubota, N., Oheda, M., Nomura, H. and Ono, M. (1986a) Nature 319: 415418.

Nagata, S., Tsuchiya, M., Asano, S., Yamamoto, O., Hirata, Y., Kubota, N., Oh-eda, M., Nomura, H. and Yamazaki, T. (1986b) EMBO J. 5: 575-581.

Ohda, M., Hasegawa, M., Hattori, K., Kuboniwa, H., Kojima, T., Orita, T., Tomonou, K., Yamazaki, T., and Ochi, N. (1990) J. Biol. Chem. 265: 575-11435.

Ostermeier, M., De Sutter., K., Georgiou, G. (1996) J. Biol. Chem. 271: 10616-10622.

Paul, W. E. ed (1989) "Fundamental Immunology" (Raven Press, New York, N.Y.).
Perez-Perez, J., Martinez-Caja, C., Barbero, J. L. and Gutierrez, J. (1995) Biochem. Biophys. Res. Comm 210: 524-529.
Pestka, S., Langer, J. A., Zoon, K. C. and Samuel, C. E. (1987) Ann. Rev. Biochem. 56: 727-777.
Picken, R. N., Mazaitis, A. J., Maas, W. K., Rey, M. and Heyneker, H. (1983) Infect. and Immun. 42: 269-275.
Roitt, I. M., Brostoff, J., and Male, D. K. eds. (1989) "Immunology" (Gower Medical Publishers, New York, N.Y. and London, UK)
Rowlinson, S. W. Barnard, R., Bastiras, S., Robins, A. J., Brinkworth, R. and Waters, M. J. (1995) J. Biol. Chem. 270: 16833-16839.
Satake-Ishikawa, R., Ishikawa, W., Okada, Y., Kakitani, M., Kawagishi, M., Matsuki, S. and Asanao, K. (1992) Cell Structure and Function 17: 157-160.
Schuening, F. G., Storb, R., Goehle, S., Nash, R., Graham, T. C., Appelbaum, F. R., Hackman, R., Sandmaier, B. M., and Urdal, D. L. (1989) Exp. Hematol. 17:889-894.
Shanafelt, A. B., Lin, Y., Shanafelt, M.-C., Forte, C. P. et al. (2000) Nature Biotechnology 18: 1197-1202.
Shaw, G., Veldman., G. and Wooters, J. L. (1992) U.S. Pat. No. 5,166,322.
Silvennoinen, O. and Ihle, J. N. (1996) Signalling by the Hematopoietic Cytokine Receptors, R. G. Landes, Company, Austin, Tex.
Souza, L. M., Boone, T. C., Gabrilove, J., Lai, P. H., Zsebo, K. M., Murdock, D. C., Chazin, V. R., Bruszewski J., Lu, H., Chen, K. K., Barendt, J., Platzer, E., Moore, M. A. S., Mertelsmann, R. and Welte, K. (1986) Science 232: 61-65.
Sytkowski, A. J., Lunn, E. D., Davis, K. L., Feldan, L. and Siekman, S. (1998) Proc. Natl. Acad. Sci. USA 95: 1184-1188.
Tanaka, H., Satake-Ishikawa, R., Ishikawa, M., Matsuki, S. and Asano, K. (1991) Cancer Research 51: 3710-3714.
Thompson, S. A. (1992) J. Biol. Chem. 267: 2269-2273.
Torchinskii, Y. M. (1971) in "Sulfhydryl and Disulfide Groups of Proteins" in Studies of Soviet Science (1971) Nauka Press, Moscow.
Trill, J. J., Shatzman, A. R., and Ganguly, S. (1995) Curr. Opin. Biotechnol. 6:553-560.
Trotta, P. B. (1986) Seminars in Oncology XIII Supplement 2: 3-12.
Tuma, R., Rosendahl, M. and Thomas, G. (1995) Biochem. 34: 15150-15156.
Urlaub, G. and Chasin, L. A. (1980) Proc. Natl. Acad. Sci. USA 77:4216-4220.
Van Den Berg, C. L., Stroh, C., Hilsenbeck, S. G., Weng, C.-N., McDermott, M. J., Cox, G. N. and Yee, D. (1997) Eur. J. Cancer 33: 1108-1113.
Voss, T., Fallner, E., Ahorn, H. Krystek, E. Maurer-Fogy, I. Bodo, G., Hauptmann, R. (1994) Biochem. J. 298, 719-725.
Wang, A., Lu, S.-d. and Mark, D. F. (1984) Science 224: 1431-1433.
Weinstein, Y., Ihle, J. N., Lavu, S. and Reddy, E. P. (1986) Proc. Natl. Acad. Sci. USA 83: 5010-5014.
White, B. A (1993) in Methods in Molecular Biology, Vol. 15: PCR Protocols: Current Methods and Applications edited by Humana Press, Inc., Totowa, N.J.
Wingfield, P., Benedict, R., Turcatti, G., Allet, B., Mermod, J.-J., DeLamarter, J., Simana, M. and Rose, K. (1988) Biochem. J. 256, 213-218.
Yamaoka, T., Tabata, Y. and Ikada, Y. (1994) J. Pharm. Sci. 83: 601-606.

While various embodiments of the present invention have been described in detail it is apparent that modifications and adaptations of those embodiments will occur to those skilled in the art. It is to be expressly understood, however, that such modifications and adaptations are within the scope of the present invention.

What is claimed is:

1. A method for preparing a refolded, soluble form of an insoluble or aggregated protein that is a member of the Growth Hormone supergene family and which contains one or more added free cysteine residues, comprising the following steps, in order, of:
   a) causing a host cell to express a protein containing one or more added free cysteine residues that is a member of the growth hormone supergene family in an insoluble or aggregated form;
   b) lysing the cell by chemical, enzymatic or physical means;
   c) separating soluble proteins from insoluble or aggregated proteins;
   d) following step (c) and prior to step (e), dissolving the insoluble or aggregated protein from step (c) in a solution comprising a denaturing agent, a reducing agent and a cysteine blocking agent that forms a reversible mixed disulfide with cysteine, to solubilize and reduce the insoluble or aggregated protein, and to expose the insoluble or aggregated protein to the cysteine blocking agent; and
   e) refolding the protein by reducing the concentrations of the denaturing agent and reducing agents to levels sufficient to allow the protein to renature into a soluble, biologically active form, wherein said refolding step occurs in the presence of the cysteine blocking agent, and wherein the cysteine blocking agent forms a reversible mixed disulfide with at least one added free cysteine residue in said protein.

2. The method of claim 1, wherein said member of the growth hormone supergene family is secreted by the host cell.

3. The method of claim 1, wherein the member of the growth hormone supergene family is expressed by the host cell as an intracellular protein.

4. The method of claim 1, wherein said step (b) of lysing comprises lysing the host cell in the presence of the cysteine blocking agent used in step (d).

5. The method of claim 1, wherein said step (b) of lysing comprises lysing the host cell in the presence of a denaturing agent.

6. The method of claim 1, wherein said step (b) of lysing comprises lysing the host cell in the presence of a denaturing agent and the reducing agent used in step (d).

7. The method of claim 1, wherein said cysteine blocking agent is selected from the group consisting of cysteine, cysteamine, reduced glutathione or thioglycolic acid.

8. The method of claim 1, wherein said cysteine blocking agent is cysteine.

9. The method of claim 1, wherein said reducing agent and said cysteine blocking agent of said step (d) are the same compound.

10. The method of claim 9, wherein said cysteine blocking agent is selected from the group consisting of cysteine, cysteamine, reduced glutathione or thioglycolic acid.

11. The method of claim 1, wherein said cysteine blocking agent of step (d) is a dithiol that, when reduced, acts as a cysteine blocking agent.

12. The method of claim 11, wherein said dithiol is selected from the group consisting of cystine, cysteamine, oxidized glutathione, or dithioglycolic acid.

13. The method of claim 1, wherein the reducing agent is dithiothreitol (DTT) or 2-mercaptoethanol.

14. The method of claim 1, wherein said step (e) of refolding comprises refolding the protein in the presence of glycerol.

15. The method of claim 1, wherein said step (e) of refolding comprises refolding the protein in the presence of an oxidizing agent selected from the group consisting of oxygen, a dithiol, iodine, hydrogen peroxide, dihydroascorbic acid, tetrathionate, or O-iodosobenzoate.

16. The method of claim 1, wherein step (e) of refolding comprises refolding the protein in the presence of a metal ion.

17. The method of claim 16, wherein said metal ion is $Cu^{++}$ or $Co^{++}$.

18. The method of claim 1, wherein said step (e) of refolding comprises refolding the protein in the presence of a denaturing agent.

19. The method of claim 1, wherein said step (e) of refolding comprises refolding the protein in the presence of a dithiol.

20. The method of claim 19, wherein said dithiol is selected from the group consisting of cystine, cystamine, dithioglycolic acid, or oxidized glutathioninee.

21. The method of claim 1, wherein said step (e) of refolding occurs in the presence of a reducing agent.

22. The method of claim 21, wherein said reducing agent is selected from the group consisting of cysteine, DTT, 2-mercaptoethanol, reduced glutathione, cysteamine, thioglycolic acid, or other thiol.

23. The method of claim 1, wherein said insoluble or aggregated protein is a recombinant protein.

24. The method of claim 1, wherein said insoluble or aggregated protein is a derivative or antagonist of a member of the growth hormone supergene family.

25. The method of claim 1, wherein said protein is a cysteine variant of a protein selected from the group consisting of growth hormone, prolactin, placental lactogen, erythropoietin, thrombopoietin, interleukin-2, interleukin-3, interleukin-4, interleukin-5, interleukin-6, interleukin-7, interleukin-9, interleukin-10, interleukin-11, interleukin-12 (p35 subunit), interleukin-13, interleukin-15, interleukin-19, interleukin-20, oncostatin M, ciliary neurotrophic factor, leukemia inhibitory factor, alpha interferon, beta interferon, gamma interferon, omega interferon, tau interferon, granulocyte colony-stimulating factor, granulocyte-macrophage colony-stimulating factor, cardiotrophin-1, macrophage colony stimulating factor, stem cell factor and flt-3 ligand.

26. The method of claim 1, further comprising attaching a cysteine-reactive moiety to at least one added free cysteine in said isolated protein to form a cysteine modified protein.

27. The method of claim 26, wherein the cysteine-reactive moiety is selected from the group consisting of a polyethylene glycol, a polyvinyl pyrolidone, a carbohydrate, a dextran, a peptide, a lipid and a polysaccharide.

28. The method of claim 1, further comprising attaching a cysteine-reactive polyethylene glycol moiety to a cysteine residue in said isolated protein to form a pegylated protein.

29. The method of claim 1, further comprising the step of:
f) isolating the refolded, soluble protein from step (e).

30. A method for covalently modifying said isolated, refolded, soluble protein produced according to claim 29, further comprising the steps of:
g) exposing the isolated protein to a disulfide-reducing agent; and
h) exposing the protein to a cysteine-reactive moiety to obtain a cysteine-modified protein, wherein the cysteine-reactive moiety is attached to at least one added cysteine in said isolated protein.

31. The method of claim 30, wherein said cysteine-reactive moiety is selected from the group consisting of a polyethylene glycol, a polyvinyl pyrolidone, a dextran, a carbohydrate, a peptide, a lipid aid a polysaccharide.

32. The method of claim 30, wherein comprising isolating the cysteine-modified protein from the unmodified protein.

33. The method of claim 1, wherein said protein is a cysteine variant of growth hormone.

34. The method of claim 1, wherein said protein is a cysteine variant of alpha interferon.

35. The method of claim 34, wherein the alpha interferon protein is alpha interferon α2.

36. The method of claim 1, wherein said protein is a cysteine variant of GM-CSF.

37. The method of claim 1, wherein said protein is a cysteine variant of G-CSF.

38. The method of claim 37, wherein said G-CSF cysteine variant contains a non-cysteine amino acid substituted for Cysteine-17.

39. The method of claim 38, wherein the amino acid substituted for cysteine-17 in said G-CSF cysteine variant is serine or alanine.

40. The method of claim 1, wherein said protein is a cysteine variant of erythropoietin.

41. The method of claim 1, wherein the protein is a cysteine variant of interleukin-11.

42. The method of claim 1, wherein the protein is a cysteine variant of beta interferon.

43. The method of claim 1, wherein the protein is a cysteine variant of gamma interferon.

44. The method of claim 1, wherein said denaturing agent is selected from the group consisting of: urea, guanidine and N-lauroyl sarcosine.

45. The method of claim 29, further comprising attaching a polyethylene glycol moiety to said protein to form a pegylated protein.

46. The method of claim 30, wherein said cysteine-reactive moiety is polyethylene glycol.

47. A method for preparing and isolating a refolded, soluble form of an insoluble or aggregated protein that is a member of the Growth Hormone supergene family and which contains one or more added free cysteine residues, consisting essentially of the steps of:
   a) causing a host cell to express a protein containing one or more added free cysteine residues that is a member of the growth hormone supergene family in an insoluble or aggregated form;
   b) lysing the cell by chemical, enzymatic or physical means;
   e) separating soluble proteins from insoluble or aggregated proteins;
   d) following step (c) and prior to step (e), dissolving the insoluble or aggregated protein from step (c) in a solution comprising a denaturing agent, a reducing agent, and a cysteine blocking agent that forms a reversible mixed disulfide with cysteine, to solubilize and reduce the insoluble or aggregated protein, and to expose the insoluble or aggregated protein to the cysteine blocking agent;
   e) refolding the protein by reducing the concentrations of the denaturing agent and reducing agents to levels sufficient to allow the protein to renature into a soluble, biologically active form, wherein said refolding step occurs in the presence of the cysteine blocking agent, and wherein the cysteine blocking agent forms a reversible mixed disulfide with at least one added free cysteine residue in said protein; and
   f) isolating the refolded, soluble protein from step (e).

48. The method of claim 47, wherein step (e) is conducted in the presence of the denaturing agent, a reducing agent, an oxidizing agent, and the cysteine blocking agent.

49. A method for preparing and isolating a refolded, soluble form of an insoluble or aggregated protein that is a member of the Growth Hormone supergene family and which contains one or more added free cysteine residues, comprising the steps of:
   a) causing a host cell to express a protein containing one or more added free cysteine residues that is a member of the growth hormone supergene family in an insoluble or aggregated form;
   b) lysing the cell by chemical, enzymatic or physical means in the presence of a denaturing agent, a reducing agent and a cysteine blocking agent, wherein the insoluble or aggregated protein is denatured and reduced, and is in the presence of the cysteine blocking agent prior to step (c);
   c) refolding the protein by reducing the concentrations of the denaturing agent and reducing agents, to levels sufficient to allow the protein to renature into a soluble, biologically active form, wherein said refolding step occurs in the presence of the cysteine blocking agent, and wherein the cysteine blocking agent forms a reversible mixed disulfide with at least one added free cysteine residue in said protein; and
   d) isolating the refolded, soluble protein from step (c).

* * * * *

UNITED STATES PATENT AND TRADEMARK OFFICE
CERTIFICATE OF CORRECTION

PATENT NO. : 7,306,931 B2  Page 1 of 1
APPLICATION NO. : 10/276358
DATED : December 11, 2007
INVENTOR(S) : Rosendahl et al.

It is certified that error appears in the above-identified patent and that said Letters Patent is hereby corrected as shown below:

On The Title Page Item -66-:

(66) Please delete "Substitute for" and insert --Provisional-- therein.

Claim 12:

Column 105, line 37, delete "cysteamine" and insert --cystamine-- therein.

Claim 20:

Column 105, line 63, delete "glutathioninee" and insert --glutathionine-- therein.

Claim 32:

Column 106, line 46, delete "wherein" and insert --further-- therein.

Signed and Sealed this

Twenty-ninth Day of April, 2008

JON W. DUDAS
*Director of the United States Patent and Trademark Office*